United States Patent
Iyer et al.

(10) Patent No.: US 11,045,658 B2
(45) Date of Patent: Jun. 29, 2021

(54) RECEIVE COIL CONFIGURATIONS FOR IMPLANTABLE MEDICAL DEVICE

(71) Applicant: Medtronic, Inc., Minneapolis, MN (US)

(72) Inventors: Rajesh V. Iyer, Eden Prairie, MN (US); Gordon O. Munns, Stacy, MN (US); John D. Norton, New Brighton, MN (US); Craig L. Schmidt, Eagan, MN (US); Paul B. Young, New Richmond, WI (US)

(73) Assignee: MEDTRONIC, INC., Minneapolis, MN (US)

( * ) Notice: Subject to any disclaimer, the term of this patent is extended or adjusted under 35 U.S.C. 154(b) by 249 days.

(21) Appl. No.: 16/021,067

(22) Filed: Jun. 28, 2018

(65) Prior Publication Data

US 2020/0001095 A1     Jan. 2, 2020

(51) Int. Cl.
| | | |
|---|---|---|
| A61N 1/378 | (2006.01) | |
| A61N 1/375 | (2006.01) | |
| A61N 1/372 | (2006.01) | |
| H01F 5/04 | (2006.01) | |
| H01F 38/14 | (2006.01) | |
| H01F 41/10 | (2006.01) | |
| H01F 5/02 | (2006.01) | |

(52) U.S. Cl.
CPC ......... *A61N 1/3787* (2013.01); *A61N 1/3756* (2013.01); *A61N 1/37229* (2013.01); *A61N 1/37512* (2017.08); *H01F 5/04* (2013.01); *H01F 38/14* (2013.01); *H01F 41/10* (2013.01); *H01F 5/02* (2013.01)

(58) Field of Classification Search
CPC .......... H01F 5/04; A61B 5/686; A61B 5/0031
USPC .......... 320/108, 137, 107; 307/104
See application file for complete search history.

(56) References Cited

U.S. PATENT DOCUMENTS

| | | | |
|---|---|---|---|
| 5,117,824 A | | 6/1992 | Keimel et al. |
| 5,548,218 A | * | 8/1996 | Lu .......................... G01R 33/34 324/318 |

(Continued)

FOREIGN PATENT DOCUMENTS

| | | |
|---|---|---|
| EP | 0693733 A1 | 1/1996 |
| EP | 3045203 A2 | 7/2016 |

(Continued)

OTHER PUBLICATIONS

Office Action from U.S. Appl. No. 16/021,059, dated Apr. 3, 2020, 25 pp.

(Continued)

*Primary Examiner* — John R Downey
(74) *Attorney, Agent, or Firm* — Shumaker & Sieffert, P.A.

(57) ABSTRACT

Systems, devices and methods allow inductive recharging of a power source located within or coupled to an implantable medical device while the device is implanted in a patient. The implantable medical device in some examples include a receive antenna configuration that may include at least one infinity shaped receive coil. One or more of the receive coils may be formed having a curved shape that conforms to a curvature on an inner surface of a portion of a housing of the implantable medical device so that the receive coil or coils may be positioned adjacent to, and in some examples in direct contact with, some portion of the curved inner surface.

29 Claims, 19 Drawing Sheets

(56) References Cited

U.S. PATENT DOCUMENTS

| | | | |
|---|---|---|---|
| 6,008,622 A | 12/1999 | Nakawatase | |
| 6,459,924 B1* | 10/2002 | Creighton, IV | A61B 1/00158 |
| | | | 128/899 |
| 7,474,098 B2* | 1/2009 | King | G01R 33/3415 |
| | | | 324/318 |
| 7,816,915 B2* | 10/2010 | Susel | H01F 41/10 |
| | | | 324/258 |
| 7,924,000 B2 | 4/2011 | Susel et al. | |
| 8,175,716 B2 | 5/2012 | Rahman et al. | |
| 8,612,014 B2 | 12/2013 | Rahman et al. | |
| 8,634,928 B1 | 1/2014 | O'Driscoll et al. | |
| 9,318,780 B2 | 4/2016 | Robertson et al. | |
| 9,620,985 B2* | 4/2017 | Rosenfeld | H02J 7/025 |
| 9,711,272 B2* | 7/2017 | Hassan-Ali | H02J 50/70 |
| 10,821,292 B2 | 11/2020 | Iyer et al. | |
| 2002/0177884 A1* | 11/2002 | Ahn | A61N 1/3787 |
| | | | 607/61 |
| 2004/0135579 A1* | 7/2004 | Takizawa | G01R 33/3415 |
| | | | 324/309 |
| 2008/0027513 A1* | 1/2008 | Carbunaru | A61N 1/3787 |
| | | | 607/60 |
| 2010/0201315 A1* | 8/2010 | Oshimi | H02J 50/10 |
| | | | 320/108 |
| 2011/0257703 A1* | 10/2011 | Kerber | A61N 1/37223 |
| | | | 607/57 |
| 2011/0295340 A1 | 12/2011 | Rahman et al. | |
| 2011/0301668 A1* | 12/2011 | Forsell | H02J 7/00034 |
| | | | 607/60 |
| 2012/0248883 A1* | 10/2012 | Konanur | H02J 50/80 |
| | | | 307/104 |
| 2013/0024059 A1* | 1/2013 | Miller | B60L 11/182 |
| | | | 701/22 |
| 2013/0043734 A1 | 2/2013 | Stone et al. | |
| 2013/0223028 A1 | 8/2013 | Arne et al. | |
| 2013/0241300 A1* | 9/2013 | Miyamoto | G01V 3/10 |
| | | | 307/104 |
| 2013/0241302 A1* | 9/2013 | Miyamoto | H02J 7/025 |
| | | | 307/104 |
| 2013/0285466 A1 | 10/2013 | Wissenwasser et al. | |
| 2014/0028109 A1* | 1/2014 | Simon | H02J 50/90 |
| | | | 307/104 |
| 2014/0094674 A1 | 4/2014 | Nurmikko et al. | |
| 2014/0243848 A1* | 8/2014 | Auricchio | A61N 1/37205 |
| | | | 606/129 |
| 2014/0265620 A1* | 9/2014 | Hoarau | H01F 27/306 |
| | | | 307/104 |
| 2014/0346886 A1 | 11/2014 | Yang et al. | |
| 2015/0321012 A1* | 11/2015 | Cinbis | A61N 1/37288 |
| | | | 607/62 |
| 2016/0022142 A1* | 1/2016 | Bradshaw | G01R 33/34084 |
| | | | 600/415 |
| 2016/0111208 A1* | 4/2016 | Park | H01F 27/006 |
| | | | 307/104 |
| 2016/0111913 A1 | 4/2016 | Robertson et al. | |
| 2016/0131725 A1* | 5/2016 | Sambandamurthy | A61B 5/055 |
| | | | 600/423 |
| 2016/0141097 A1 | 5/2016 | Oo et al. | |
| 2016/0189848 A1* | 6/2016 | Nam | H01F 38/14 |
| | | | 307/104 |
| 2017/0025888 A1* | 1/2017 | Cinbis | A61N 1/37229 |
| 2017/0047636 A1 | 2/2017 | Lee et al. | |
| 2017/0202467 A1* | 7/2017 | Zitnik | A61N 1/36053 |
| 2017/0203109 A1 | 7/2017 | Maile et al. | |
| 2017/0281955 A1 | 10/2017 | Maile et al. | |
| 2018/0140850 A1* | 5/2018 | Linder | A61N 1/3756 |
| 2018/0140851 A1* | 5/2018 | Maile | H02J 7/025 |
| 2018/0140852 A1* | 5/2018 | Linder | A61N 1/37223 |
| 2018/0140853 A1* | 5/2018 | Maile | A61N 1/025 |
| 2018/0141444 A1* | 5/2018 | Lee | B60L 53/305 |
| 2019/0199132 A1* | 6/2019 | Ota | H01F 27/28 |
| 2020/0001094 A1 | 1/2020 | Iyer et al. | |
| 2020/0001095 A1 | 1/2020 | Iyer et al. | |
| 2020/0005988 A1 | 1/2020 | Iyer et al. | |
| 2021/0001131 A1 | 1/2021 | Iyer et al. | |

FOREIGN PATENT DOCUMENTS

| | | |
|---|---|---|
| WO | 0197908 A2 | 12/2001 |
| WO | 2018102435 A1 | 6/2018 |

OTHER PUBLICATIONS

International Search Report and Written Opinion of International Application No. PCT/US2019/039681, dated Nov. 6, 2019, 11 pp.

U.S. Appl. No. 16/021,059, filed by Rajesh V. Iyer et al., filed Jun. 28, 2018.

U.S. Appl. No. 16/021,075, filed by Rajesh V. Iyer et al., filed Jun. 28, 2018.

Maile, PhD, et al., "Wireless Power Transfer for Deeply Implanted Medical Devices (IMD)," Boston Scientific, presented Dec. 5-7, 2016 at Biological & Chemical Sensors Summit, San Diego, CA, 20 slides.

Yates, "Wireless power delivery for ventricular assist devices," Imperial College, London, Dec. 7, 2017, presented Dec. 5-7, 2017 at Biological & Chemical Sensors Summit, San Diego, CA, 40 slides.

Von Novak, "Power Systems for Medical Implants," Qualcomm Technologies, Inc., presented Dec. 5-7, 2016 at Biological & Chemical Sensors Summit, San Diego, CA, 24 slides.

Wilken-Resman, et al., "Power Transfer Prediction Tool for Medical Implants," Qualcomm Technologies, presented Dec. 5-7, 2016 at Biological & Chemical Sensors Summit, San Diego, CA, 15 slides.

Tang et al., "A Low-Operating-Voltage Wireless Intermediate-Range Scheme for Energy and Signal Transmission by Magnet Coupling for Implantable Devices," IEEE Journal of Emerging and Selected Topics in Power Electronics, vol. 3, No. 1, Mar. 2015, pp. 242-251.

Lenaerts, et al., "Inductive powering of a freely moving system," Sensors and Actuators, A 123-124, Jan. 2005, pp. 522-530.

DeTroye et al., "The Calculation and Measurement of Helmholtz Coil Fields," Army Research Laboratory, Nov. 1994, 20 pp.

Jia, et al., "The optimization of wireless power transmission: design and realization," The International Journal of Medical Robotics and Computer Assisted Surgery, Feb. 2012, pp. 337-347.

Notice of Allowance from U.S. Appl. No. 16/021,059, dated Jul. 1, 2020, 16 pp.

Response to Office Action dated Apr. 3, 2020, from U.S. Appl. No. 16/021,059, filed Jun. 17, 2020, 13 pp.

Office Action from U.S. Appl. No. 16/021,075, dated Jun. 11, 2020, 18 pp.

U.S. Appl. No. 17/027,013, naming inventors: Iyer et al., filed Sep. 21, 2020.

Response to Office Action dated Jun. 11, 2020, from U.S. Appl. No. 16/021,075, filed Sep. 1, 2020, 16 pp.

Final Office Action from U.S. Appl. No. 16/021,075, dated Nov. 19, 2020, 21 pp.

Response to Final Office Action dated Nov. 19, 2020, from U.S. Appl. No. 16/021,075, filed Jan. 15, 2021, 18 pp.

Advisory Action dated Jan. 29, 2021, from U.S. Appl. No. 16/021,075, 4 pp.

Prosecution History from U.S. Appl. No. 16/021,059 dated Apr. 3, 2020 through Sep. 30, 2020, 53 pp.

Notice of Allowance from U.S. Appl. No. 16/021,075, dated Mar. 10, 2021, 9 pp.

\* cited by examiner

RECEIVE COIL CONFIGURATIONS FOR IMPLANTABLE MEDICAL DEVICE

TECHNICAL FIELD

The disclosure relates to devices and systems used to recharge a power source located within a medical device that has been implanted in a patient.

BACKGROUND

Various implantable medical devices have been clinically implanted or proposed for therapeutically treating or monitoring one or more physiological and/or neurological conditions of a patient. Such devices may be adapted to monitor or treat conditions or functions relating to heart, muscle, nerve, brain, stomach, endocrine organs or other organs and their related functions. Advances in design and manufacture of miniaturized electronic and sensing devices have enabled development of implantable devices capable of therapeutic as well as diagnostic functions such as pacemakers, cardioverters, defibrillators, biochemical sensors, implantable loop recorders, and pressure sensors, among others. Such devices may be associated with leads that position electrodes or sensors at a desired location, or may be leadless with electrodes integrated into the device housing. These devices may have the ability to wirelessly transmit data either to another device implanted in the patient or to another instrument located externally of the patient, or both.

Although implantation of some devices requires a surgical procedure (e.g., pacemakers, defibrillators, etc.), other devices may be small enough to be delivered and placed at an intended implant location in a relatively noninvasive manner, such as by a percutaneous delivery catheter, or transvenously. By way of illustrative example, implantable miniature sensors have been proposed and used in blood vessels to measure directly the diastolic, systolic and mean blood pressures, as well as body temperature and cardiac output of a patient. As one example, patients with chronic cardiovascular conditions, particularly patients suffering from chronic heart failure, may benefit from the use of implantable sensors adapted to monitor blood pressures. As another example, subcutaneously implantable monitors have been proposed and used to monitor heart rate and rhythm, as well as other physiological parameters, such as patient posture and activity level. Such direct in vivo measurement of physiological parameters may provide significant information to clinicians to facilitate diagnostic and therapeutic decisions. In addition, miniaturized pacemakers that may be implanted directly within a patient's heart with or without the need for external leads, have been proposed, built, and adapted to provide both pacing and other electrical therapy to the patient.

SUMMARY

The disclosure describes implantable medical devices, systems, including receive antenna configurations for implantable medical devices and associated techniques, structures, and assemblies configured to provide recharging of power sources located within medical devices that have been implanted within a patient. The implanted medical devices including these power sources that are to be recharged are often small devices that have been implanted relatively deeply within the patient, for example implanted internally within the heart of a patient. An example of such a device is the Medtronic® Micra™ self-contained pacemaker that is designed to be implanted internally, for example within a chamber of the heart of a patient, and in various examples requires no external leads coupled to the device in order to provide pacing and electrical stimulation to the heart.

The implantable medical devices may include a receive antenna comprising of one or more receive coils positioned within a portion of the housing of the device. The individual receive coils may be made from windings formed from individual electrical conductors, respectively, coupled to recharging circuitry and configured to have currents induced into one or more of the coil windings to provide a recharging current for recharging a power source of the implantable medical device. Configurations of the formations that may be used to arrange an electrical conductor (such as a multi-strand wire) into a receive coil of the receive antenna include flat spiral-wound coils, and coils formed in the shape of an infinity symbol or figure-eight that may include the coil winds formed into two or three loops. Configurations may further include a dual-winding coil configuration forming a two-loop coil winding. Examples of the receive antennas as described herein provide a compact and efficient receive antenna configuration that may be located within a housing of an implantable medical device, including versions of miniaturized implantable medical devices such as the Medtronic® Micra™ self-contained pacemaker.

In some examples, the receive coils of the receive antenna may have a curved shape corresponding to an inner surface of the housing of a portion of the implantable medical device. The receive coil or receive coils in some examples may be placed in direct contact with the inner surface of the housing so that the windings of the receive coil or receive coils extend around and encircle a longitudinal axis of the device. This arrangement of receive coils allows for a high level of inductive coupling efficiency to be achieved between the receive coil(s) and externally generated magnetic fields that are imposed onto the receive coils for the purpose of providing inductive recharging of a power source located with the implantable medical device, such as a battery or a super capacitor.

When there is a need to recharge a power source of an implantable medical device that includes an example of the receive antenna configurations as described in this disclosure, the device including the receive antenna configuration may be placed within a magnetic field (or within a resultant magnetic field formed by a plurality of magnetic fields), which is generated by an externally powered device and one or more recharging coils so that the magnetic field (or the resultant magnetic field) is imposed onto the receive antenna configuration of the implanted medical device. The magnetic field(s) imposed on the device may be arranged to induce electrical current(s) into one or more of the coil windings of the receive antenna. The induced electrical current or currents may be used to recharge the power source of the implanted medical device and/or to provide the electrical power used to directly operate the device. Examples of the receive antennas as described in this disclosure may provide at least a minimum level of recharging current induced into the one or more coil windings of receive antenna for a given energy level of the magnetic field imposed on the multi-axis antenna over a wide range of relative orientations between the implanted device and a direction of the magnetic field(s) imposed onto the device.

In some examples, the changing magnetic field intensity flux through the receive coil induces an electro-motive force (emf) that can drive a charging current for the power source for recharging purposes irrespective of the orientation of the direction of the magnetic field(s) imposed on the device relative to the orientation of the device and the receive antenna. This capability which may allow for recharging the implanted medical device using a simplified recharging system. In some examples, recharging of the implanted medical device may be accomplished using only a single planar recharging coil generating the magnetic field(s), or for example using just a single pair of recharging coils generating the magnetic field(s), to achieve rapid recharge of the implanted medical device without the need for elaborate orientation procedures and/or complex orientation equipment. In addition, this feature may allow recharging of implanted devices where the exact location and/or the orientation of the device may not be precisely known, or may be changing for example due to movement of the device or variations in the orientation of the device following implantation and/or during a recharging session being performed on the device. The receive antenna configurations as described in this disclosure may be especially useful in recharging of deeply implanted devices, (e.g., a device implanted at or more than three centimeters from the closest exterior surface of a patient). As an example, the receive antenna configurations as describe in this disclosure may provide a high level of inductive coupling efficiency between externally generated and applied magnetic field(s) imposed on an implanted device that has been implanted internally or externally to cardiac tissue of the heart of a patient, wherein the heartbeat and other cardiac activity associated with the cardiac tissue at or near the implant site may cause the location and/or the orientation of the implanted device to vary or to be changing during a period of time that a recharging process is being performed on the implanted device.

Examples described in this disclosure are directed to an implantable medical device comprising a rechargeable power source coupled to one or more electrical circuits located within a housing of the implantable medical device, the rechargeable power source configured to provide electrical power to the one or more electrical circuits; a receive antenna configuration comprising at least one receive coil comprising an electrical conductor forming a coil winding, the coil winding positioned within an interior cavity enclosed by the housing of the implantable medical device, the coil winding formed into a curved shape that conforms to a curvature of at least a portion of an inner surface of the housing that at least partially encloses the interior cavity, the coil winding positioned adjacent to the curvature of the inner surface so that the coil winding bends along and is positioned adjacent to the curvature of at least the portion of the inner surface, the receive coil configured to generate an electrical current induced into the at least one receive coil when an externally generated magnetic field is imposed onto the at least one receive coil; and recharging circuitry coupled to the at least one receive coil and to the rechargeable power source, the recharging circuitry configured to receive the electrical current induced into the at least one receive coil and to provide a recharging current to the rechargeable power source, wherein the at least one receive coil and the recharging circuitry are configured to provide at least a minimum level of recharging current for a given level of magnetic field intensity provided by the magnetic field imposed on the at least one receive coil for a plurality of orientations of the magnetic field direction relative to an orientation of the implantable medical device.

Examples described in this disclosure also include a method for forming a receive antenna configuration for an implantable medical device, the method comprising forming an electrical conductor into at least one receive coil, the at least one receive coil comprising a first set of coil windings forming a first loop, a second set of coil windings forming a second loop, and a crossover area coupling the coil windings of the first loop with the coil windings of the second loop to form the at the least one receive coil into an infinity shape; affixing the at least one receive coil comprising the infinity shape to an inner surface of an antenna window portion of a housing of the implantable medical device so that a curvature of a longitudinal axis of the at least one receive coil conforms to a curvature of the inner surface; electrically coupling the at least one receive coil to a recharging circuitry of the implantable medical device; and coupling the antenna window with one or more additional portions of the housing to enclose the at least one receive coil and the recharging circuitry within the housing of the implantable medical device.

Examples described in this disclosure also include a system for recharging a power source located in an implanted medical device implanted in a patient, the system comprising an electrical power source; at least one recharging coil coupled to the electrical power source and configured to generate a magnetic field having a magnetic field direction when electrically energized by the electrical power source; a receive antenna configuration comprising at least one receive coil comprising an electrical conductor forming a coil winding, the coil winding positioned within an interior cavity enclosed by the housing of the implantable medical device, the coil winding formed into a curved shape that conforms to a curvature of at least a portion of an inner surface of the housing that at least partially encloses the interior cavity, the coil winding positioned adjacent to the curvature of the inner surface so that the coil winding bends along and is positioned adjacent to the curvature of at least the portion of the inner surface, the receive coil configured to generate an electrical current induced into the at least one receive coil when an externally generated magnetic field is imposed onto the at least one receive coil; and recharging circuitry coupled to the receive antenna configuration, the recharging circuitry configured to sum electrical current induced into the at least one receive coil and to generate a recharging current to recharge the power source located in an implanted medical device; and a switching device coupled to the multi-axis antenna and the power source of the implanted medical device, the switching device configured to be controlled by the recharging circuitry to couple the recharging current to the power source to recharge the electrical energy stored in the power source, wherein the at least one receive coil and the recharging circuitry are configured to provide at least a minimum level of recharging current for a given level of magnetic field intensity provided by the magnetic field imposed on the at least one receive coil for a plurality of orientations of the magnetic field direction relative to an orientation of the implantable medical device.

Examples described in this disclosure also include a method for recharging a power source located in an implantable medical device implanted in a patient, the method comprising: receiving, at a receive antenna configuration of the implantable medical device, a magnetic field generated by at least one recharging coil located externally to the patient, wherein the magnetic field induces one or more electrical currents in at least one receive coil forming the receive antenna configuration, wherein the at least one of the receive coil comprises a coil winding positioned within an interior cavity enclosed by the housing of the implantable medical device, the coil winding formed into a curved shape that conforms to a curvature of at least a portion of an inner surface of the housing that at least partially encloses the interior cavity, the coil winding positioned adjacent to the curvature of the inner surface so that the coil winding bends along and is positioned adjacent to the curvature of at least the portion of the inner surface, generating, using the receive antenna configuration, one or more electrical currents induced into the at least one receives coil when an externally generated magnetic field is received at the at least one receive coil; summing, by recharging circuitry, the one or more electrical currents to form a recharging current; and applying, by the recharging circuitry, the recharging current to the power source of the implantable medical device to recharge the energy level stored in the power source.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

BRIEF DESCRIPTION OF THE FIGURES

The details of one or more examples of this disclosure are set forth in the accompanying drawings and the description below. Other features, objects, and advantages of this disclosure will be apparent from the description and drawings, and from the claims.

Figure 1:
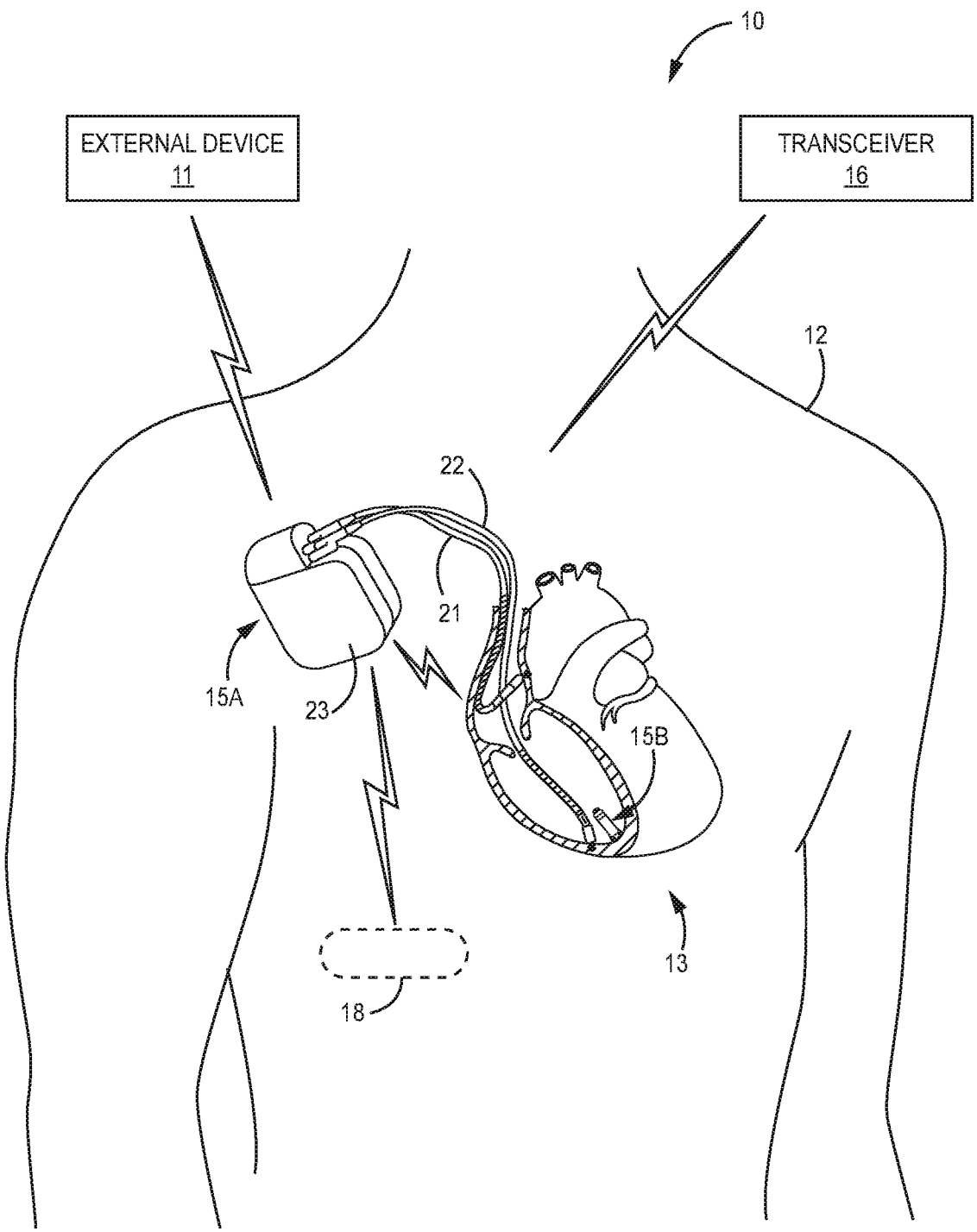
FIG. 1 is a conceptual drawing illustrating an example medical device system in conjunction with a patient according to various examples described in this disclosure.

In the figures, use of a same reference number or a same reference number with a letter extension may be used to indicate a same or corresponding device or element when used in a same drawing or in different drawings. In addition, unless otherwise indicated, devices and/or other objects such as a patient, an implantable medical device, or an electrical device such as an electrical coil, are not necessarily illustrated to scale relative to each other and/or relative to an actual example of the item being illustrated. In particular, various drawings provided with this disclosure illustrate a "patient" represented by a human-shaped outline, and are not to be considered drawn to scale relative to an actual human patient or with respect to other objects illustrated in the same figure unless otherwise specifically indicated in the figure for example by dimensional indicators, or for example as otherwise described in the text of the disclosure.

DETAILED DESCRIPTION

Traditional pacemakers, neurostimulators and implantable loop recorders may use primary batteries with finite energy as an internal power source for electrically powering operation of the device once the device has been implanted in a patient. In various examples of implanted medical devices, a primary (non-rechargeable) battery has a finite energy reservoir which limits its mission life based on its size and energy density (for a given energy usage rate). This limits the useful duration of the implanted device. Once a primary battery is exhausted, replacement of the device may be required, and although replacement of the device may be minimally invasive, it may still be traumatic to the patient. For example, risk of a pocket infection in the area of the implant may occur, which in turn may lead to longer hospital stays and increased cost burden to the patient and/or the insurance companies.

In addition, limits on the available battery energy may result in limits to therapy options for a device and/or the patient. Further, issues related to the implanted medical device may result in a need for a more energy consuming device configuration, which can further shorten the mission life of the implanted device. For example, for a percentage of patients, e.g., for twenty five percent of patients implanted with a left ventricle (LV) lead, the patient does not respond to cardiac resynchronization therapy (CRT) due to sub-optimal lead placement, resulting in the need to apply higher levels of stimulation thresholds, causing excessive battery drain and reduced longevity of the implanted device.

The use of rechargeable batteries or other rechargeable power sources that can be located within an implantable medical device and utilized to power the operation of the device is not a novel concept for overcoming the issues of limited energy primary batteries. However, use of rechargeable batteries or other rechargeable power sources may include additional technical challenges, especially if the device is implanted deep (e.g., more than thee centimeters) within the body of a patient. A rechargeable battery conceptually offers a semi-infinite reservoir of energy in which the size of the battery and charged energy density determines the recharge frequency rather than the mission life (under the assumption of negligible battery capacity fade). A result of a semi-infinite energy source is the opportunity to provide additional features and functions that may otherwise be limited or unavailable given a finite energy source constraint. Another result of this semi-infinite energy source is the potential reduction or elimination of a need to perform a surgically invasive device replacement procedure required due to exhausting the capacity of the primary (i.e., non-rechargeable) battery.

In some examples, conventional inductive power transfer to implanted medical devices may be limited to devices implanted at a depth of approximately two inches or less from the surface (e.g., skin) of the patient. Fast recharge of small, deeply implanted devices such as the Medtronic® Micra™ Pacemaker via transdermal, magnetic induction when the device is implanted for example within a chamber of the heart of a patient presents many challenges. These challenges include providing an adequate magnetic field intensity and frequency at the implant location such that rapid recharge can be accomplished without exceeding electric field and magnetic field exposure safety limits for a patient, while also accounting for an uncontrolled orientation of the implanted device, and while accounting for the true spatial location of the device in addition to the device/antenna orientation.

Further, the exact orientation of the device itself following implantation of the device may be unknown, and/or may change after the implantation procedure. Thus, an implanted medical device that includes a receive antenna, such as a uni-directional or a planar antenna that may be sensitive to the alignment of the direction of imposed magnetic field with an orientation of the axis of the antenna, may require more elaborate procedures and/or more complex recharging equipment for the purpose of achieving an efficient level of inductive coupling between the magnetic field and the receive antenna. This requirement may necessitate use of more elaborate alignment procedures to align direction of the magnetic field with the orientation of the receive antenna, or may require use of more complex arrangements of multiple pairs of recharging coils in order to achieve an acceptable level of inductive coupling efficiency between the magnetic field and the receive antenna during a recharging procedure.

The devices, systems, and methods described in this disclosure address many of the challenges associated with recharging these power sources within implanted medical devices. The systems, devices, and methods described in this disclosure provide examples of receive antenna configurations including one or more receive coils that may be incorporated within an implantable medical device. These receive antenna configurations may allow for fast recharge of a battery or other rechargeable power source within a small, deeply implanted medical device, such as the Micra™ leadless pacemaker. In some examples, the system for recharging may use a single recharging coil, or in some examples a single pair of recharging coils, to generate the magnetic field used to recharge the implanted device. The receive antenna configurations as described in this disclosure may be arranged to generate at least a minimum level of recharging current for a given level of power imposed by a magnetic field on the receive antenna configuration over a wide range of variations in the orientation of the magnetic field relative to an orientation of the implanted device. The use of the receive antenna configurations as described in this disclosure may therefore reduce or eliminate the need for a complex alignment procedure, and/or more complex arrangements of recharging coil(s) in order to achieve a minimum level of inductive coupling efficiency between the implanted medical device and the magnetic field or fields imposed on the device as part of a recharging procedure.

Thus, it is possible to establish a recharging current in the receive coils of a receive antenna configuration provide in and example implanted medical device as described this disclosure that may be independent of the orientation of the recharging magnetic field imposed on the receive antenna configuration, and thus provides a high level of inductive coupling efficiency between the receive antenna and the magnetic field imposed onto the device using just a single external recharge coil, or using just a single pair of external recharge coils for purposes of recharging the power source of the device.

The systems, devices, and methods described herein provide a way to allow a magnetic field(s) to efficiently induce electrical energy (e.g., an electrical current) into a receive antenna configuration included within an implanted medical device with a minimum need for complex alignment and orientation between with the receive antenna and the magnetic field. The induced electrical energy may be used to recharge a power source of the implanted medical device using the externally provided magnetic field, and/or to power electronic circuitry included within or coupled to the implanted medical device, including devices that may be considered deeply implanted within the patient, (e.g., devices implanted more than two to three centimeters below the skin or outer surface of the patient).

The ability to quickly recharge the power source of an implanted medical device, for example within a one hour recharging period of time on a monthly or yearly cycle, without the need to explant the device to do so, allows at least the benefits described above, including use of a smaller power source to help miniaturize the implantable medical device itself, and to allow more power, and thus greater functionality for the implanted medical device by providing an overall longer mission lifespan for the device using a smaller sized power source. Examples of the receive antenna configurations as described in this disclosure have been shown to provide recharging currents in devices implanted at about fifteen centimeters within a body of a patient, and to safely deliver over 30 milliwatts of power to the rechargeable battery of the implanted device. Such examples include a pair of infinity shaped receive coil positioned along the curvature of an inner surface of an antenna window portion of a housing of an implantable medical device.

Throughout the disclosure, a reference to a "receive coil" refers to a coil winding formed from an electrical conductor that may or may not be coupled with one or more additional "receive coils" to form a receive antenna for an implantable medical device. The use of the term "receive antenna" may be used in place of or interchangeably with the term "receive coil" in any context referring to a coil winding that is coupled to recharging circuitry of an implantable medical device and that may be configured to have current induced into the coil winding for the purpose of providing electrical energy to recharging a rechargeable power source of the implantable medical device and/or to provide electrical power to operate the electrical circuitry of the implanted medical device for the purpose of operating the device.

Throughout the disclosure reference is made to a "magnetic field" or to "magnetic fields" in the context of a magnetic field or magnetic fields that is/are generated externally to an implantable medical device, and imposed onto the implanted medical device for the purpose of inducing a current into one or more coil windings of a receive antenna configuration of the implantable medical device. Examples of waveforms that may represent one or more parameters of a magnetic field or magnetic fields are illustrated and described with respect to FIG. 13. However, the examples of magnetic field(s) are not limited to magnetic fields(s) having the particular waveforms illustrated in FIG. 13. Any magnetic field or magnetic fields having a parameter (e.g., amplitude or phase) of the magnetic field that varies in time, or that varies in time with respect to the magnetic field direction of the magnetic field, such that a time rate of change of the net magnetic flux intensity imposed onto the coil windings of the receive antenna configuration, and a corresponding change in the electro-motive force (emf) configured to generate a current or currents in the one or more coil windings is contemplated by the use of the terms "magnetic field" and "magnetic fields" throughout this disclosure.

FIG. 1 is a conceptual drawing illustrating an example medical device system 10 in conjunction with a patient 12 according to various examples described in this disclosure. The systems, devices, and methods described in this disclosure may include examples of a single antenna or multiple antennas located within an implanted medical device, and provided for charging of these internal, and in some instances deeply implanted medical device, such as IMD 15A, IMD 15B, and/or sensor circuits 18, as illustrated and described with respect to FIG. 1. For purposes of this description, knowledge of cardiovascular anatomy is presumed, and details are omitted except to the extent necessary or desirable to explain the context of the techniques of this disclosure. The systems, devices, and methods described herein may provide efficient inductive coupling of an externally generated recharging power source to the electrical circuitry that is internal to IMD 15A, IMD 15B, and/or sensor circuits 18, even when these devices are deeply implanted within the patient. The implanted devices may include multi-axis and/or multi-directional antennas that are not necessarily orientation specific with respect to inductive coupling efficiencies between the receive antenna of the device being inductively recharged and the orientation of one or more recharging coils being used to provide the magnetic field or fields being imposed on the device for the purpose of inductively recharging a power source, such as a battery, located within the device. In various examples, IMD 15A and/or IMD 15B may represent examples of a defibrillator, a cardiac resynchronization pacer/defibrillator, or a pacemaker. Medical device system 10 typically includes provisions for interrogating these devices through a wireless or other communication protocol using an external "instrument," such as external device 11, that includes an external-to-the-patient antenna and software/firmware interface to collect data.

In some existing examples of implantable medical devices, techniques used to keep the size dimensions of the implanted device(s) as small as possible include use of a planar antenna (receiving/transmitting antenna), for example an antenna comprising a conductive trace printed on a planar surface such as a substrate, provided within the implantable medical device. One possible advantage of a planar antenna design, as compared to for example an antenna having multiple axes of orientation, is that the uni-directional or planar format of the antenna may take up less space within the device, and may be more easily packaged into the device when size and space are of concern. A main disadvantage associated with the planar antenna may be that inductive coupling efficiencies with respect to receiving power transmitted from outside the patient to the receive antenna may be orientation specific. For example, the direction of orientation of the electromagnetic and magnetic fields being imposed on an implanted medical device relative to the orientation (e.g., a normal axis of orientation) of a planar-type receive antenna within the implanted medical device may have an effect on the inductive coupling, and thus the efficiency of transferring power from the electromagnetic and magnetic fields to the receive antenna.

For some implanted devices, the orientation of the implanted device, and thus the orientation of the receive antenna within the device may not be precisely known, or may shift at some point in time after implantation of the device into a patient. This shifting of position may include movement of the implanted device itself during the time when recharging of the implanted device is being performed. Such shift in position may be caused by motions of tissue in the area of the implantation, such as cardiac activity including heartbeats of the heart of the patient, and/or movements of the patient themselves, such as when the patient is walking, standing, or changing position, including patient movements while the patient is lying down. Such changes in orientation of the implanted medical device may cause issues, including variations in the power transfer efficiencies, while attempting to inductively recharge a power source, such as a battery, that is located within the implanted medical device. Similar issues may also exist when inductively powering the implanted device for the purpose of operating the device for example when the implanted device does not include an internal power source for operating the device, and relies on inductively coupled electrical energy for powering the operation of the device.

Examples of compact receive antennas and receive antenna configurations as described in this disclosure may overcome some or all of these orientation issues related to coupling efficiencies and recharging of an implanted medical device. For example, use of the receive antennas as described in this disclosure within an implantable medical device may minimize or even eliminate the issues related to the orientation of the receive antenna(s) relative to one or more recharging coils being used to provide the magnetic fields inducing current in the receive antenna, while providing a compact antenna configuration that may be fitted within the housing of the implanted medical device. Because the examples of the receive antennas as described in this disclosure are not generally orientation specific, for example as a planar antenna might be, a recharging process performed on an implanted medical device having the receive antenna configurations as described herein may be performed by a single external coil such as a planar recharging coil, a simple wound non-planer coil, a helical planer or non-planer coil, or by a single pair of recharging coils, arranged for example as a Helmholtz coil. A higher level of coupling efficiency may be achievable between the recharging coil(s) and the receive antenna of the implanted medical device during the recharging process regardless of the relative orientation of the recharging coils relative to the receive antenna(s) of the implanted medical device, for example compared to an implanted medical device having a uni-directional antenna and a same relative orientation between the uni-directional antenna and the recharging coil(s).

In the illustrated example of FIG. 1, medical device system 10 includes an implantable medical device (IMD) 15A coupled to a ventricular lead 22 and an atrial lead 21. IMD 15A may include an example of a receive antenna or a plurality of receive antennas as described herein, the receive antenna or plurality of receive antennas configured to have currents induced into winding of these antenna by one or more magnetic fields provided externally to the patient 12, the induced current for use in recharging a power source within IMD 15A. In various examples, IMD 15A is an implantable cardioverter-defibrillator (ICD) capable of delivering pacing, cardioversion and defibrillation therapy to the heart 13 of a patient 12. Ventricular lead 22 and atrial lead 21 are electrically coupled to IMD 15A, and extend into the heart 13 of patient 12. Ventricular lead 22 includes electrodes (not labeled in FIG. 1) positioned on the lead in the patient's right ventricle (RV) for sensing ventricular electrogram (EGM) signals and pacing in the RV. Atrial lead 21 includes electrodes (not labeled in FIG. 1) positioned on the lead in the right atrium (RA) of patient 12 for sensing atrial EGM signals and pacing in the RA. Ventricular lead 22 and/or atrial lead 21 may also include coil electrodes used to deliver cardioversion and defibrillation shocks.

The term "anti-tachyarrhythmia shock" may be used herein to refer to both cardioversion shocks and defibrillation shocks. IMD 15A may use both ventricular lead 22 and atrial lead 21 to acquire cardiac electrogram (EGM) signals from patient 12 and to deliver therapy in response to the acquired data. Medical device system 10 is shown as having a dual chamber IMD configuration, but other examples may include one or more additional leads, such as a coronary sinus lead extending into the right atrium, through the coronary sinus and into a cardiac vein to position electrodes along the left ventricle (LV) for sensing LV EGM signals and delivering pacing pulses to the LV. In other examples, a medical device system may be a single chamber system, or otherwise not include atrial lead 21. Although not specifically illustrated in FIG. 1, IMD 15A may in additional to, or in the alternative to intravascular leads 21 and 22, be coupled to one or more extravascular leads, including one or more epicardial leads, substernal leads, and/or subcutaneous leads, or some combination thereof.

Processing circuitry, sensing circuitry, a receive antenna configuration, a rechargeable power source, and other circuitry configured for performing the techniques described herein or otherwise ascribed to IMD 15A may be housed within a sealed housing 23. Housing 23 (or a portion thereof) may be conductive so as to serve as an electrode for pacing or sensing, or as an active electrode during defibrillation. As such, housing 23 is also referred to herein as "housing electrode" 23. Housing 23 may include one or more electrodes with a high-capacitance portion and a low-capacitance portion. The high-capacitance portion and the low-capacitance portion may be formed using two different materials.

IMD 15A may transmit EGM signal data and cardiac rhythm episode data, as well as data regarding delivery of therapy by IMD 15A, to an external device 11. External device 11 may also be referred to as an "instrument," which may include any of the devices described throughout the disclosure as devices located externally to the patient, and in some examples may be included as part of a recharging system configured to recharge the battery or other power source provided within IMD 15A. For example, external device 11 as illustrated in FIG. 1 may be a computing device, e.g., used in a home, ambulatory, clinic, or hospital setting, to communicate with IMD 15A via wireless telemetry. External device 11 may be coupled to a remote patient monitoring system, such as Carelink®, available from Medtronic plc, of Dublin, Ireland. External device 11 may be, as examples, a programmer, external monitor, or consumer device, e.g., a smart phone.

External device 11 may be used to program commands or operating parameters into IMD 15A for controlling its functioning, e.g., when configured as a programmer for IMD 15A. External device 11 may be used to interrogate IMD 15A to retrieve data, including device operational data as well as physiological data accumulated in IMD 15A memory. The interrogation may be automatic, e.g., per a schedule, or in response to a remote or local user command. Examples of communication techniques used by IMD 15A and external device 11 may include tissue conductance communication (TCC) and/or radio frequency (RF) telemetry, which may be an RF link established via Bluetooth®, WiFi, or medical implant communication service (MICS).

As illustrated in FIG. 1 the medical device system 10 may also include an intracardiac pacing device IMD 15B. IMD 15B may include an example of a receive antennas configuration as described herein, the receive antenna configuration configured to have currents induced into one or more receive antennas by one or more magnetic fields provided externally to the patient 12, the induced current for use in recharging a power source within IMD 15B. In the illustrated example, IMD 15B is implanted in the right ventricle of patient 12, e.g., internal to the heart 13 of patient 12. In some examples, one or more IMDs like IMD 15B (not shown in FIG. 1) may additionally or alternatively be implanted within other chambers of heart 13, such as the left ventricle, or attached to the heart epicardially.

IMD 15B may be configured to sense electrical activity of heart 13 and deliver pacing therapy, e.g., bradycardia pacing therapy, cardiac resynchronization therapy (CRT), anti-tachycardia pacing (ATP) therapy, and/or post-shock pacing to heart 13. IMD 15B may be attached to an interior wall of heart 13 via one or more fixation elements (not shown in FIG. 1), that penetrate the cardiac tissue. These fixation elements may secure IMD 15B to the cardiac tissue and retain an electrode (e.g., a cathode or an anode) on the housing of IMD 15B in contact with the cardiac tissue. In addition to delivering pacing pulses, IMD 15B may be capable of sensing electrical signals using the electrodes carried on the housing of IMD 15B. These electrical signals may be electrical signals generated by cardiac muscle and indicative of depolarizations and repolarizations of heart 13 at various times during the cardiac cycles of heart 13.

In some examples, IMD 15A and IMD 15B may both be configured to deliver pacing therapy. In such examples, IMD 15A and IMD 15B may delivery pacing therapy to the right and/or left ventricles of heart 13, respectively, to provide CRT pacing. Additionally, IMD 15A and IMD 15B may both be configured to detect tachyarrhythmias, and deliver anti-tachyarrhythmia therapy. IMD 15A and IMD 15B may be configured to coordinate their cardiac rhythm detection and treatment activities. In some examples, IMD 15A and IMD 15B may engage in wireless communication between IMD 15A and IMD 15B to facilitate such coordinated activity. The wireless communication may by via TCC, and may be one-way communication in which one device is configured to transmit communication messages and the other device is configured to receive those messages, or two-way communication in which each device is configured to transmit and receive communication messages.

In various examples, IMD 15B is configured to wirelessly communicate directly with external device 11, using any of the communication protocols described above with respect to IMD 15A. External device 11 may be, as examples, a programmer, external monitor, or consumer device, e.g., a smart phone, that may be used to program commands or operating parameters into IMD 15B for controlling the functioning of the device. External device 11 may be used to interrogate IMD 15B to retrieve data, including device operational data as well as physiological or neurological data accumulated in memory of IMD 15B. The interrogation may be automatic, e.g., according to a schedule, or in response to a remote or local user command. In some examples, communication between IMD 15B and external device 11 may take place through IMD 15A, wherein IMD 15B communications with IMD 15A, and IMD 15A communicates with external device 11. Examples of communication techniques used by IMD 15A and/or 15B and external device 11 are not limited to any particular communication technique or communication protocol, and in some examples TCC or RF telemetry, which may be an RF link established via Bluetooth®, WiFi, or medical implant communication service (MICS).

In various examples, communications provided from IMD 15A and/or IMD 15B may include data and/or other information related to the inductive charging of these devices. For example, when an electromagnetic or magnetic field is imposed on IMD 15A and/or IMD 15B for the purpose of inductively charging these device(s), information related to the coupling efficiency of inductive coupling to the device, and/or for example the state of charge (e.g., percent of charge relative to a full charge) may be transmitted from one or both of IMD 15A and/or IMD 15B to external device 11 as part of the recharging process. Other information, such as time to full charge, rate of recharge, and temperature of the device may also be provided as transmitted information from the device(s) being recharged. In some examples, this information may be used to adjust parameters, such as the field strength of the magnetic field(s) used to induce the energy in the antenna for recharging of IMD 15A and/or IMD 15B, to adjust the relative orientation of the recharging coil(s) providing the magnetic field(s), and/or for example to provide information used to reconfigure the electrical parameters being used to energize the coil or coils that are providing the fields used for the inductively coupled recharging of these device(s).

In addition, information may be provided by IMD 15A and/or IMD 15B that is indicative of the level of the recharging of one or both of IMD 15A and/or IMD 15B that has been achieved or completed, which may then be used to determine when to further regulate, stop, or otherwise terminate the recharging process. For example, during the recharging process IMD 15A and/or IMD 15B may transmit data or other information indicating that the device, respectively, is fully recharged. The indication may then be used by the external devices providing the fields (not show in FIG. 1) to stop the charging process, which may include removing the fields used to recharge IMD 15A and/or IMD 15B from being imposed on these devices. In addition, monitoring the temperature of these devices may be important, as overheating of an implanted device as a result of the recharging process may damage the device, or present a safety issue for the patient. Adjustments to the intensities of the fields being imposed on the device(s), and/or termination of the recharging process altogether may be made based on the monitored temperature of the device being recharged as a part of the recharging process.

In various examples, one or more additional sensor circuits may be located outside of or separately located relative to the IMD 15A and/or IMD 15B. These one or more additional sensor circuits are illustratively represented by sensor circuits 18. Sensor circuits 18 may include a single sensor circuit configured to sense a particular physiological or neurological parameter associated with patient 12, or may comprise a plurality of sensor circuits, which may be located at various and/or different positions relative to patient 12 and/or relative to each other, and may be configured to sense one or more physiological parameters associated with patient 12.

For example, sensor circuits 18 may include a sensor operable to sense a body temperature of patient 12 in a location of the sensor circuits 18, or at the location of the patient where a temperature sensor coupled by a lead to sensor circuits 18 is located. In another example, sensor circuits 18 may include a sensor configured to sense motion, such as steps taken by patient 12 and/or a position or a change of posture of patient 12. In various examples, sensor circuits 18 may include a sensor that is configured to detect breaths taken by patient 12. In various examples, sensor circuits 18 may include a sensor configured to detect heartbeats of patient 12. In various examples, sensor circuits 18 may include a sensor that is configured to measure systemic blood pressure of patient 12.

In some examples, one or more of the sensors comprising sensor circuits 18 may be implanted within patient 12, that is, implanted below at least the skin level of the patient. In some examples, one or more of the sensors of sensor circuits 18 may be located externally to patient 12, for example as part of a cuff or as a wearable device, such as a device imbedded in clothing that is worn by patient 12. In various examples, sensor circuits 18 may be configured to sense one or more physiological parameters associated with patient 12, and to transmit data corresponding to the sensed physiological parameter or parameters to IMD 15A, as represented by the lightning bolt coupling sensor circuits 18 to IMD 15A.

Transmission of data from sensor circuits 18 to IMD 15A in various examples may be performed via wireless transmission, using for example any of the formats for wireless communication described above. In various examples, transmission of data from one or more of the sensors comprising sensor circuits 18 to IMD 15A may be performed by a wired connection between the sensor circuits 18 and IMD 15A. When sensor circuits 18 are implanted devices that are implanted within patient 12, one or more of the sensor circuits may include any examples of the receive antenna(s)

described in this disclosure, and the recharging techniques as described throughout this disclosure may be used to also recharge a power source, such as a battery, located within the implanted sensor(s) that is configured to provide power to operate the sensor and/or to provide power to operate the device.

In various examples, IMD 15A and or IMD 15B may communicate wirelessly to an external device (e.g., an instrument or instruments) other than or in addition to external device 11, such as transceiver 16 shown in FIG. 1. In various examples, transceiver 16 as shown in FIG. 1 is an access point, such as access point 235 illustrated and described with respect to FIG. 12, that provides a wireless communication link between IMD 15A and/or IMD 15B, and a network such as network 237 illustrated and described with respect to FIG. 12. In various examples, transceiver 16 is communication circuitry included within recharging circuitry 231 shown in FIG. 12, wherein communication circuitry of recharging circuitry 231 is configured to communicate with IMD 15A and/or IMD 15B during the recharging process of these devices, as further described below. Examples of communication techniques used by any of the devices described above with respect to FIG. 1 and transceiver 16 may include radiofrequency (RF) telemetry, which may be an RF link established via Bluetooth®, WiFi, or medical implant communication service (MICS).

For the remainder of the disclosure, a general reference to a medical device system may refer collectively to include any examples of medical device system 10, a general reference to IMD 15 may refer collectively to include any examples of IMD 15A and/or IMD 15B, a general reference to sensor circuits may refer collectively to include any examples of sensor circuits 18, a general reference to an external device may refer collectively to any examples of external device 11, and a general reference to a transceiver may refer collectively to any examples of transceiver 16.

Figure 2A:
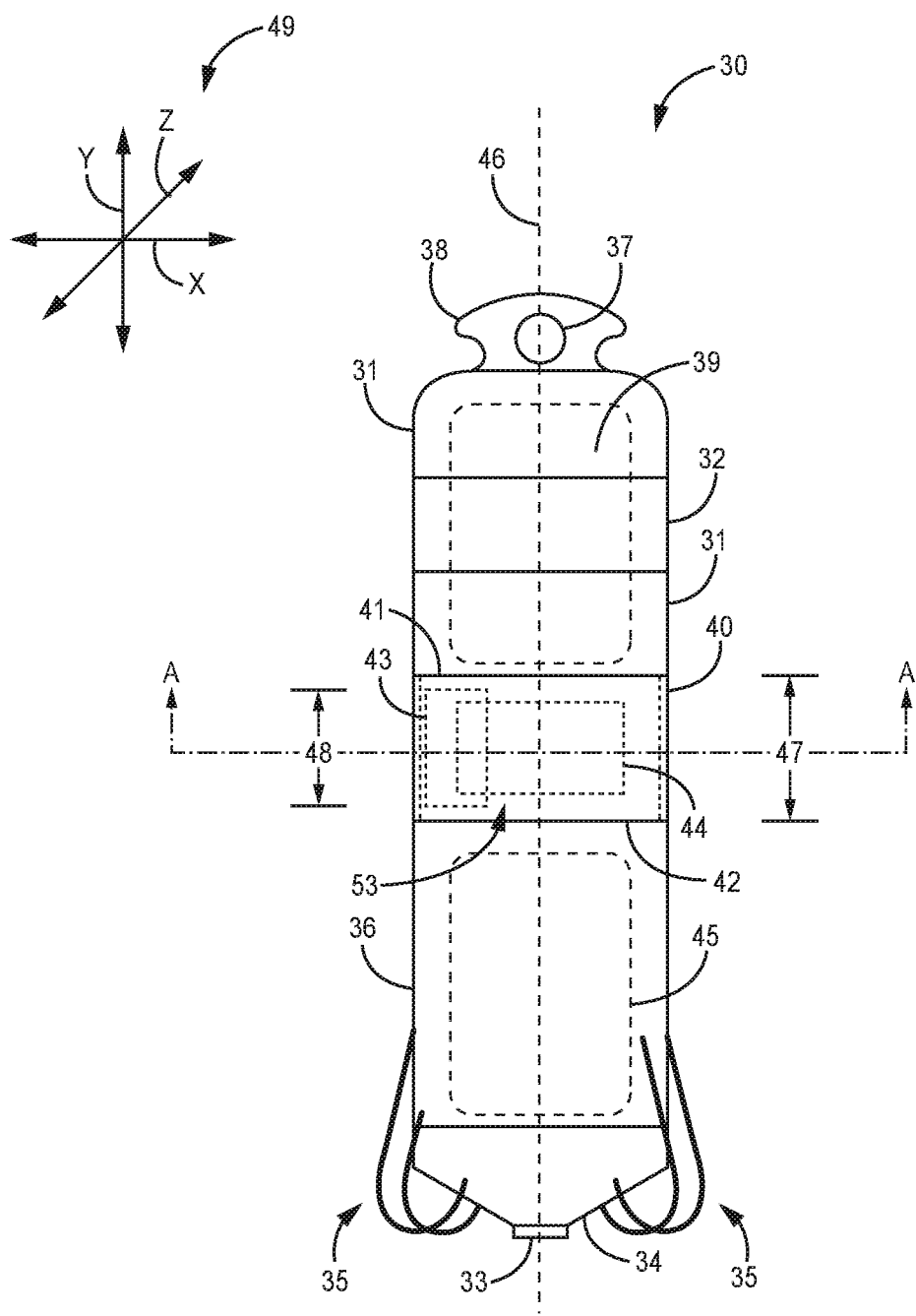
FIG. 2A is a conceptual drawing illustrating an example configuration of an implantable medical device according to various examples described in this disclosure.

FIG. 2A is a conceptual drawing illustrating an example configuration of an implantable medical device 30 according to various examples described in this disclosure. FIG. 2A includes an illustration of a three-axis coordinate system 49 including a Y-axis extending vertically in FIG. 2A, an X-axis perpendicular to the Y-axis and extending horizontally across FIG. 2A, and a Z-axis that is perpendicular to both the Y-axis and the X-axis, the Z-axis extending into and out of the drawing sheet in FIG. 2A. In FIG. 2A, the Y-axis corresponds to the longitudinal axis 46 of device 30, and any plane including the X-axis and the Z-axis may be a cross-section of device 30 taken perpendicular to the Y-axis and longitudinal axis 46. Reference to these axes of the three-axis coordinate system 49 may be used in the description of device 30 and in additional figures of this disclosure to help describe the various features and techniques described in this disclosure related to implantable medical devices.

Device 30 in some examples is an intracardiac pacing device designed to be implanted within a chamber of the heart of a patient. Device 30 in some examples is IMD 15B as illustrated and described with respect to FIG. 1. Device 30 may be configured to be implanted in the right ventricle of the heart of a patient, as depicted in FIG. 1, or in some other chamber of the heart of a patient. As shown and described with respect to FIG. 2A, device 30 may be an example of an implantable medical device that includes a receive antenna 43 that may be used to provide a recharging current that is induced into the coils of the antenna for the purpose of recharging a power source, such as battery 39, within device 30. Device 30 may include a second antenna 44 arranged as part of a receive antenna configuration of device 30. Second antenna 44 that may be used to provide some or an additional recharging current induced into the coil of second antenna 44 to electrical circuitry of device 30 for the purpose of recharging a power source, such as battery 39, within device 30. In some examples, device 30 is a Medtronic® Micra™ Transcatheter Pacing System developed by Medtronic, plc, of Dublin, Ireland.

As shown in FIG. 2A, device 30 includes first housing portion 31, an antenna window 40, a second housing portion 36, and an end cap 34 are coupled together to form the external portions of device 30. First housing portion 31, antenna window 40, second housing portion 36, and end cap 34 may be "sealingly joined" together as shown in FIG. 2A to form a hermetically sealed housing that encloses a battery 39, receive antenna 43, and electronic circuitry 45 of device 30. If a second antenna 44 is included as part of device 30, the housing may also enclose the second receive antenna. As used herein, "sealingly coupled" or "sealingly joined" refers to two or more individual pieces of material that are mechanically coupled to one another at a joint or along a seam that is formed to provide a hermetic seal at the joint or seam between the two or more pieces. Device 30 as shown in FIG. 2A may further include electrode 32, electrode 33, fixation mechanisms 35, and a flange 38 including an opening 37. Each of first housing portion 31, second housing portion 36, and end cap 34 may be formed from electrically insulating material, and/or may be coated with a polymer material such as a poly-para-xylylene (commonly "PARYLENE"). In some examples, one or both of first housing portion 31 and second housing portion 36 may be formed of a same material, in some examples comprising titanium. In some examples, end cap 34 may be formed in whole or in part from an electrically insulative material, such as a plastic material.

Although device 30 is generally described as including one or more electrodes, device 30 may typically include at least two electrodes (e.g., electrodes 32 and 33) to deliver an electrical signal (e.g., therapy such as cardiac pacing) and/or provide at least one sensing vector. Electrode 32 is carried on the portion of device 30 indicated as first housing portion 31, and electrode 33 is carried at the upper or distal portion of end cap 34. Electrodes 32 and 33 may be considered leadless electrodes in the sense that they are not coupled to device 30 or a housing portion of device 30 by a lead. In the example of FIG. 2A, electrode 32 may be a ring or cylindrical electrode disposed on the exterior surface of first housing portion 31, and electrode 33 may be disposed on the exterior surface of end cap 34. Electrode 33 may be a circular electrode positioned to contact cardiac tissue upon implantation of device 30. Electrode 33 may be used as a cathode and electrode 32 may be used as an anode, or vice versa, for delivering cardiac pacing such as bradycardia pacing, cardiac resynchronization therapy (CRT), antiachy-cardia pacing (ATP), or post-shock pacing. However, electrodes 32 and 33 may be used in any stimulation configuration. In addition, electrodes 32 and 33 may be used to detect intrinsic electrical signals from cardiac muscle tissue. Electrode 33 may be configured to contact cardiac tissue such as an interior wall of the right ventricle, when device 30 is implanted with the heart of a patient.

Fixation mechanisms 35 may be arranged to attach device 30 to cardiac tissue. Fixation mechanisms 35 may be active fixation tines, screws, clamps, adhesive members, or any other mechanisms for attaching a device to tissue. As shown in the example of FIG. 2A, fixation mechanisms 35 may be constructed of a memory material, such as a shape memory alloy (e.g., nickel titanium), that retains a preformed shape.

During implantation, fixation mechanisms 35 may be flexed forward to pierce tissue, and then allowed to flex back towards second housing portion 36. In this manner, fixation mechanisms 35 may be embedded within the target tissue to secure device 30 in place relative to the target tissue. A flange 38 may be provided on one end of device 30, for example extending from first housing portion 31, to enable tethering and/or extraction of device 30. For example, a suture or other device may be inserted around flange 38 and/or through opening 37 and attached to tissue. In this manner, flange 38 may provide a secondary attachment structure to tether or retain device 30, for example within the heart. Flange 38 and/or opening 37 may also be used to extract device 30 once the device needs to be explanted (or removed) from the patient if such action is deemed necessary.

Electronic circuitry 45, including communication and/or recharging circuitry coupled to receive antenna 43, and a power source such as battery 39, may be enclosed within the housing of device 30. Second antenna 44 is also electrically coupled to electronic circuitry 45 when the second antenna 44 is provided as part of device 30. The power source of device 30 is not limited to any particular type of power source, and in some examples, is a rechargeable battery, which is coupled to the electronic circuitry 45 and is configured to provide electrical power to the electronic circuitry. The electronic circuitry 45 of device 30 is not limited to any particular type or arrangement of electronic devices, and may include any type(s) of devices arranged to perform any of the functions ascribed to device 30. For example, electronic circuitry 45 may include electronic devices configured to perform any of the patient monitoring functions and/or to provide electrical stimulation therapy through the electrodes (e.g., electrodes 32 and 33) of device 30.

Electronic circuitry 45 may further include communication circuitry configured to provide wireless communication between device 30 and other devices, such as external device 11 and/or transceiver 16 as illustrated and described above for example with respect to FIG. 1. The communication circuitry of device 30 may utilize receive antenna 43 for transmission of signals transmitted from device 30, and for reception of signals transmitted to device 30 from one or more devices external to device 30. In other examples, device 30 includes a separate telemetry antenna (not shown in FIG. 2A, but for example antenna 67 shown in FIG. 3A) that is coupled to the communication circuitry of device 30 and used for the reception and transmission of wireless communications to and from, respectively, device 30.

Referring again to FIG. 2A, receive antenna 43 may be configured to receive electrical energy imposed on device 30 in the form of one or more magnetic fields, and to recharge battery 39 using energy inductively coupled to receive antenna 43 from these field(s), which may also be referred to as wireless power transfer. In order to achieve a high level of inductive coupling efficiency between receive antenna 43 and the magnetic field(s) being imposed on device 30 for the purpose of recharging battery 39, receive antenna 43 may be arranged as a multi-directional antenna, for example arranged as an infinity-loop coil as described in this disclosure, that allows a current to be induced into receive antenna 43 when a magnetic field is impose on the receive antenna that may have a magnetic field direction orientated in one of a variety of possible orientations relative the orientation of device 30. Examples of the "receive coils" including but not limited to infinity-loop coils as described throughout this disclosure that are configured as receive antenna(s) of the implanted medical device, such as device 30, may provide a high level of inductive coupling efficiency between the receive antenna configuration and the magnetic fields imposed on the implanted device over a wide range of variation in the relative orientations between the magnetic field direction(s) of the imposed magnetic field(s) and the orientation of the implanted device.

As shown in FIG. 2A, receive antenna 43 is positioned within device 30 to align with and in some examples be encircled by a portion of antenna window 40. Receive antenna 43 may be affixed to a ferrite sheet, or may be affixed directly in a portion of the inner surface of antenna window 40. Receive antenna 43 and/or the ferrite sheet (when provided) may have a height dimension 48 corresponding to the direction of orientation of longitudinal axis 46. Antenna window 40 may extend along and encircle the Y-axis so that an interior cavity 53 extending along the Y-axis (longitudinal axis 46) of device 30 is formed in the shape of an upright cylinder having a circular cross-sectional shape and having a height corresponding to longitudinal dimension 47 as shown in FIG. 2A.

When receive antenna 43 is provided having the windings of the antenna formed in a curved shape that corresponds to the curvature of the inner surface of antenna window 40, additional space is provided within interior cavity 53 in portions of the cavity not occupied by receive antenna 43, such as the area around the center of the interior cavity. The additional space may be utilized for additional antenna(s), such as a second antenna 44 configured to provide additional inductive current for recharging and/or for operating device 30. The additional space may also be utilized for an additional antenna (not shown in FIG. 2A) that may be configured to support transmission and reception of wireless communications between device 30 and other devices external to device 30. Examples of the receive coils, and the arrangement of these receive coils as receive antenna(s) for use in providing inductive recharging of implanted devices, may provide a compact and efficient arrangement of antenna(s) to allow recharging of the devices where these antenna and antenna configurations are implemented in small sized implantable devices while eliminating or minimizing the orientation problems that might be present in similar devices that utilize uni-directional antenna or a single planar receive antenna.

As further described below, the antenna window 40 may be formed of a material, for example a material having a high value relative to electrical resistivity, that allows for transmission of the electromagnetic energy being imposed onto device 30 for recharging purposes to penetrate and pass through the antenna window 40, and reach the receive antenna 43, and second antenna 44 when the second antenna is provided. The antenna window 40 may be referred to as being formed from a "radio transmissive" material that also provides a low relative dielectric constant (i.e., high relative electrical resistivity), and low magnetic permeability. Electrical resistivity may be represented by the Greek letter $\rho$ (rho), and in International System (SI) units is measured in ohm-meter ($\Omega$-m), and which may vary for a given material based on temperature. An example of a material, such as certain metals, that may be considered to be a good electrical conductor and thus have a low value for electrical resistivity, is copper, having a $\rho$ value of approximately $1.68 \times 10^{-8}$ $\Omega$-meter at 20 degrees Celsius (° C.). An example of a material that may be considered to be poor conductors of electricity, e.g., an electrical insulator, and thus having a high value for p may include glass, which can have a p value in a range of $1 \times 10^{10}$ to $1 \times 10^{14}$ $\Omega$-meter at 20° C. Another example of a material having a high value for p is sapphire, which in some examples has a p value of in a range of $1\times10^{14}$ Ω-centimeter at 23° C. Example of materials having low dielectric constants, high electrical resistivity, and low magnetic permeability that may be used for portions of a housing that include a receive antenna configuration according to the examples described in this disclosure may include titanium alloy grade 5, 9, 23, 36, which may provide an adequate level of radio transmissivity at lower frequencies, such as up to 200K Hz, or ceramic material that may provide radio transmissivity at these lower frequencies and frequencies above the 200 k Hz frequency range, for example for frequency ranges up to 10 MHz. Metal ceramics made using a metal injection molding process may also be used for a wide range of frequencies similar to the operating frequency ranges for ceramics.

In order to allow higher frequency magnetic fields to penetrate the housing of device 30 and reach receive antenna 43, at least the antenna window 40 portion of the device may be formed of a material, such as sapphire, that has a high value for electrical resistivity, at least at temperatures normally experienced by devices after being implanted within a patient, e.g., temperatures normally not to exceed 39 to 40° C. on the exterior surface of the implanted device even for a brief period of time, that may occur when the device is being recharged. To allow use of higher frequency magnetic fields for the purpose of recharging device 30, antenna window 40 may be made of a radio transparent material having high electrical resistivity (e.g., in a range of $1\times10^{11}$ to $1\times10^{16}$ Ohms-centimeter) and a low magnetic permeability. A wide range of materials will satisfy these requirements, including examples such as sapphire, a glass material, or polymeric materials are typically employed having a dielectric constant ranging from about 1 to 12. Use of sapphire or a glass material for antenna window 40 may allow a higher frequency of an induced magnetic field to be transmitted through the antenna window 40 and be imposed on receive antenna 43 relative to other materials that may not provide a same level, or as high a value, for electrical resistivity. For example, by using an antenna window 40 made from sapphire, magnetic fields having frequencies ranging from about 100 KHz to 10 MHz may be imposed on device 30, wherein the sapphire allows the imposed magnetic field or fields having a frequency in this range to pass through the antenna window 40 and induce a current in an electrical conductor forming the windings of receive antenna 43.

The ability to use higher frequency magnetic fields allows for more energy, and thus a larger current, to be induced into the electrical conductor forming the windings of receive antenna 43 at any given time, or over a particular time period during which the higher frequencies are being imposed on device 30, as compared to using a lower frequency magnetic field. Antenna window 40 is not limited to being formed from a visually transparent material. Examples of material used to form antenna window 40 may include any type of material having a minimum value for electrical resistivity (e.g., a good electrical insulator with low dielectric constant value) and low magnetic permeability, and that meets other manufacturing requirements and complies with any other applicable regulatory requirements, such as biocompatibility requirements, for use in implantable medical devices.

In a similar manner as described above with respect to antenna 43, second antenna 44 (when provided as part of device 30) may also be positioned within and for example encircled by antenna window 40. Electrical currents may be induced into the electrical conductor forming the windings of second antenna 44 when the externally generated and applied magnetic field(s) are imposed on second antenna 44. In some examples, second antenna 44 is a uni-directional antenna that will have a maximum level of current generated in the electrical conductor forming the windings of the second antenna for a given level of magnetic field intensity when a direction of the magnetic field being imposed on the second antenna aligns with a normal axis of the second antenna. The normal axis is generally a line that is perpendicular to the plane or set of coplanar planes in which the windings forming the second antenna lie.

In some example, the positioning of the second antenna 44 and the directional orientation of the normal axis of second antenna 44 may be arranged to allow the normal axis of the second antenna to align with a direction of a magnetic field imposed on device 30 that otherwise provides a lower level of inductive coupling efficiency related to the orientation of receive antenna 43. As such, second antenna 44 may be able to provide a higher level of induced current to electronic circuitry 45 as would be provided based on the level of induced current that could be provided by receive antenna 43 alone for the particular orientation of the magnetic field being induced onto device 30 at any particular time. In other words, second antenna 44 is specifically orientated within device 30 to have a most efficient level of inductive coupling with magnetic fields having a magnetic field direction that do not necessarily provide some of the higher or the most efficient levels of inductive coupling efficiently with receive antenna 43. The combination of receive antenna 43 and second antenna 44 thus allows a wider range of orientations of the magnetic field directions for the magnetic fields imposed onto device 30 that still create some minimum level of current to be induced into the combination of the receive coils forming receive antenna 43 and second antenna 44.

Electronic circuitry 45 of device 30 that is coupled to each of receive antenna 43 and second antenna 44 may include devices (not shown in FIG. 2A) such as diodes or other type of rectifier circuitry that allows some level of induced currents generated in either of these receive antennas to be combined together while preventing any induced current generated in one of these receive antenna from cancelling out any current that might be induced into the other receive antenna. As such, regardless of the orientation of the device 30, or based on changes in the orientation of device 30 relative to a magnetic field being imposed onto device 30, some minimum level of induced current may be generated for the given level of the magnetic field intensity being imposed onto the device based on the combined levels of induced current provided by receive antenna 43 and second antenna 44.

As illustrated in FIG. 2A, first housing portion 31, (which may also be referred to as the "battery housing"), is sealingly coupled to antenna window 40 at a first seam 41. The antenna window 40 is sealingly coupled to the second housing portion 36 of device 30 at second seam 42. Antenna 43 may be positioned within the portion of device 30 that is encircled by the antenna window 40. The electronic circuitry 45 may be positioned within the portion of device 30 encircled by second housing portion 36. In some examples, one or more components of electronic circuitry 45 may also be positioned within some portion of interior cavity 53 to utilize the space provided by positioning receive antenna 43 around the perimeter of the inner surface of antenna window 40. End cap 34 may be sealingly coupled to the end of second housing portion 36 that is opposite the end of second housing portion 36 coupled to the antenna window 40.

Examples of antenna window 40 are not limited to being formed from a material that is different from the first housing portion 31 and/or different from the second housing portion 36. In some examples, the antenna window 40 and the second housing portion 36 may be formed of a same material, such as sapphire, that is a different material used to form the first housing portion 31. In some examples, the first housing portion 31 and the second housing portion 36 are formed of a same material, such as titanium or a titanium alloy, and may be formed as separate pieces sealingly joined together using the antenna window 40 as the coupling piece. In various examples, first housing portion 31, antenna window 40 and second housing portion 36 may be formed a biocompatible ceramic material.

As further described below, examples of receive antenna 43 may be configured as a multi-axis or multi-directional antenna. As such, the direction, e.g., the orientation of the imposed magnetic field or magnetic fields reaching receive antenna 43 may provide a minimum level of inductive coupling efficiently between the antenna and the magnetic field(s) regardless of or at least over a wide range of the relative orientations of device 30 and the direction of orientation of the imposed magnetic field(s). In order words, the receive antenna 43 itself may not be orientation specific relative to the specific orientation of the fields imposed on device 30 for the purpose of inductive power transfer that can be used for recharging of battery 39. For example, for some examples of a receive antenna configuration included within device 30, any angle of direction for a magnetic field imposed on device 30 may induce some level of current within receive antenna 43 for a given level of the magnetic field strength imposed on device 30, and thus also imposed on receive antenna 43. The specific angle of the magnetic field direction of the magnetic field imposed on the device in some examples may be irrelevant with respect to inducing a minimum level of current in receive antenna 43 for a given level of energy of the magnetic field or fields because of the multi-directional configuration of receive antenna 43.

In some examples, various other aspects of the device 30 itself, such as interference with the transmission of the magnetic field(s) created by first housing portion 31, and/or second housing portion 36, or for example by materials used to form certain portion of device 30 (e.g., a titanium material used to form a cover for battery 39), may result in a lower level of induced currents when the magnetic fields are imposed at certain angles relative to device 30 compared to other angles for imposing the magnetic field onto the device. For implantable medical devices where certain angles of the direction of the magnetic field being imposed onto the device may incur interference with the inductive coupling of the magnetic field with the multi-directional antenna of the device, some level of current or currents may still be induced into the receive antenna of the device, but may for example provide a lower level of induced current compared to other angles of direction of the magnetic field that may be imposed onto the device. In such instances, a feedback signal provided by the device having the multi-directional antenna and that is indicative of the level of induced current(s) being generated by the receive antenna may be used to reorient the direction of the magnetic fields imposed onto the device relative to the device. Based on monitoring the feedback signal, a different relative angle between the implanted device and the direction of the magnetic fields can be arranged, for example by moving the position of the recharging coil(s) providing the magnetic field and/or repositioning the patient relative to the transmit coil(s), and thus may provide a better level of inductive coupling between the magnetic field and the receive antenna(s) of the implanted device.

Based on the capability of receive antenna 43 to provide at least a minimum level of induced current from the receive antenna for a given power level of a magnetic field being imposed onto the receive antenna regardless of the angle of incidence (orientation) of the magnetic field within the bounds determined by other physical factors related to the device itself, a specific orientation or a narrowly limited range of orientations between receive antenna 43 and the direction of the incident magnetic field imposed onto receive antenna 43 is not required. The minimum current level may be induced into one or more of the receive coils of multi-directional receive antenna 43 regardless of the specific orientation of the incident magnetic field and the relative orientation of the receive antenna to those magnetic field(s). This feature is useful when performing a recharging operation on an implanted device that includes a multi-directional antenna within the device because a minimum level of recharging current can be induced into the receive antenna of the device without the need for an elaborate or complex alignment procedure to orient the magnetic fields to a particular orientation of the device and the receive antenna. For deeply implanted devices whose exact orientation may not be known, or whose position may have shifted, or may actually be shifting during a recharging session of the device, the feature of not having to determine this relative orientation precisely may allow less expensive, less complicated, and less time-consuming techniques to be used to efficiently recharging the power source located within the implanted device.

While examples of induced current as described above have been described with respect to recharging a power source located within the device, the receive antenna configurations and features of inductive power transfer to the device through current induced in the receive antenna(s) of the receive antenna configuration of an implanted device may also be applied when inducing a current into the receive antenna configuration for the purpose of providing electrical energy to directly power the operation of the implanted device itself, for example in a passive device that may only operate when powered by an external power source, and may not include a rechargeable power source such as a battery that can continue to power the device once the externally provided magnetic fields are no longer being imposed onto the device. One advantage of passive devices is that because a rechargeable power source is not required, the space normally occupied by such a rechargeable power source is not required, and may therefore allow further miniaturization with respect to the overall dimensions required for the housing of the device.

As shown in FIG. 2A, power source (battery) 39 occupies some portion of device 30, such as first housing portion 31. Receive antenna 43 is located within an interior space encircled by antenna window 40, and electronic circuitry 45 is located substantially within the interior space of device 30 formed by second housing portion 36. Examples of the arrangement of the components within the housing of device 30 are not limited to the arrangement as shown in FIG. 2A, and other arrangements of the devices and components included within device 30 are contemplated for use with the multi-directional receive antenna configurations described in this disclosure. For example, as shown in FIG. 2A receive antenna 43 is arranged proximate to an inner surface of antenna window 40. Second antenna 44, when provided, may be a planar antenna formed on a substrate, such as a ferrite sheet, and positioned in the center portion of the area forming interior cavity 53 that is encircled by antenna window 40. Electrical conductors may extend from the receive coils of the receive antenna or antennas, and are electrically coupled to the electronic circuitry 45, and/or to one or more terminals of battery 39.

In some examples of device 30, first housing portion 31, antenna window 40, and second housing portion 36 may not be separately formed pieces, but instead may be one piece formed from a same type of material, and sealingly coupled to end cap 34 to form the hermetically sealed housing for device 30. In such examples, antenna window 40 is not provided as a separate piece of material, and instead is considered to be formed of the same material forming the one piece of material forming the housing portions of device 30. Device 30 is not limited to a device having any particular shaped housing. As shown in FIG. 2A, device 30 has a generally circular cross-sectional shape along longitudinal axis 46 for any plane that is perpendicular to longitudinal axis 46 throughout the first housing portion 31, antenna window 40, and second housing portion 36. In some examples, the circular cross-sectional shape of device has a diameter of approximately six millimeters. However, device 30 is not limited to having a circular cross-sectional shape as described above, and portions of device 30 may have other shapes in cross-section relative to longitudinal axis 46, including a rounded square, a rounded rectangle, or an elliptical shape.

The shape of device 30 as shown in FIG. 2A may allow for device 30 to be delivered to an implant site, such as the interior portion of a chamber of the heart of a patient, through a tubular shaped delivery tool, such as a catheter. The desire to keep device 30 as small as possible to allow for such delivery and implant techniques while still providing an adequate level of functions and features and an acceptable level of on-board electrical power available from a power source such as battery 39 may limit the space available for the receive antenna(s) within the device itself. The receive coils and arrangements of the receive coils forming the receive antenna(s) as describe in this disclosure provide compact arrangements for receive antenna configurations that not only can be packaged into these miniature type implantable medical devices, but also still address many of the issues related to inductive coupling efficiency and orientation issues related to the directionality of the receive antenna(s) and the orientation of the devices during recharging procedures performed on the device following implantation of the device. Additional examples of multi-directional receive antenna configurations that may be provided as receive antenna 43, and additional antenna(s) such as second antenna 44 in implantable medicinal devices such as device 30, and systems and techniques to recharge these devices, are further illustrated and described below.

Figure 2B:
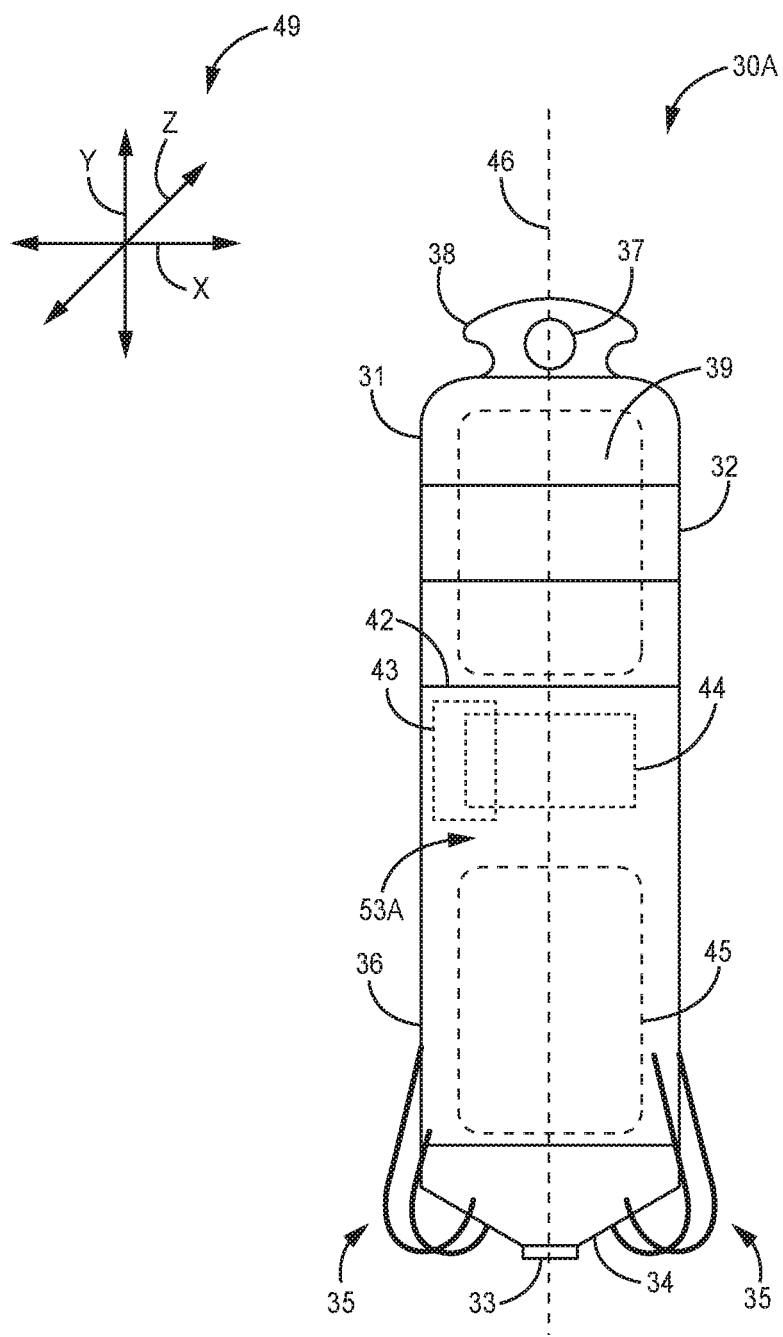
FIG. 2B is a conceptual drawing illustrating another example configuration of an implantable medical device according to various examples described in this disclosure.

FIG. 2B is a conceptual drawing illustrating another example configuration of an implantable medical device 30A according to various examples described in this disclosure. Implantable medical device 30A as illustrated in FIG. 2B includes the same or similar components as implantable medical device 30 as illustrated and described with respect to FIG. 2A, with the variations as described below for implantable medical device 30A. These same or similar components of implantable medical device 30A retain the same reference numbers that are used in identifying the corresponding components for implantable medical device 30 in FIG. 2A, with any exceptions as further described below.

As shown in FIG. 2B, implantable medical device 30A includes first housing portion 31 that at least partially encloses battery 39, and includes electrode 32, flange 38, and opening 37. Second housing portion 36 at least partially encloses electronic circuitry 45, and is coupled at one end of the second housing portion to end cap 34. End cap 34 includes electrode 33, and fixation mechanisms 35. As shown in FIG. 2B, the end of second housing portion 36 opposite the end cap 34 is "sealingly coupled" directly to the end of first housing portion 31 opposite flange 38 at seam 42 and without the use of an intervening and separate piece of material forming an antenna window, such as antenna window 40 as illustrated and described with respect to implantable medical device 30 and FIG. 2A.

As shown in FIG. 2B, receive antenna 43 is at least partially enclosed by a portion of the second housing portion 36 forming interior cavity 53A. In addition, in examples of implantable medical device 30A where second antenna 44 is provided, the second receive antenna may also be positioned relative to receive antenna 43 to be at least partially enclosed by second housing portion 36. As illustrated in FIG. 2B, the interior cavity 53A of implantable medical device 30A where receive antenna 43 is located (and second antenna 44 when provided) is positioned within and at least partially enclosed by second housing portion 36, and some remaining portion of the second housing portion 36 at least partially encloses the electronic circuitry 45. As such, second housing portion 36 is formed from a material, such as sapphire as described above, that allows energy in the form of a magnetic field imposed onto implantable medical device 30A from a source external to device 30A to pass through second housing portion 36 and be imposed onto the receive antenna(s) included within the interior cavity 53A of second housing portion 36.

Second housing portion 36 is not limited to being formed of any particular material, and may be formed of any type of material or materials that allow passage of magnetic fields through the second housing portion at the frequency or within a range of frequencies and at with the levels of intensity that are required to generate induced currents into the receive antenna(s) positioned within interior cavity 53A. In addition to examples using sapphire, in other examples second housing portion 36 may be formed from a biocompatible ceramic material or a glass material, which still allowing higher frequency (e.g., 100 kHz to 10 MHz) magnetic fields to pass through the second housing portion and be imposed onto the receive coils such as receive antenna 43 and/or second antenna 44. For more low frequency applications (e.g., magnetic fields having a frequency of 200 kHz or less), second housing portion may be formed of material that includes a titanium alloy that allow magnetic fields having these lower frequencies to pass through the second housing portion and be imposed onto the receive coils such as receive antenna 43 and/or second antenna 44.

Seam 42 is used to "sealingly couple" second housing portion 36 to first housing portion so that first housing portion 31, second housing portion 36, and end cap 34 form a hermetically sealed housing for the components included within implantable medical device 30A. Seam 42 is not limited to any particular type of seam formed using any particular technique for forming the seam, and may include any type of seam appropriate for joining together the types of material(s) used to form first housing portion 31 and second housing portion 36. In some examples, by not using a separate antenna window section in forming the housing for implantable medical device 30A (compared for example to implantable medical device 30 of FIG. 2A that includes antenna window 40), the overall length dimension of implantable medical device 30A along longitudinal axis 46 may be reduced. The smaller longitudinal dimension of implantable medical device 30A may provide advantages with respect to smaller spaces where the device may be implanted into, and/or with respect to the lessening of the impact on the flow of fluids, such as blood flows, around and in the area of a patient where the device is implanted.

For several of the examples of receive antenna configuration including one or more receive coils positioned within an implantable medical device as described throughout the remainder of this disclosure, the receive antenna(s) are described as being positioned within, partially enclosed by, and/or affixed to an antenna window such as antenna window 40 of implantable medical device 30 of FIG. 2A. However, unless specifically described otherwise, any of these receive antenna configurations and any equivalents thereof may be provided within interior cavity 53A and at least partially enclosed within second housing portion 36 of an implantable medical device arranged in a same or similar manner as described above with respect to implantable medical device 30A as illustrated and described with respect to FIG. 2B.

Figure 3A:
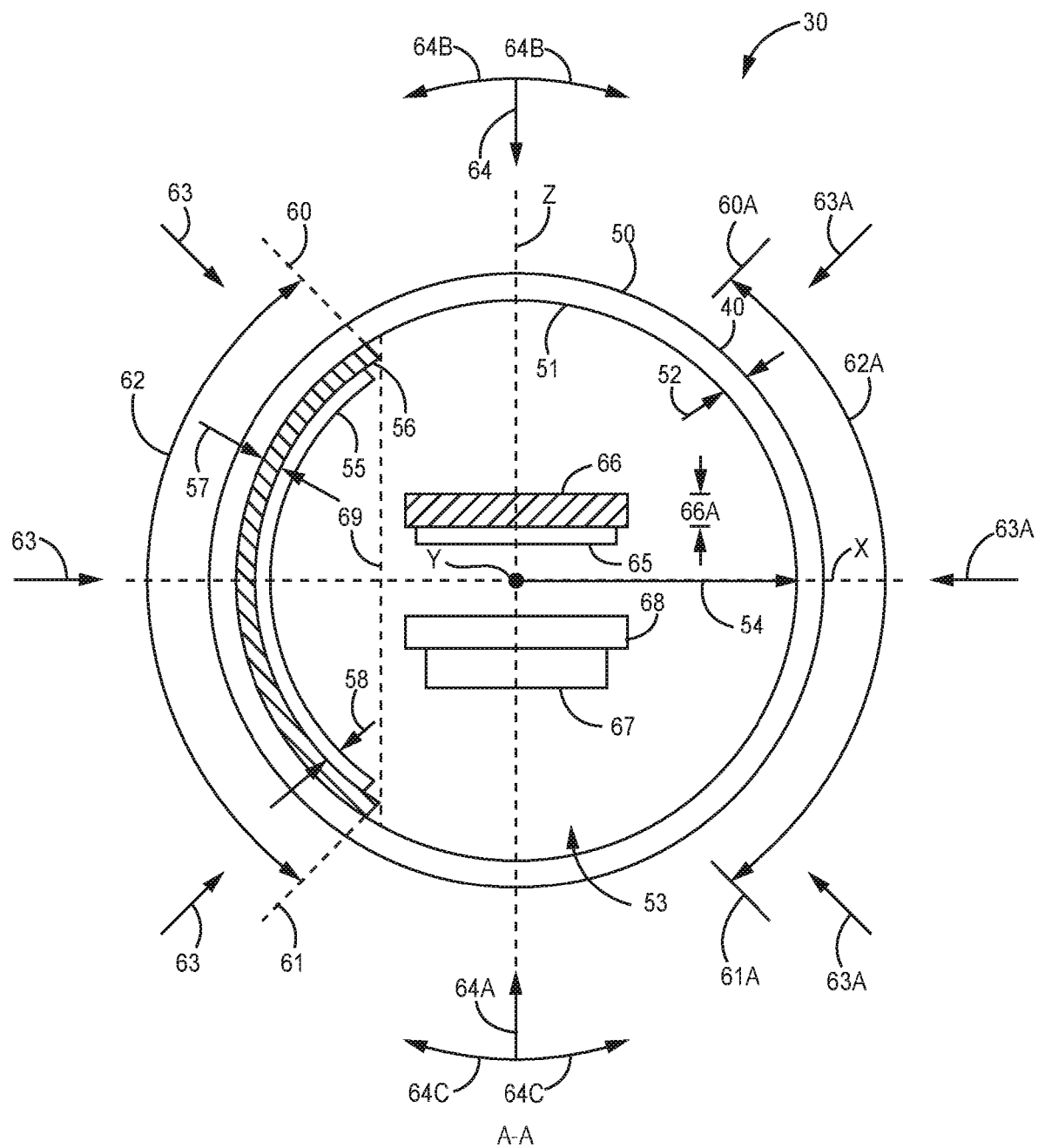
FIG. 3A is cross-sectional view of a receive antenna configuration for the implantable medical device of FIGS. 2A-2B according to various examples described in this disclosure.

FIG. 3A is a cross-sectional view A-A of a receive antenna configuration for the implantable medical device 30 of FIG. 2A according to various examples described in this disclosure. Although described with respect to device 30 having an antenna window 40, the receive antenna configuration(s) as described below with respect to FIG. 3A may also be provided in a device that does not include a separate antenna window as part of the housing of the device, such as device 30A as illustrated and described with respect to FIG. 2B. For example, the receive antenna(s) described below with respect to FIG. 3A may be affixed to and/or positioned within a portion of the second housing portion 36 as illustrated and described above with respect to FIG. 2B.

The cross-sectional view A-A in FIG. 3A is viewed from the perspective of a plane cutting through device 30 at a midpoint of antenna window 40 along the longitudinal axis 46 of device 30, wherein longitudinal axis is perpendicular to the plane cutting through the device. In cross-sectional view A-A as illustrated in FIG. 3A, device 30 is illustrated looking in a same direction as the direction of orientation of the Y-axis, with the X-axis extending in a left-right (horizontal) orientation, and the Z-axis extending in an up-down (vertical) orientation in the view. As shown in FIG. 3A, antenna window 40 includes an outer surface 50 having a circular shape in cross-section, an inner surface 51 also having a circular shape in cross-section positioned within the outer surface 50 so that antenna window 40 has a wall thickness 52 that encircles the Y-axis (and longitudinal axis 46) of device 30, encircling and at least partially enclosing a cylindrical shaped interior cavity 53. A dimensional value for wall thickness 52 may be in a range of 0.15 to 0.5 millimeters. A dimensional value for a radius 54 extending from a center point at the Y-axis of interior cavity 53 to the inner surface 51 may be in a range of 2 to 10 millimeters. Antenna window 40 may extend along and encircle the Y-axis so that the interior cavity 53 extends along the Y-axis (longitudinal axis 46) and within the inner surface 51 forming an upright cylindrical shape having a height corresponding to longitudinal dimension 47 as shown in FIG. 2A.

Figure 10:
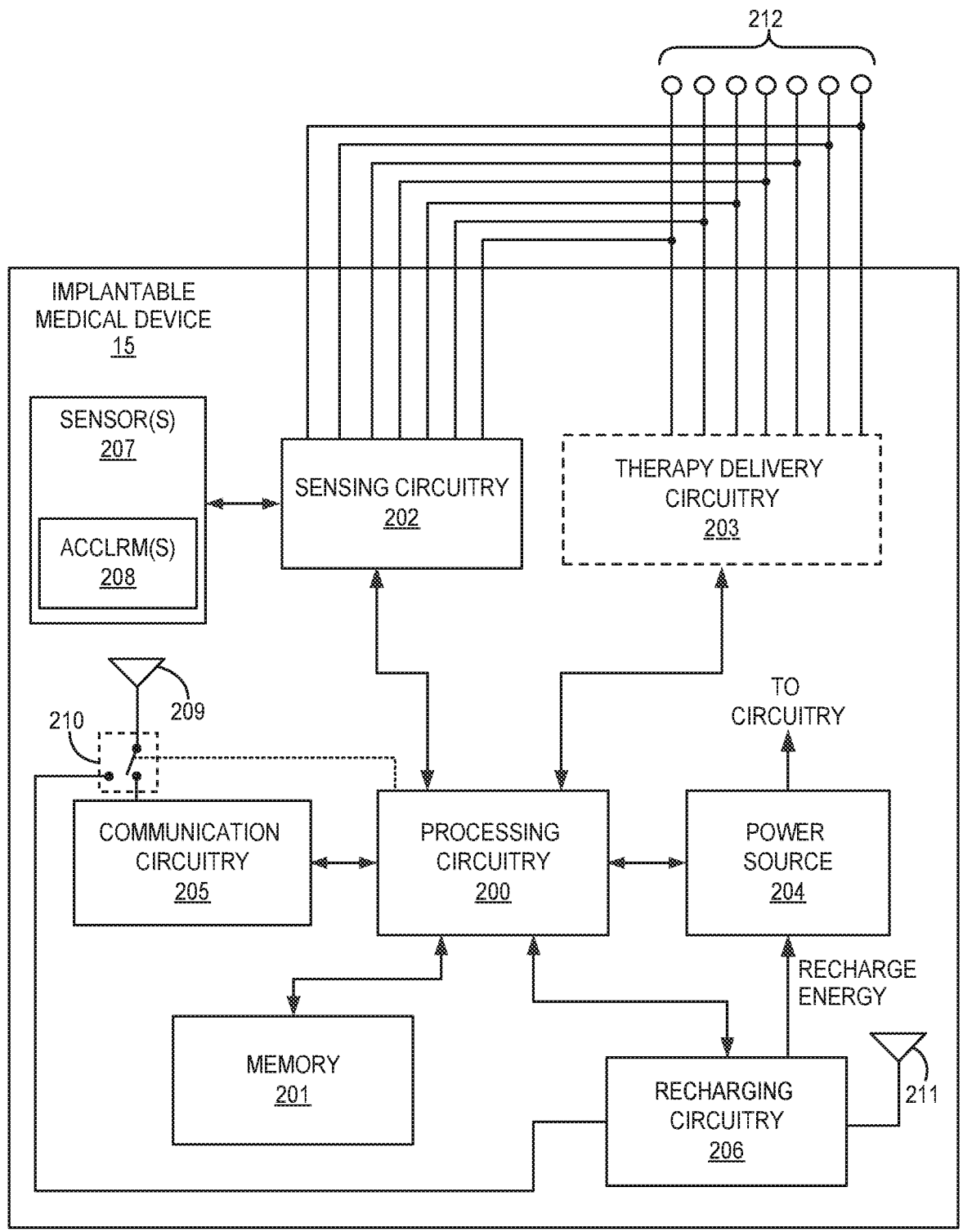
FIG. 10 is a functional block diagram illustrating an intracardiac pacing device according to various examples described in this disclosure.

Referring again to FIG. 3A, one or more receive coils forming the receive antennas of device 30 may be positioned within the interior cavity 53 of antenna window 40. For example, receive coil 55 may be positioned adjacent a portion of inner surface 51 of antenna window 40. Receive coil 55 may be electrically coupled to recharging circuitry of device 30 (not shown in FIG. 3A, but for example recharging circuitry 206 as shown in FIG. 10), and configured to have a current induced into the coil winding of the receive antenna when a magnetic field or magnetic fields is/are imposed onto the receive antenna. The magnetic field(s) imposed onto receive coil 55 may be generated by external recharging circuitry (not shown in FIG. 3A, but for example external recharging circuitry 231 in FIG. 12) and transmitted by a recharging coil (not shown in FIG. 3A, but for example recharging coil 232 and/or recharging coil pair 232, 233 of FIG. 12) for the purpose of inducing a recharging current into the coil winding of receive coil 55. Receive coil 55 may be formed of an electrical conductor, such as a wire or a multi-strand electrical conductor, shaped to form a coil winding, with electrical connections (not shown in FIG. 3A) electrically coupled to each end, respectively, of the electrical conductor forming the receive coil. Examples of a coil winding that may be used to form receive coil 55 in the configuration illustrated in FIG. 3A include coil winding 70 as illustrated and described with respect to FIGS. 4A-4B, and the single loop receive coil 90 as illustrated and described with respect to FIG. 5A. The electrical current induced in the coil windings of receive coil 55 may be provided to recharging circuitry of device 30 for the purpose of electrically recharging an electrical power source located within or electrically coupled to device 30, as further described below.

As shown in FIG. 3A, receive coil 55 is positioned on a ferrite sheet 56 so that a curved shape of receive coil 55 conforms to the curved shape of ferrite sheet 56. The curved shape of receive coil 55 and ferrite sheet 56 conforms to a curvature of the inner surface 51 of antenna window 40 over an angular range 62 extending around inner surface 51 from first radial position 60 to second radial position 61. First radial position 60 is separated from second radial position 61 along the inner surface 51 by some angular value for angular range 62. The angular value for angular range 62 may be in a range of 30 to 180 degrees. As shown in FIG. 3A, a first side of ferrite sheet 56 is affixed to inner surface 51 of the antenna window 40 along the portion of inner surface 51 extending between first radial position 60 and second radial position 61. Ferrite sheet 56 may also have a height dimension 48 (FIG. 2A) extending in a direction corresponding to the orientation of the Y-axis (e.g., looking into and extending out of the drawing sheet in FIG. 3A). As shown in FIG. 3A, receive coil 55 is positioned adjacent to a second side of ferrite sheet 56, the second side of ferrite sheet 56 opposite the first side of the ferrite sheet and separated from the first side of the ferrite sheet by a thickness dimension 57 of ferrite sheet 56. The dimensional value for thickness dimension 57 of ferrite sheet 56 may be in a range from 0.01 to 5 millimeters.

Further, the material used to form the ferrite sheets is not limited to a particular type of material, and in some examples, is a ferrite material comprising a compound that includes iron oxides, and may be combined with nickel, zinc, and or manganese compounds. The ferrite material may be referred to as a "soft ferrites" that has low coercivity (magnetization in the material can be easily reversed in direction without generated large levels of hysteresis losses) and having high resistivity, which helps reduce eddy current flowing in the material. The ferrite sheets may include one or more layers of material, including a polyethylene terephthalate (PET) layer as a first surface of the ferrite sheet and an adhesive layer of a second surface of the ferrite sheet opposite the first surface.

The electrical conductor forming receive coil 55 may be arranged so that each of the individual windings of the electrical conductor forming receive coil 55 lie within a same curved-planar area having a thickness dimension 58 that extends across the entirety of the area occupied by the coil windings. In some examples, the thickness dimension 58 may be the thickness value for the electrical conductors itself, for example a cross-sectional diameter of the electrical conductor used to form the windings of received coil 55. In some examples, portions of the windings of the electrical conductor used to form receive coil 55 may cross or overlap with one another, and at these portions of receive coil 55 the thickness dimension 58 may be greater than the thickness dimension at other portion of the receive antenna. For example, the thickness dimension 58 at a portion of receive coil were the electrical conductors cross or overlap may be equal or slightly greater than the thickness of each of the overlapping electrical conductors combined together. In other examples, the windings of the electrical conductor used to form receive coil 55 may include multiple layers of winding that are stacked one on top of the other in a direction that extends away from the ferrite sheet 56. When the electrical conductors forming receive coil 55 are stacked one on top of another, the thickness dimension 58 of the receive coil 55 may be have a dimensional value approximately equal to a thickness of the individual windings combined together.

Regardless of the actual dimensional value of thickness 58 across the area occupied by the windings forming receive coil 55, the contour of the windings conforms to the contour of the ferrite sheet 56, and thus to the contour of inner surface 51 of the antenna window 40 over angular range 62, and extending in a direction corresponding to the Y-axis (and longitudinal axis 46) of device 30 over the height dimension 48 (FIG. 2A). In examples where receive coil 55 is affixed to ferrite sheet 56, the outer-most winding of the electrical conductor forming the receive antenna may extend to a position that is slightly less than the outside edges of ferrite sheet 56. For example, as shown in FIG. 3A the upper-most portion of ferrite sheet 56 near first radial position 60 extends slightly further along the inner surface 51 of the antenna window 40 relative to the upper-most portion of receive coil 55 that is closest to the first radial position 60. Similarly, the lower portion of ferrite sheet 56 near second radial position 61 extends slightly further along the inner surface 51 of the antenna window 40 relative to the lower portion of the receive coil 55 that is closest to the second radial position 61. In addition, the outer-most extensions of the windings forming the receive coil 55 with respect to the Y-axis (e.g., longitudinal axis 46) of device 30 may extend in the direction of height dimension 48 (FIG. 2A) to distances slightly less than the corresponding dimensions for ferrite sheet 56, thus maintaining these portions of receive coil 55 within the area defined by the second surface of the ferrite sheet 56 to which the windings forming receive coil 55 are affixed.

Based on the configuration of receive coil 55 as shown in FIG. 3A, the electrical conductor forming the windings of the receive antenna may provide a minimum level of inductively coupled current for a given level of magnetic field intensity induced by a magnetic field(s) imposed on the receive coil having a wide variation of magnetic field directions. For example, receive coil 55 may provide a high level of inductive coupling, and thus provide a minimum level of induced current generated in the receive coil for a given level of magnetic field intensity, when the magnetic field imposed onto the receive coil has any of the magnetic field directions indicated by arrows 63 in FIG. 3A. As shown in FIG. 3A, the magnetic field directions may include magnetic fields having an orientation directed toward the Y-axis of device 30, and an angular orientation extending anywhere between first radial position 60 and second radial position 61.

As shown in FIG. 3A, any magnetic field imposed on receive coil 55 having a magnetic field direction that is coplanar with a plane including the X and Z-axes of device 30 at antenna window 40 and an angular orientation between first radial position 60 and second radial position 61 will provide a minimum level of inductive coupling efficiency between the imposed magnetic field and the receive coil 55. In other words, at least in part due to the curved configuration of receive coil 55, receive coil 55 is not uni-directional with respect to coupling efficiencies with magnetic field(s) imposed on the receive coil, and may provide a same or similar level of inductive coupling efficiency with magnetic field(s) imposed onto the receive coil over a range of relative orientations for the magnetic fields illustratively represented as by arrows 63.

In addition to magnetic fields having a magnetic field direction that is coplanar with the X and Z-axes as described above, receive coil 55 may also provide a same or similar level of inductive coupling efficiency with magnetic fields having a magnetic field direction relative to device 30 that is not coplanar with the X and Z-axes of the device. For example, magnetic fields having a magnetic field direction that is not perpendicular to the Y-axis (longitudinal axis) and that intersects a plane including both the X-axis and Z-axis of the device at some angle other than zero degrees may also provide a same or similar level of inductive coupling efficiency between magnetic fields and receive coil 55 compared to the levels of inductive coupling efficiencies achieved for the coplanar magnetic fields represented by arrows 63. For the more extreme angles of incidence of the magnetic field directions, for example that intersect the plane of the X-axis and Z-axis at an angle that exceeds for example a 45 degree angle above the plane, the level of coupling efficiency may be reduced to a level that is less than that which could be achieved for a magnetic field having a magnetic field direction within the range indicated by arrows 63 but that is also perpendicular to the Y-axis.

In some examples, the angle of incidence of the magnetic field direction may include angle of incidence that are perpendicular to the plane including both the X-axis and the Z-axis of device 30, e.g., angles of incidence for the magnetic fields that are collinear with the orientation of the Y-axis (longitudinal axis 46) of device 30. For some of these non-coplanar angles of orientation between the magnetic fields and device 30, portions of device 30, such as first housing portion 31, second housing portion 36, and or end cap 34 as illustrated in FIG. 2A may reduce the overall level of inductive coupling efficiency for angles of orientation between the magnetic fields and receive coil 55 at some of the larger angles of incidence, e.g., angles of incidence that are more closely aligned with the Y-axis (longitudinal axis) of device 30.

As described above, the magnetic fields represented by arrows 63, and the variations in the angles of incidence of these magnetic fields as described above, are generally directed toward device 30 from the external areas to the left side of the device as shown in FIG. 3A. As such, the direction of the magnetic fields may pass through ferrite sheet 56 before reaching receive coil 55. The positioning of the ferrite sheet 56 on the side of receive coil 55 as shown in FIG. 3A causes the overall level of inductive coupling between the magnetic field and receive coil 55 to be larger than would be achieved without the presence of the ferrite sheet for a same magnetic field intensity. In addition, magnetic fields having a magnetic field direction that cause the magnetic fields to be imposed on receive coil 55 without first passing through ferrite sheet 56 may still induce a similar level of current into the coil winding of receive coil 55.

For example, as shown in FIG. 3A a range of angles of incidence for magnetic fields having magnetic field directions extending between a third radial position 60A and a fourth radial position within an angular range 62A as shown in FIG. 3A may also be imposed onto receive coil 55. The third radial position 60A, fourth radial position 61A, and angular range 62A may represent a mirror image of first radial position 60, second radial position 61, and angular range 62, but arranged on the opposite side (right hand side in FIG. 3A) of the Z-axis relative to these corresponding elements. In addition to angles of orientation for the magnetic fields represented by arrow 63A that may lie in the plane that includes both the X-axis and the Z-axis, other angles of incidence that are not perpendicular to the Y-axis, as describe above with respect to arrows 63, may also be provided as the magnetic field directions represented by arrows 63A.

Because the variations in the angles of incidence represented by arrows 63A may not pass through the ferrite sheet 56 before being imposed onto receive coil 55, the overall level of inductive coupling achieved for a given level of magnetic field intensity may be less than would be achieved for a same level of magnetic field intensity having a corresponding but opposite magnetic field direction represented by arrows 63. For some directions of imposed magnetic fields, such as magnetic fields having a direction illustratively represented by arrow 64 and/or arrow 64A, a lower level or no level of induced current may be generated in the coil winding forming receive coil 55. However, a high or sufficient level of inductive coupling efficiency may still be achieved between receive coil 55 and magnetic fields having a magnetic field direction represented by arrows 63A, thus further increasing the overall range of magnetic field directions that may be imposed on device 30 and result in a sufficient level of inductive coupling between the device and the magnetic field(s) to provide efficient recharging of a rechargeable power source located within the device. This feature further reduces the need for achieving a specific orientation, or a narrow range of relative orientations, between the receive antenna of device 30 and the direction of the magnetic fields imposed onto the device, while still achieving a sufficient level of inductive coupling efficiency during a recharging session being performed on the device.

In some examples of device 30, an additional or second receive coil 65 is also positioned within interior cavity 53. As shown in FIG. 3A, receive coil 65 may be a flat or spiral-wound planar antenna. Receive coil 65 may be a uni-directional antenna having a normal axis with an orientation that corresponds to the orientation of the Z-axis of device 30, and having windings that lie in a plane or a set of coplanar planes that are coplanar with a plane that includes both the X-axis and the Y-axis of device 30. As shown in FIG. 3A, receive coil 65 may be positioned at some distance offset relative to the center point of the interior cavity 53. In addition, the coil windings forming receive coil 65 may extend at least partially into an area of interior cavity that lies to the left-hand side of an arc 69 drawn between the first radial position 60 and the second radial position 61. The scale, positioning, and relative spacing between receive coils 65 and 55 as shown in FIG. 3A is intended as a non-limiting example, and other sizes and type of coil configurations for receive coil 65, and alternative physical positionings of receive coil 65 within interior cavity 53 are possible and are contemplated by the examples of device 30 as described in this disclosure.

As shown in FIG. 3A, receive coil 65 may be affixed to a ferrite sheet 66 on a side of receive coil 65 that faces the upper portion of the view in FIG. 3. In various examples, ferrite sheet 66 may include a thickness dimension 66A for the ferrite sheet have a thickness in a range from 0.01 to 5 millimeters. In other examples, receive coil 65 may be affixed to some other type of substrate, such as a circuit board or other type of insulative material. In still other examples, the coil windings of receive coil 65 are not affixed to any type of additional sheet or substrate, and are self-supported within interior cavity 53. As shown in FIG. 3A, a magnetic field having a magnetic field direction illustratively represented by arrow 64 that is perpendicular to the Y-axis (longitudinal axis) and aligned with the orientation of the Z-axis also aligns with the normal axis of receive coil 65. In addition, these same magnetic fields having the magnetic field direction illustrated by arrow 64 would pass through the ferrite sheet 66 before being impose onto receive coil 65. Because of the alignment between the orientation of arrow 64 and the normal axis of receive coil 65, a high level of inductive coupling efficiency may be achieved between the magnetic fields having a magnetic field direction indicated by arrow 64 and receive coil 65. The placement of ferrite sheet 66, when provided, may further enhance the level of inductive coupling efficiency achieved between the between the magnetic fields having a magnetic field direction indicated by arrow 64 and receive coil 65.

Variations in the orientation of the magnetic field direction illustrate by arrow 64 relative to the radial orientation of the magnetic field direction while maintaining a perpendicular orientation relative to the Y-axis is illustratively represented by arrows 64B. Additional variations in the orientation of the magnetic field direction illustrated by arrow 64 may also occur relative arrow 64 having a non-perpendicular orientation relative to the Y-axis, and intersecting a plane that includes both the X-axis and the Z-axis at some non-zero angle. These variations in the relative orientation of the direction of the magnetic field represented by arrows 64B, while potentially reducing the level of the inductive coupling efficiency begin achieved between the magnetic field and receive coil 65, may still provide some level of inductive coupling, and therefore some level of induced current in receive coil 65.

In a similar manner, magnetic fields having a magnetic field direction illustratively represented by arrow 64A that is perpendicular to the Y-axis (longitudinal axis) and aligned with the orientation of the Z-axis of device 30 also aligns with the normal axis of receive coil 65. While these same magnetic fields having the magnetic field direction illustrated by arrow 64A would not pass through the ferrite sheet 66 before being impose onto receive coil 65, the magnetic fields may provide a high level of inductive coupling efficiency between the magnetic fields having a magnetic field direction indicated by arrow 64A and receive coil 65. Variations in the direction of orientation of the magnetic fields as represented by arrows 64C, and variations in the direction of orientation of arrow 64A that may include orientations that are not perpendicular to the Y-axis or a plane including both the X-axis and the Z-axis may still provide some level of inductive coupling, and therefore some level of induced current in receive coil 65.

As shown in FIG. 3A, the placement and orientation of a second receive antenna in the interior cavity 53 of device 30 may provide a level of inductive coupling between magnetic fields having the orientations as describe above with respect to arrows 64, 64A and variations thereof that may not necessarily be the better orientations with respect to inductive coupling efficiency with receive coil 55. As such, the range of variations in the directions of magnetic fields that provide some minimum level of induced current for a given level of magnetic field intensity may be increased while still maintaining a compact arrangement of the receive antennas within device 30. The compact arrangement having this wide range of angles over which a high level of inductive coupling efficiency can be achieved is especially useful for allowing efficient and safe recharging of a power source included with a small implanted medical device such as device 30, in particular when the orientation of the is unknown or is not necessarily maintained in a constant orientation. The same benefits also apply when imposing a magnetic field onto a device, such as device 30, for the purpose of powering the operation of the device from the current(s) induced into the receive antenna(s). The use of just two receive coil winding forming receive coils 55 and 65 also reduces to two sets the number of components required to provide rectification and summing of the current (s) that may be induced into these coils during a recharging session being performed on device 30, thus minimizing the amount of space and circuit real estate required to perform these functions. Further, the receive antenna configuration as illustrated in FIG. 3A including the curved shape of receive coil 55 allows the receive antenna configuration of the device to be packaged within a device having for example a circular cross-section, at least for example at the portion of the device comprising antenna window 40, so that that the device may be advanced through and/or implanted using a tubular shaped delivery tool, such as a catheter.

In various example of device 30, receive coil 55 and/or second receive coil 65 may also be configured to operate as a telemetry antenna to allow wireless communication signals to be transmitted from and received by the antenna(s) of the implanted device. In various examples, device 30 includes a separate telemetry antenna 67 as shown in FIG. 3A. Telemetry antenna 67 may be positioned within interior cavity 53 and encircled by antenna window 40 to allow for the wireless communication signals transmitted between device 30 and one or more external devices (not shown in FIG. 3A, but for example external device 11 and/or transceiver 16 shown in FIG. 1). Telemetry antenna 67 may be coupled to a substrate 68, such as a circuit board or a ceramic substrate, or in the alternative may be configured as a self-supported structure.

Figure 3B:
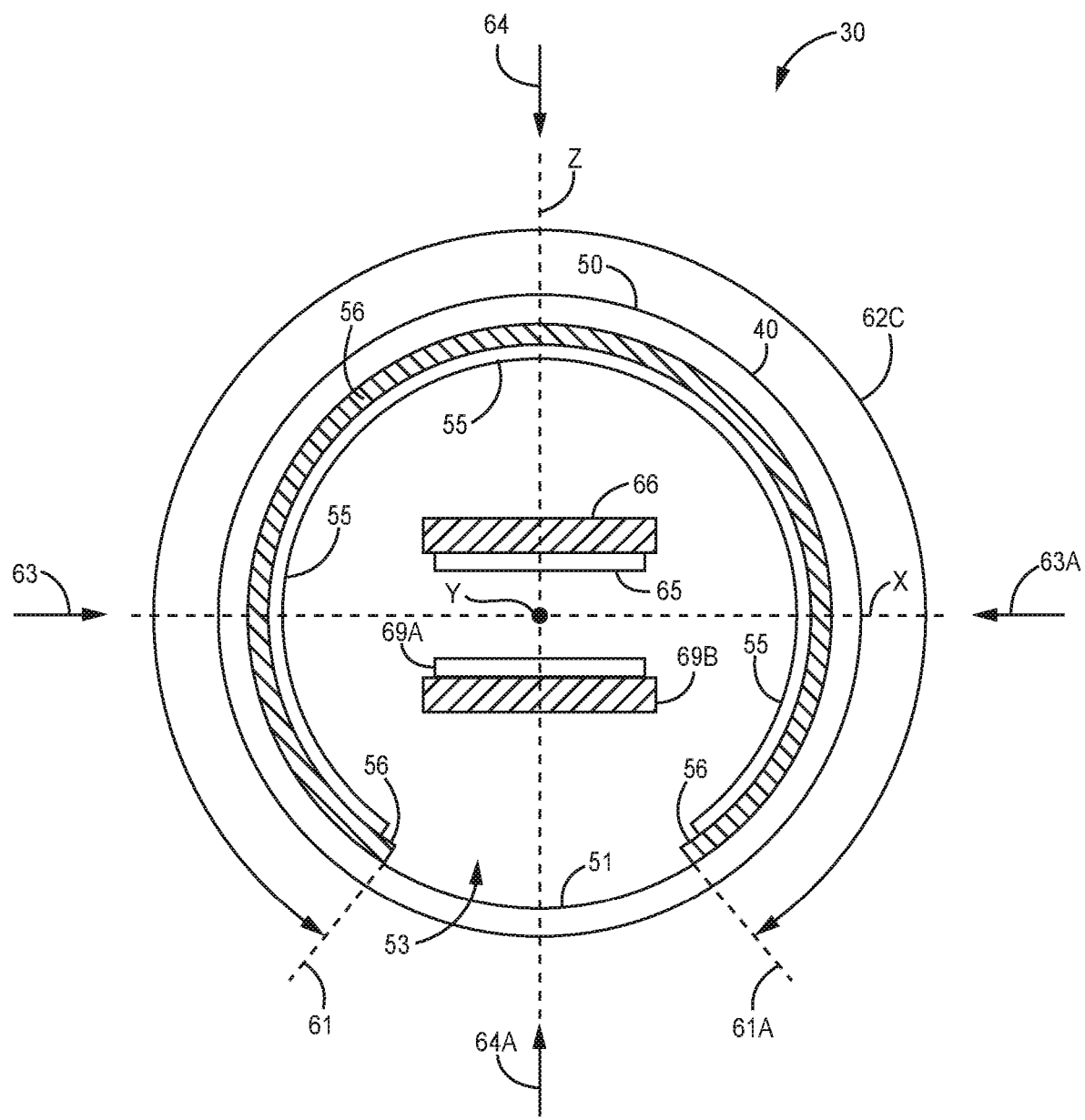
FIG. 3B is another cross-sectional view of a receive antenna configuration for the implantable medical devices of FIGS. 2A-2B according to various examples described in this disclosure.

FIG. 3B is another cross-sectional view of a receive antenna configuration for the implantable medical device 30 of FIG. 2A according to various examples described in this disclosure. The example of implantable medical device 30 as illustrated and described with respect to FIG. 3B may including any of the examples and variations of the implantable medical device(s) illustrated and described above with respect to FIG. 3A, but with the variations as described below for FIG. 3B. Further, although described with respect to device 30 having an antenna window 40, the receive antenna configuration(s) as described below with respect to FIG. 3B may also be provided in a device that does not include a separate antenna window as part of the housing of the device, such as device 30A as illustrated and described with respect to FIG. 2B. For example, the receive antenna(s) described below with respect to FIG. 3B may be affixed to and/or positioned within a portion of the second housing portion 36 as illustrated and described above with respect to FIG. 2B.

As shown in FIG. 3B, device 30 includes a ferrite sheet 56 affixed to a portion of inner surface 51 of antenna window 40, and receive coil 55 affixed to a surface of ferrite sheet 56 opposite the surface of ferrite sheet 56 affixed to inner surface 51. In comparison to the example of the ferrite sheet and receive coil 55 as shown in FIG. 3A, the ferrite sheet and receive coil as shown in FIG. 3B extend around a much larger angular range 62C of inner surface 51 as compared to the angular range 62 illustrated in FIG. 3A. The angular value for angular range 62C may be in a range of 180 to 360 degrees. Further, examples of a coil winding that may be used to form receive coil 55 as show in FIG. 3B include the infinity shaped coil winding 90 as shown in FIGS. 5B-5C and the dual-winding coil configuration 102 as shown in FIG. 5D. The electrical current induced in the coil windings of receive coil 55 may be provided to recharging circuitry of device 30 for the purpose of electrically recharging an electrical power source located within or electrically coupled to device 30, as further described below.

As shown in FIG. 3B, ferrite sheet 56 extends along inner surface 51 from second radial position 61 to fourth radial position 61A. Receive coil 55 extends along the surface of ferrite sheet 56 opposite the surface of ferrite sheet 56 that is affixed to inner surface 31 of antenna window 40, and over an angular range in some examples is equal to or slightly less than angular range 62C of the ferrite sheet. The extension of the infinity shaped coil winding or the dual-winding coil configurations used to form receive coil 55 places the loops of these coil winding in different planes relative to one another, and thus allow magnetic fields imposed on ether loop of the coil to provide a current flow to be generated in the coil windings that may be used to recharge a power source of the device, and/or to power the operation of the device. As shown in FIG. 3B, the arrangement of the ferrite sheet 56 positioned between antenna window 40 and the receive coil 55 may provide the "preferred orientation" for the ferrite sheet/receive coil assembly shown in FIG. 3B relative to magnetic fields having magnetic field directions over the range indicated by angular range 62C, which in some example may extend around the entire inner surface 51 for 360 degrees encircling the Y-axis. This may include magnetic fields having magnetic field directions that may be perpendicular and/or non-perpendicular to the Y-axis of device 30 over angular range 62C as illustratively represented by arrows 63, 64, and 63A.

In the example illustrated in FIG. 3B, the coil winding forming receive coil 55 may be formed as an infinity shaped coil winding or a dual-winding coil configuration, and having a longitudinal axis formed in a curved shape to conforming to the curvature of the surface of the ferrite sheet to which the receive coil is affixed. As such, the "preferred orientation" of the ferrite sheet receive coil assembly including receive coil 55 may extend over the entirety of the angular range 62C. The benefits attributed to the increased level of magnetic field coupling efficiency imparted to the assembly by use of the ferrite sheet 56 may therefore be achieve over a wide range of magnetic field directions for magnetic fields imposed on the receive antenna configuration of device 30 as illustrated in FIG. 3B.

As further illustrated in FIG. 3B, examples of device 30 having the ferrite sheet 56 and reeve coil 55 arrangement extending over angular range 62C may also include one or more additional receive coils, which may also be affixed to ferrite sheet(s), and coupled to the recharging circuitry of the device 30 to further enhance the level of inductive coupling efficiency achieved by imposing magnetic field(s) onto the device. For example, an additional receive coil 69A that is affixed to a ferrite sheet 69B may be positioned within the interior cavity 53 of device 30 as shown in FIG. 3B. Receive coil 69A may be a flat spiral-wound coil in some examples. Because the ferrite sheet 69B is affixed to the side of receive coil 69A facing the bottom portion of device 30 as illustrated in FIG. 3B, ferrite sheet 69B and receive coil 69A may be considered to have a "preferred orientation" that favors inductive coupling with magnetic fields having a magnetic field direction directed toward the bottom side of device 30, as illustratively represented by arrow 64A. Because this bottom portion of the device 30 may include an area not necessarily within angular range 62C, and thus an area not necessarily providing a preferred orientation relative to receive coil 55, the addition of ferrite sheet 69B and receive coil 69A may enhance the overall level of electrical current(s) that are induced into a receive antenna configuration of device 30 by magnetic feels having for example a magnetic field orientation that are outside the angular range 62C. The addition of the receive coil 69A may thus increase the variation of the orientations of the directions of magnetic fields that may be imposed onto device and still provide a minimum level of induced current(s) into the receive antenna configuration of the device.

As shown in FIG. 3B, some examples of device 30 include a receive coil 65 affixed to a ferrite sheet 66 provided in addition to or instead of, ferrite sheet 69B and receive coil 69A in device 30. Receive coil may be formed as a flat spiral-wound coil in some examples. Ferrite sheet 66 and receive coil 65 as illustrated have a "preferred orientation" that favors inductive coupling with magnetic fields having a magnetic field direction directed toward the upper side portion of device 30 in FIG. 3B as illustratively represented by arrow 64. The addition of the receive coil 65 may further increase the variations of the orientation(s) for the direction(s) of magnetic fields that may be imposed onto device 30 and still provide a minimum level of induced current(s) into the receive antenna configuration of the device.

Ferrite sheets 56, 66, and 69B as illustrated in FIG. 3B may be formed from a material or material(s) described above for ferrite sheets, including a compound of iron oxide that may or may not be mixed with some other metal or compound. In some examples, one or more of these ferrite sheets may comprise a flexible material that may be bent or otherwise formed into some non-planar shape for the sheet. In some examples, one or more of receive coils 55, 65, and 69A may also operate as telemetry antenna(s) to provide wireless communications to and from device 30. In other examples, a separate telemetry antenna (not shown in FIG. 3B) in including in device 30 in addition to the receive coils illustrated in FIG. 3B.

Figure 4A:
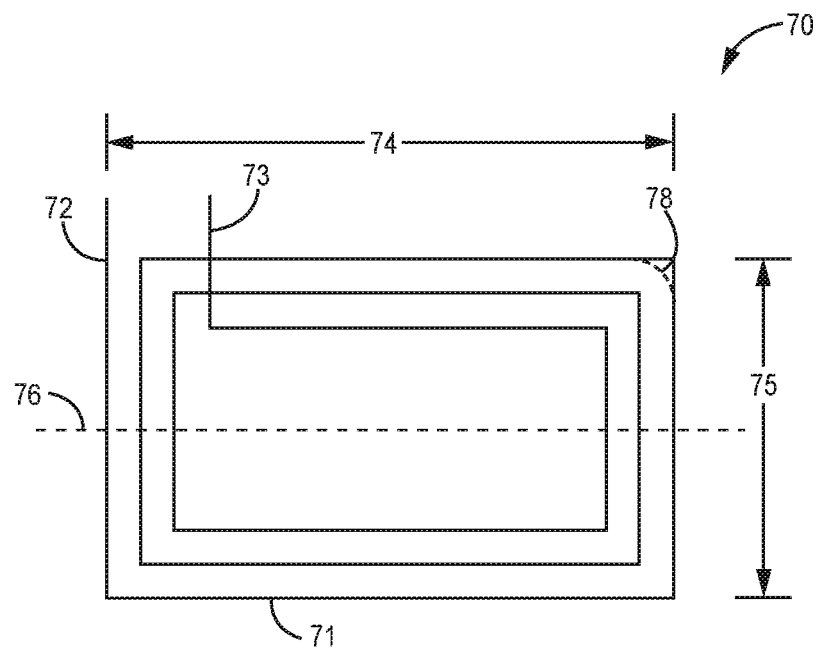
FIGS. 4A-4B illustrate an electrical conductor configured to form a receive coil for an implantable medical device according to various examples described in this disclosure.
Figure 4B:
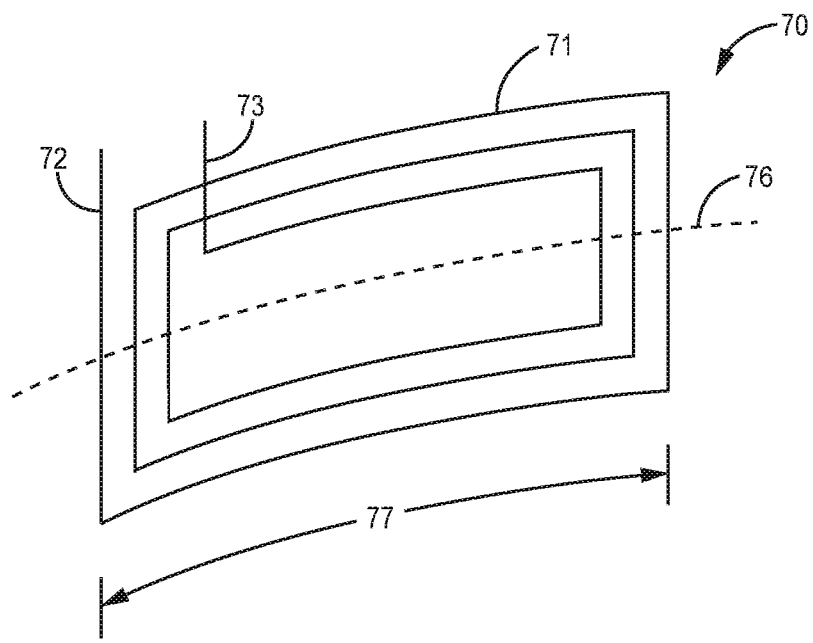

FIGS. 4A-4B illustrate an electrical conductor 71 configured to form a receive coil 70 for an implantable medical device according to various examples described in this disclosure. As shown in FIG. 4A, an electrical conductor 71 is formed into a coil winding having a substantially rectangular shape. The outer-most winding of electrical conductor 71 extends along a length dimension 74, and along a width dimension 75. Length dimension 74 has a same orientation as an orientation of a longitudinal axis 76 extending across receive coil 70 parallel to the length dimension 74. A first end of electrical conductor 71 is electrically coupled to a first lead 72. A second end of electrical conductor 71 is electrically coupled to a second lead 73. First lead 72 and second lead 73 may extend to and electrically couple receive coil 70 with recharging circuitry of the implantable medical device, (not shown in FIG. 4A, but for example recharging circuitry 206 in FIG. 10), which allows currents induced into receive coil 70 by magnetic field(s) imposed onto receive coil 70 to be used to recharge a power source of the implanted medical device coupled to the receive coil, or to power the operation of the electrical circuitry of the device.

As shown in FIG. 4A, the windings of receive coil 70 extending from first lead 72 form the outer-most winding of the receive coil, with additional windings being progressively formed within the previous winding as the electrical conductor 71 extends toward second lead 73. As such, the overall thickness dimension of the receive coil 70 (e.g., a thickness dimension of receive coil 70 orthogonal to both the length dimension 74 and the width dimension 75) may be the thickness of a diameter of the electrical conductor 71. In other words, the coil winding of receive coil 70 may be configured as a flat-wound coil having a generally rectangular shape in the length and width dimensions. Variations in the shape of the coil windings of electrical conductor 71 may include having the corners where the direction of the electrical conductor changes from a lengthwise to widthwise direction include a rounded or curved shape, as illustratively shown by corner radius 78. Further, the number of turns or windings included in receive coil 70 is not limited to a particular number of turns, and in some examples includes ten turns, wherein each turn includes a portion of the electrical conductor forming a four-sided winding of receive coil 70.

As shown in FIG. 4A first lead 72 and second lead 73 are coupled to the electrical conductor 71 at a same corner of the coil winding, so that the first lead 72 and the second lead 73 extend from the coil winding in close proximity to one another. However, the positions of first lead 72 and second lead 73 are not limited to any particular arrangement, such as the arrangement as shown in FIG. 4A. In some examples leads 72 and 73 may extend from other positions of the coil winding of the receive coil 70, including having first lead 72 and second lead 73 extend from different portions of the coil windings so that these leads do not extend from portions of the receive coil that are in close proximity to one another.

Electrical conductor 71 is not limited to being formed from any particular type of material, and may be formed from a conductive metal, such as copper, that is easily formed into a wire and may be easily bent to form the desired shape of the coil winding used to form receive coil 70. The electrical conductor used to form receive coil 70 in some examples may include an insulative material, such as enamel, that is coated over the exterior surface of the conductor to provide an insulative layer between the individual coil windings. In various examples, the electrical conductor used to form receive coil 70 is a multi-strand conductor, such as Litz wire, wherein the electrical conductor used to form each winding is insulated along the outer surface of the electrical conductor, for example using a coating, such as enamel, to reduce the skin effect of the electrical conductor. Skin effect is the characteristic of electrical current flowing through an electrical conductor that causes the flow of current in the electrical conductor to travel though the outer portion, e.g., the "skin" of the conductor, and not through the inner portion of the electrical conductor. The skin effect is more pronounced at higher frequencies. The use of Litz wire helps reduce the skin effect in the electrical conductor at higher frequencies.

An example of receive coil 70 may be retained in the flat-wound configuration as shown in FIG. 4A and used as a receive antenna in an implantable medical device, for example as receive coil 65 of implantable medical device 30 as illustrated and described with respect to FIGS. 3A-3B. In other examples, receive coil 70 may be formed into a curved shape, as illustrated and further described below with respect to FIG. 4B. When formed into a curved shape, receive coil 70 may or may not be affixed to a ferrite sheet, and positioned so that curve of receive coil 70 corresponds to the inner surface 51 the antenna window 40 of implantable medical device 30, forming for example the receive coil 55 of implantable medical device 30 as illustrated and described with respect to FIG. 3A.

As illustrated in FIG. 4B, receive coil 70 is bent along the length of longitudinal axis 76 so that the length dimension 74 of the receive coil forms a corner radius 78. The amount of curvature along longitudinal axis 76 may correspond to the curvature of the inner surface 51 on the antenna window 40 of device 30 so that receive coil 70 may be affixed along and positioned directly adjacent to a portion of the inner surface 51 of the antenna window 40. In examples were the receive coil 70 is affixed to a ferrite sheet (such as ferrite sheet 56 as illustrated and described with respect to FIG. 3A), the amount of curvature of the receive coil 70 is formed so that receive coil 70 may be affixed to a surface of the ferrite sheet, and the surface of the ferrite sheet opposite the surface where the receive coil is attached may be affixed in contact with and directly adjacent to a portion of the inner surface 51 of the antenna window 40, as illustrated by the positioning of receive coil 55 in FIG. 3A.

In examples where receive coil 70 is not affixed to a ferrite sheet, receive coil 70 may be bent along the length of longitudinal axis 76 as shown in FIG. 4B, and affixed in direct contact with and directly adjacent to the inner surface 51 of the antenna window 40 of device 30. Regardless of whether receive coil 70 is affixed to the inner surface 51 through a ferrite sheet or directly to the inner surface, the curvature of receive coil 70 is configured so that the ferrite sheet and the receive coil or the receive coil alone may be positioned in contact with and directly adjacent to a curved portion of the inner surface 51 of the antenna window.

Figure 5A:
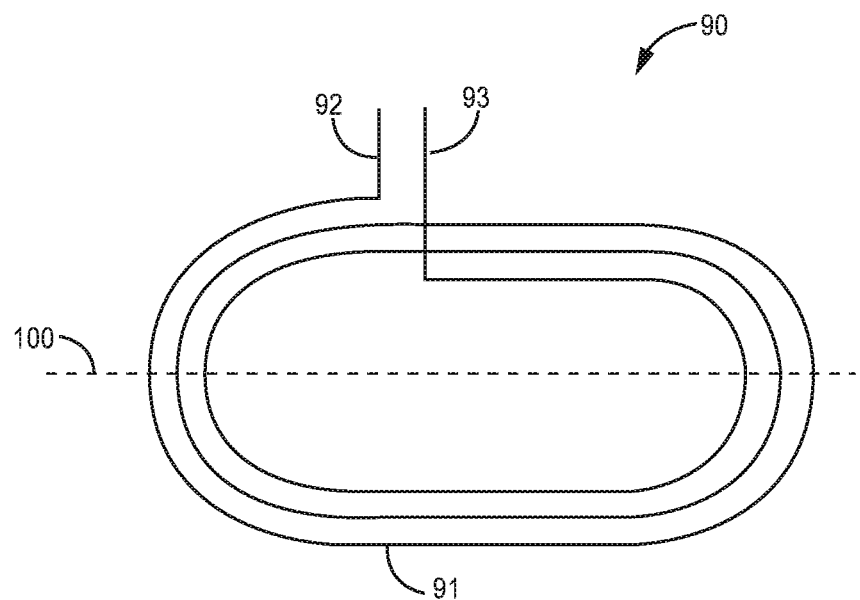
FIG. 5A-5C illustrate an electrical conductor configured to form a receive coil for an implantable medical device according to various examples described in this disclosure.
Figure 5B:
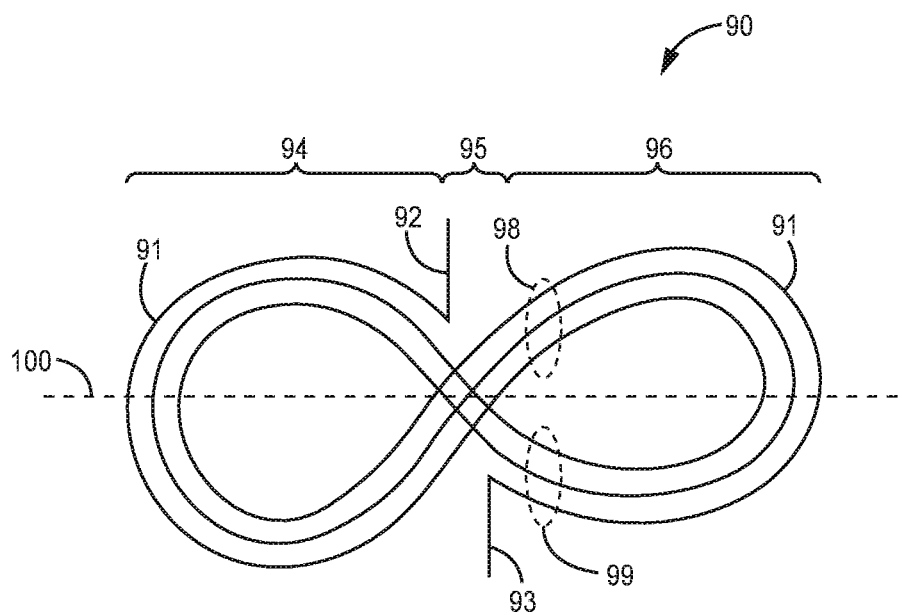
Figure 5C:
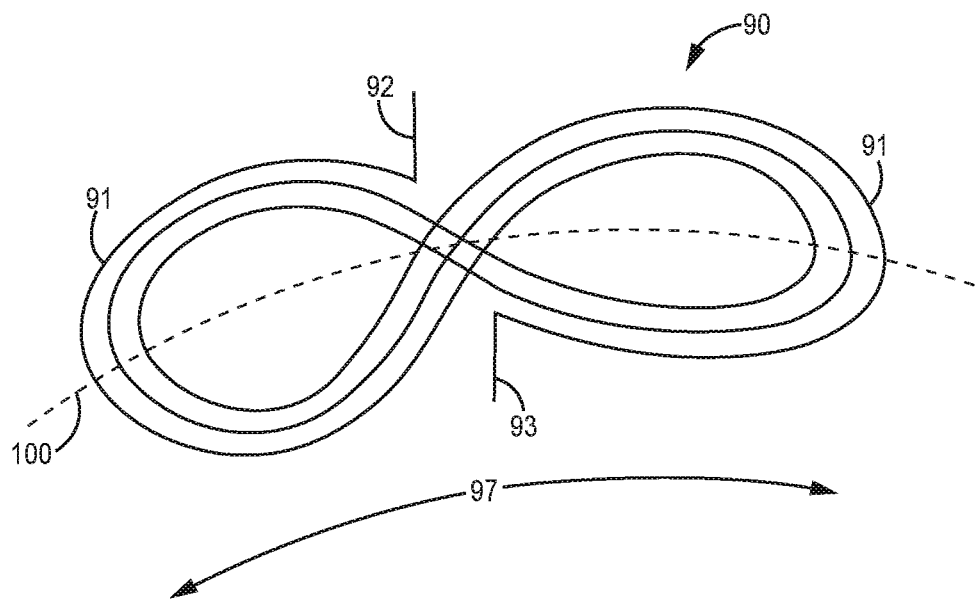
Figure 5D:
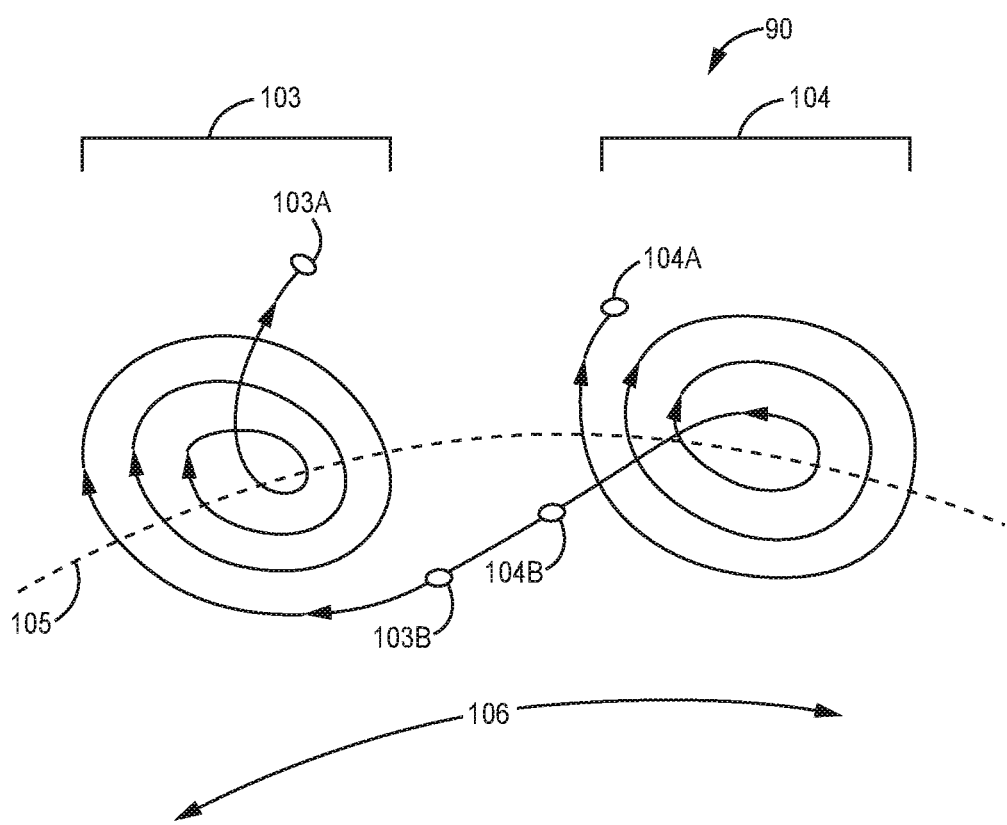
FIG. 5D illustrates an example of electrical conductors configured to form a receive coil for an implantable medical device according to various examples described in this disclosure.

FIG. 5A-5C illustrate an electrical conductor 91 configured to form a receive coil 90 for an implantable medical device according to various examples described in this disclosure. As shown in FIG. 5A, an electrical conductor 91 is formed into a coil winding having a circular or oval shape. A first end of electrical conductor 91 is electrically coupled to a first lead 92 and a second end of electrical conductor 91 is electrically coupled to a second lead 93. First lead 92 and second lead 93 may be configured to extend to and electrically couple receive coil 90 with recharging circuitry of an implantable medical device (not shown in FIG. 5A, but for example recharging circuitry 206 in FIG. 10), which allows currents induced into receive coil 90 by magnetic field(s) imposed onto receive coil 90 to be used to recharge a power source of an implanted medical device coupled to the receive coil, or to power the operation of the electrical circuitry of the device.

As shown in FIG. 5A, the windings of receive coil 90 extending from first lead 92 forms the outer-most winding of the receive coil, with additional windings being progressively formed within the previous windings as the electrical conductor 91 extends toward second lead 93. As such, the overall thickness dimension of the receive coil 90 (e.g., a thickness dimension of receive coil 90) may be the thickness of the diameter of the electrical conductor 91. In other words, the coil winding of receive coil 90 as shown in FIG. 5A may be configured as a flat-wound planar coil having a generally circular or oval shape. The number of turns or windings included in receive coil 90 is not limited to a particular number of turns, and in some examples includes ten turns, wherein each turn includes a portion of the electrical conductor forming a generally circular or oval shaped winding of the receive coil.

As shown in FIG. 5A, first lead 92 and second lead 93 are coupled to the electrical conductor 91 at a same relative position of the respective coil winding the to which these leads are attached, so that the first lead 92 and the second lead 93 extend from the coil winding in close proximity to one another. However, the positions of first lead 92 and second lead 93 are not limited to any particular arrangement, such as the arrangement as shown in FIG. 5A. In some examples leads 92 and 93 may extend from other positions of the coil winding of the receive coil 90, including having first lead 92 and second lead 93 extend from different portions of the coil windings so that these leads do not extend from portions of the receive coil that are in close proximity to one another.

Electrical conductor 91 is not limited to being formed from any particular type of material, and may be formed from any type of electrical conductor described above with respect to electrical conductor 71, including a conductive metal, such as copper, that is easily formed into a wire and may be easily bent to form the desired shape of the coil winding used to form receive coil 70. The electrical conductor used to form receive coil 90 in FIG. 5A in some examples may include an insulative material, such as enamel, coated over the exterior surface of the conductor to provide an insulative layer between the individual coil windings. In various examples, the electrical conductor used to form receive coil 90 is a multi-strand conductor, such as Litz wire, wherein the electrical conductor used to form each winding is insulated along the outer surface of the electrical conductor, for example using a coating, such as enamel, to reduce the skin effect of the electrical conductor.

The receive coil 90 as illustrated in FIG. 5A may be manipulated to include a single half-twist of one portion of the receive coil 90 so that the receive coil forms the shape of an infinity-loop as illustrated in FIG. 5B. As shown in FIG. 5B, the windings of electrical conductor 91 form a first loop 94, and a second loop 96 coupled to the first loop at crossover area 95. A winding of receive coil 90 having an end coupled to first lead 92 extends from first lead 92 and around the outer-most winding of first loop 94, and then to crossover area 95. This same winding extends from crossover area 95 to form a portion of the winding included in second loop 96 before again returning to the crossover area 95. Windings of receive coil 90 continue to form a progressive series of windings forming a portion of the winding in first loop 94, extending to the crossover area 95, and forming a winding in the second loop 96 before again returning to the crossover area 95, until an end of conductor 91 is reached that is coupled to second lead 93. The total number of turns formed by the windings passing around the first loop 94 through the crossover area 95 and around the second loop 96 is not limited to any particular number of turns, and is some examples may be ten turns.

In examples where the infinity-loop shape of receive coil 90 was first formed in the shape of a circular or oval winding as shown in FIG. 5A, all of the electrical conductor 91 aligned in the crossover area 95 may be either above or below all of the other portions of the electrical conductor 91 that are aligned with one another and pass through the crossover area. For example, all portions of the electrical conductor 91 enclosed by dashed oval 98 and that align with one another when entering and exiting the crossover area 95 are all either above (e.g., pass on top of as shown in FIG. 5B) or are all below (e.g., pass underneath) all of the conductors enclosed in dashed oval 99. As a result, the thickness dimension of the infinity shaped coil at the crossover area 95 may be greater than the thickness dimension of two or more portions of the electrical conductor 91 combined.

As an alternative to first forming receive coil 90 as a single loop as illustrated in FIG. 5A and then twisting a portion of the loop used to form the infinity shaped coil as illustrated in FIG. 5B, the infinity shaped coil of FIG. 5B may be wound initially in the figure-eight pattern to form the infinity shaped coil. In various examples of winding the figure-eight pattern to form the infinity shaped coil, the winding in the outermost winding of electrical conductor 91 around first loop 94 may be arranged as the inner-most winding of the electrical conductor 91 around second loop 96. The routing of electrical conductor 91 may continue in a manner such that the second outermost portion of electrical conductor 91 within first loop 94 continues as the second-most inner portion of the electrical conductor 91 formed within the second loop 96. By continuing to alternatively form a winding of receive coil 90 using this outermost versus innermost pattern relative to first loop 94 and second loop 96, the thickness of the windings at the crossover area 95 may be maintained to no more than a thickness dimension of two of the windings of electrical conductor 91 combined. This pattern may therefor provide a flatter or less thick coil winding in the portion of the electrical conductor 91 that crossover one another within the crossover area 95.

Regardless of whether receive coil 90 was formed into the infinity shaped coil by twisting a circular or oval shaped coil or by winding the receive coil in a figure-eight pattern, receive coil 90 may next be formed into a curved shape, as illustrated and further described with respect to FIG. 5C. When formed into a curved shape of FIG. 5C, receive coil 90 may or may not be affixed to a ferrite sheet, and positioned so that curvature of receive coil 90 corresponds to the inner surface 51 for example of the antenna window 40 of implantable medical device 30, forming for example the receive coil 55 of implantable medical device 30 as illustrated and described for example with respect to FIG. 3B.

As illustrated in FIG. 5C, receive coil 90 is bent along the length of longitudinal axis 100 so that the longitudinal dimension corresponding to the longitudinal axis 100 of the receive coil forms a curved shape 97. The amount of curvature along longitudinal axis 100 may correspond to the curvature of the inner surface 51 on the antenna window 40 of device 30 so that receive coil 90 may be affixed along and positioned directly adjacent to a portion of the inner surface 51 of the antenna window 40. In examples were the receive coil 90 is affixed to a ferrite sheet such as ferrite sheet 56 as illustrated and described for example with respect to FIG. 3B, the amount of curvature of the receive coil 90 is formed so that receive coil 90 may be affixed to a surface of the ferrite sheet, and the surface of the ferrite sheet opposite the surface where the receive coil is attached may be affixed in contact with and directly proximity to a portion of the inner surface 51 of the antenna window 40, as illustrated for example by the positioning of receive coil 55 in FIG. 3B.

In examples where receive coil 90 is not affixed to a ferrite sheet, receive coil 90 may be bent along the length of longitudinal axis 100 as shown in FIG. 5C, and affixed in direct contact with and directly adjacent to the inner surface 51 for example of the antenna window 40 of device 30. Regardless of whether receive coil 90 is affixed to the inner surface 51 through a ferrite sheet or directly to the inner surface, the curvature of receive coil 90 is configured so that the ferrite sheet and the receive coil or the receive coil alone may be positioned in contact with and directly adjacent to a curved portion of the inner surface 51 of the antenna window or for example of inner surface 51 of second housing portion 36 as illustrated and described with respect to FIG. 2B.

FIG. 5D illustrates an example of electrical conductors configured to form a receive coil for an implantable medical device according to various examples described in this disclosure. As shown in FIG. 5D, a first electrical conductor is formed into a first coil winding indicated by bracket 103, the first electrical conductor having a first end 103A at one end of the coil winding, and a second end 103B at the end of the electrical conductor opposite first end 103A. First coil winding may be made of any type of electrical conductor, including the conductive wire such as Litz wire as described throughout this disclosure. The first coil winding may be formed in a manner similar or the same as descried with respect to coil 70 as illustrate and described with respect to FIG. 4A.

As shown in FIG. 5D, a second electrical conductor is formed into a second coil winding indicated by bracket 104, the second electrical conductor having a first end 104A at one end of the coil winding, and a second end 104B at the end of the electrical conductor opposite second end 103A. First coil winding may be made of any type of electrical conductor, including the conductive wire such as Litz wire as described throughout this disclosure. The second coil winding may be formed in a manner similar or the same as descried with respect to coil 70 as illustrate and described with respect to FIG. 4A. The type of material used, the general dimensions, and the number of turns used to form the second coil winding are the same or similar to those used to form the first coil winding.

The first coil winding and the second coil windings may be affixed to a ferrite sheet, or to separate ferrite sheets, wherein the ferrite sheets may then be affixed to an inner surface of an interior cavity of an implantable medical device. The inner surface of the interior cavity of the implantable medical device may form a curved surface, wherein the first coil winding and the second coil winding may be positioned next to one another so that a longitudinal axis extending through each of the first coil winding and the second coil winding extends around or along a perimeter of the inner surface and conforms the a curvature (illustratively represented by double-headed arrow 106) of the inner surface of the implantable medical device). The curvature separates the two loops of the dual-winding coil configuration into separate planes, and thus allows the dual-winding coil configuration to generate an induced current flow when a magnetic field is imposed onto one or both of the coil windings.

The second end 103B of the first coil winding is electrically coupled to the second end 104B of the second coil winding. The connection coupling the second end 103B and the second end 104B in some examples may be formed on a circuit board or a hybrid substrate (not shown in FIG. 5D), thus allowing each of the first coil winding and the second coil winding to be coupled together either before or after the coils have been affixed in place within the housing of the implantable medical device. As shown in FIG. 5D, second end 103B of the first coil winding extends to form the outermost winding of the first coil winding, and the inner-most winding of the second coil winding extends to second end 104B, which is directly coupled to second end 103B. The first end 103A of the first coil winding and the first end 104A of the second coil winding are configured to be coupled to recharging circuitry, such as recharging circuitry 206 as illustrated and described with respect to FIG. 10.

The first coil winding and the second coil winding as illustrated in FIG. 5D may be referred to as a dual-winding coil configuration forming a two-loop coil winding. The dual-winding coil configuration illustrated and described with respect to FIG. 5D may be included in place of the infinity shaped coil(s) in any of the receive antenna configurations described throughout this disclosure. For examples, the dual-winding coil configuration as shown in FIG. 5D may be substituted for the infinity shaped receive coil 55 illustrated and described with respect to FIG. 3B. A pair of the dual-winding coil configuration as shown in FIG. 5D may be substituted for the pair of infinity shaped receive coils 164, 174 illustrated and described with respect to FIGS. 8A-8B. In a manner the same as described above with respect to the use of infinity shaped coil winding, as long as the two loops of the dual-winding coil configuration are positioned in different planes relative to one another, the dual-winding coil configuration may provide a recharging current induced into one or both of the coil winding when a magnetic field is imposed onto the dual-winding coil configuration from a variety of different magnetic field direction relative to the orientation of the dual-winding coil configuration.

Figure 6:
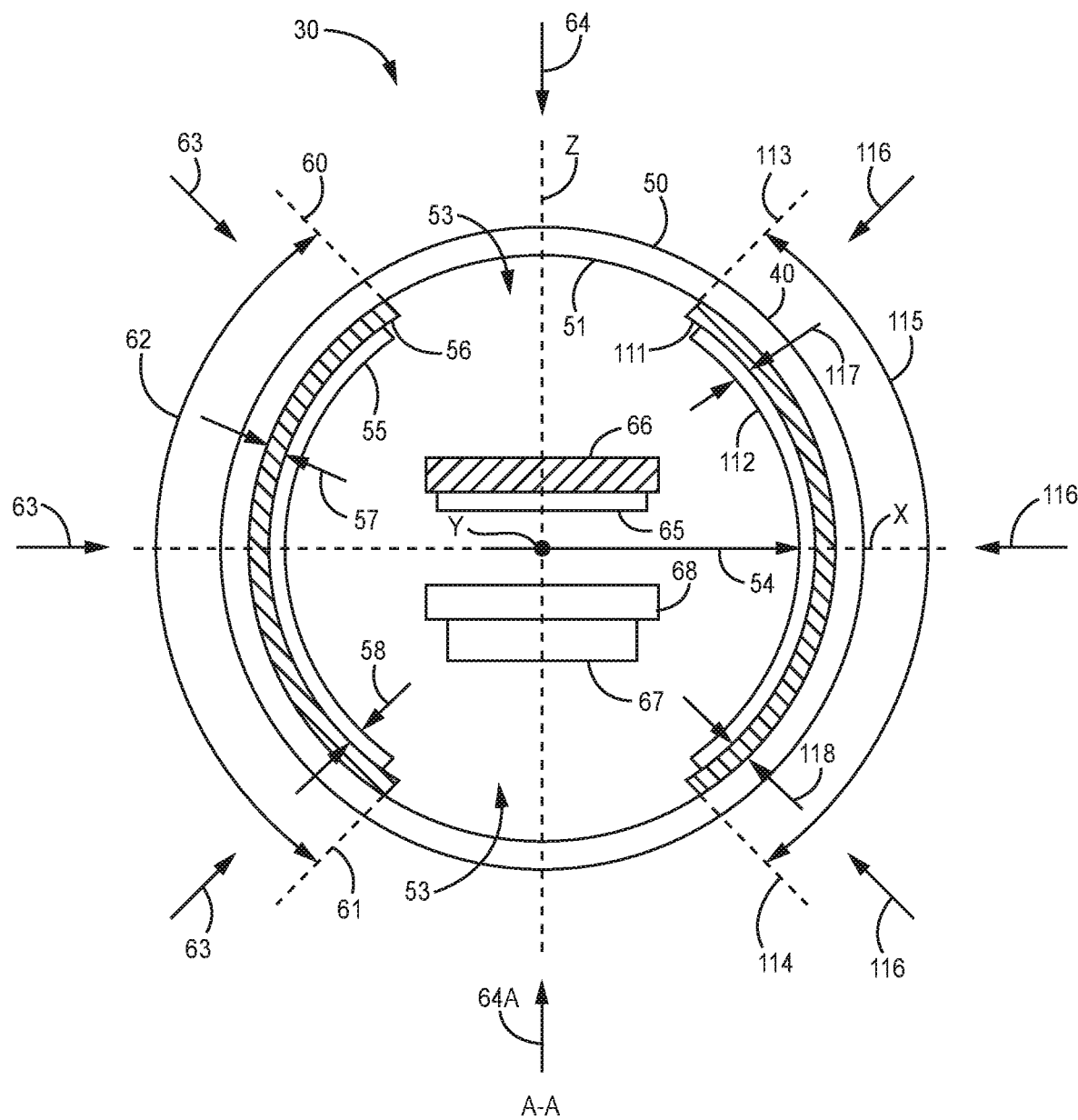
FIG. 6 is another cross-sectional view of an example receive antenna configuration for an implantable medical device according to various examples described in this disclosure.

FIG. 6 is another cross-sectional view A-A of an example receive antenna configuration for an implantable medical device 30 according to various examples described in this disclosure. In FIG. 6, items having a same reference number as items illustrated and described for example with respect to FIG. 3A correspond to a same or similar item, and may include any of the features and provide any of the functions as described for the corresponding item in FIG. 3A. Although described with respect to device 30 having an antenna window 40, the receive antenna configuration(s) as described below with respect to FIG. 3A may also be provided in a device that does not include a separate antenna window as part of the housing of the device, such as device 30A as illustrated and described with respect to FIG. 2B. For example the receive antenna(s) described below with respect to FIG. 6 may be affixed to and/or positioned within a portion of the second housing portion 36 as illustrated and described above with respect to FIG. 2B.

The example of device 30 as shown in FIG. 6 includes the receive coil 55 and ferrite sheet 56 arranged along a portion of the inner surface 51 of antenna window 40 in a same or similar manner as illustrated and described for example with respect to FIG. 3A. Receive coil 55 may include any of the single loop coil windings formed in any of the configurations of coil winding described through this disclosure for a curve-shaped coil winding, including receive coil 70 as illustrated and described with respect to FIGS. 4A-4B, and a version of the single loop coil as illustrated and described with respect to FIG. 5A. The example of device 30 as shown in FIG. 6 also includes receive coil 65 affixed to ferrite sheet 66 and telemetry antenna 67 coupled to substrate 68 in a same or similar manner as illustrated and described for example with respect to FIG. 3A. In the example of device 30 shown in FIG. 6, each of the receive coil 55, receive coil 65, and telemetry antenna 67 may be arranged and provided in any of the example configurations illustrated and described for example with respect to device 30 and FIG. 3A, and may be configured to perform any of the functions and to provide any of the features ascribed to device 30 and FIG. 3A.

In addition, as shown in FIG. 6 device 30 includes a second curved-shaped receive coil 112 affixed to ferrite sheet 111. Ferrite sheet 111 is affixed to a portion of inner surface 51 extending between a third radial position 113 and a fourth radial position 114 of the inner surface of the antenna window 40. Ferrite sheet 111 is in contact with and directly adjacent to the portion of the inner surface 51 extending between third radial position 113 and fourth radial position 114 so that the surface of ferrite sheet 111 forms a curved surface that corresponds to the curvature of the inner surface 51 in the area extending between third radial position 113 and fourth radial position 114. Ferrite sheet 111 may have a thickness dimension 118 having a same value as the thickness dimension 57 as ferrite sheet 56. Receive coil 112 is affixed to a surface of ferrite sheet 111 opposite the surface of ferrite sheet 111 that is in contact with inner surface 51. Receive coil 112 also is bent to form a curvature of the windings forming receive coil 112 that conforms to the curvature of the inner surface 51 between third radial position 113 and fourth radial position 114. Receive coil 112 may have a thickness dimension 117 having a same or similar value as the thickness dimension 58 of receive coil 55.

Receive coil 112 in some example may not be affixed to a ferrite sheet, such as ferrite sheet 111 as shown in FIG. 6, and may instead be directly affixed to the inner surface 51 of the antenna window 40 in the area of the inner surface that extends between third radial position 113 and fourth radial position 114. Receive coil 112 may include any of the single loop coil windings formed in any of the configurations of coil winding described through this disclosure for a curve-shaped coil winding, including receive coil 70 as illustrated and described with respect to FIGS. 4A-4B, and a version of the single loop coil as illustrated and described with respect to FIG. 5A. In some examples of device 30 as shown in FIG. 6, receive coil 112 is configured using a same arrangement for the coil winding used to form the coil as used to form receive coil 55. In other examples, the configuration of the coil winding used to form receive coil 112 may be different from the configuration of the coil winding used to form receive coil 55.

In some example of device 30 as shown in FIG. 6, one or both receive coil 65 and telemetry antenna 67 may be absent from the device. In such examples where the telemetry antenna 67 is absent, one or some combination of receive coils 112, 55 and/or 65 (when receive coil 65 is provided as part of device 30) may be used to provide the transmission and/or reception functions for any telemetry communications to and from device 30 to external devices, such as external device 11 and/or transceiver 16 as illustrated and described with respect to FIG. 1, or any other external devices described throughout this disclosure that communicate wirelessly with examples of device 30.

Referring again to FIG. 6, the positioning of receive coil 112 along the inner surface 51 of antenna window 40 between third radial position 113 and fourth radial position 114 may allow a high level of inductive coupling efficiency to be achieved between receive coil 112 and magnetic field(s) imposed on receive coil 112 having a magnetic field direction incident on the receive coil 112 over angular range 115, including angles of the magnetic field(s) that may be tilted (non-perpendicular) relative to the Y-axis and over angular range 115, in a similar manner as described above with respect to angular range 62 and receive coil 55. The positioning of ferrite sheet 111 between the receive coil 112 and inner surface 51 of antenna window 40 may increase the level of inductive coupling between receive coil 112 and the magnetic fields having magnetic field directions indicated by arrows 116. Although a level of inductive coupling may also occur between receive coil 112 and magnetic fields having magnetic field direction represented by arrows 63 in FIG. 6, the level of coupling between the magnetic fields having a magnetic field direction indicated by arrow 63 and receive coil 112 may be a lower level compared to magnetic fields having the magnetic field direction indicated by arrows 116 for a given same level of magnetic field intensity. For example, other devices such as receiving coil 65, ferrite sheet 66, telemetry antenna 67 and substrate 68, ferrite sheet 56 and/or receive coil 55 may reduce the level of inductive coupling efficiency that may be achieved between receive coil 112 and magnetic fields imposed on receive coil 112 that have a magnetic field direction indicated by arrows 63. Further, because any magnetic fields having a magnetic field direction indicated by arrow 63 would be imposed onto receive coil 112 directly without passing through ferrite sheet 111 in the process, the level of inductive coupling between these magnetic fields and receive coil 112 for these magnetic field(s) may be lower compared to level of inductive coupling achieved for magnetic fields having a same magnetic field intensity but imposed on receive coil 112 having the magnetic field direction indicated by arrows 116.

By including a second receive coil 112 arranged along the portion of inner surface 51 as shown in FIG. 6, and due at least in part to the curvature of receive coil 112, a higher level of inductive coupling efficiency may be achieved with respect to device 30 and magnetic fields imposed onto device 30 that have a magnetic field direction indicted by one or more of arrows 63 and/or 116. This higher level of inductive coupling may be achieved for any magnetic fields imposed on device 30 over the angular range 115 extending between third radial position 113 and fourth radial position 114 and parallel to the X-Z plane as illustrated in FIG. 6. In addition, a high level of inductive coupling efficiency may also be achieved between receive coil 112 and magnetic fields imposed on device 30 and having a magnetic field direction indicated by arrows 116 extending between third radial position 113 and fourth radial position 114, but also "tilted" at some non-perpendicular angle of incident relative to the Y-axis (longitudinal axis) of device 30. The inclusion of the second receive coil 112 in addition to the receive coil 55 in examples of device 30 may further increase the variations in the angles and ranges of angles over which a magnetic field may be imposed on device 30 while achieving a minimum level of inductive coupling efficiency between the receive antennas of the device and the magnetic fields imposed onto the device.

Figure 7A:
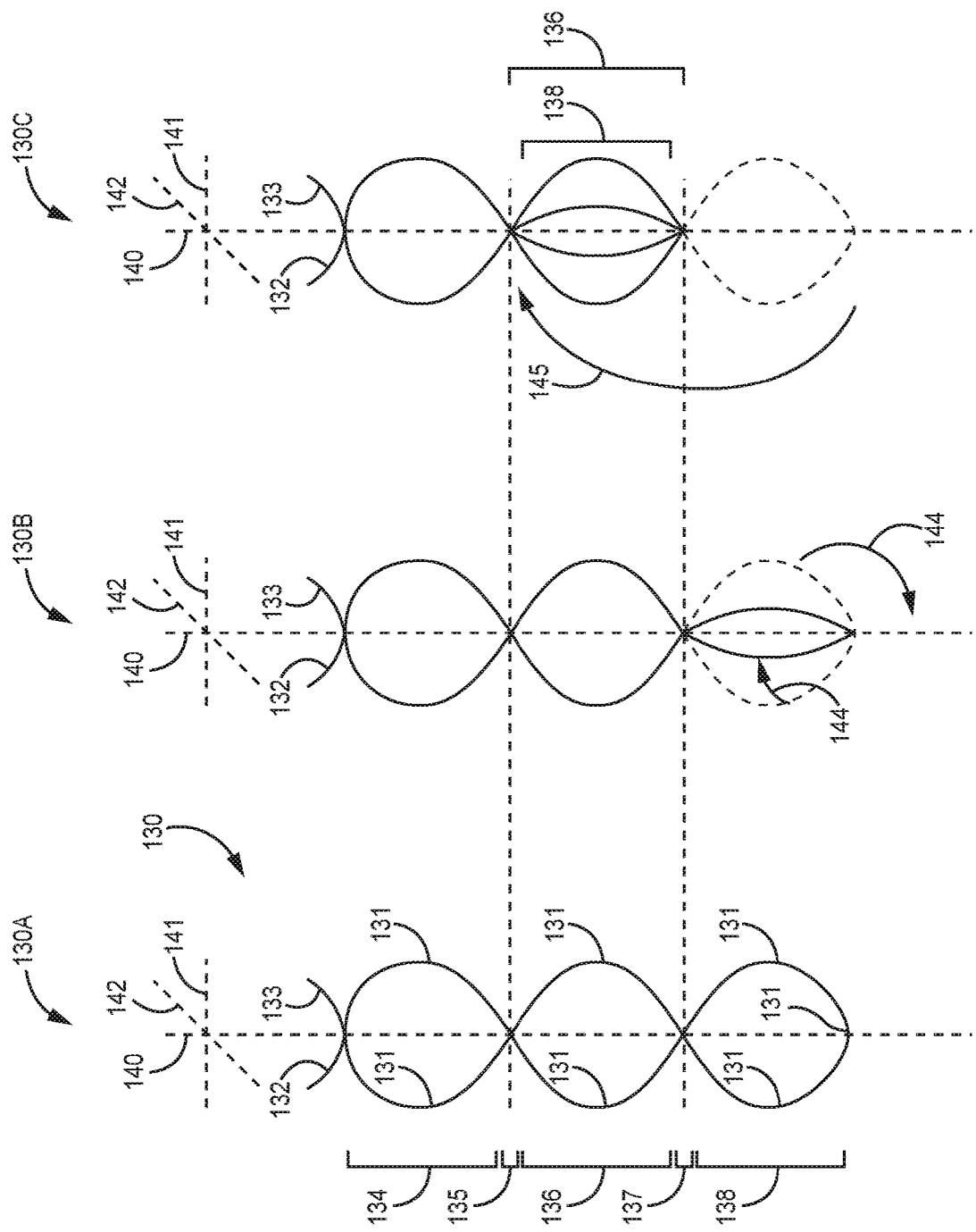
FIGS. 7A-7B illustrate a sequence of operations performed on an electrical conductor to form a receive coil for an implantable medical device according to various examples described in this disclosure.
Figure 7B:
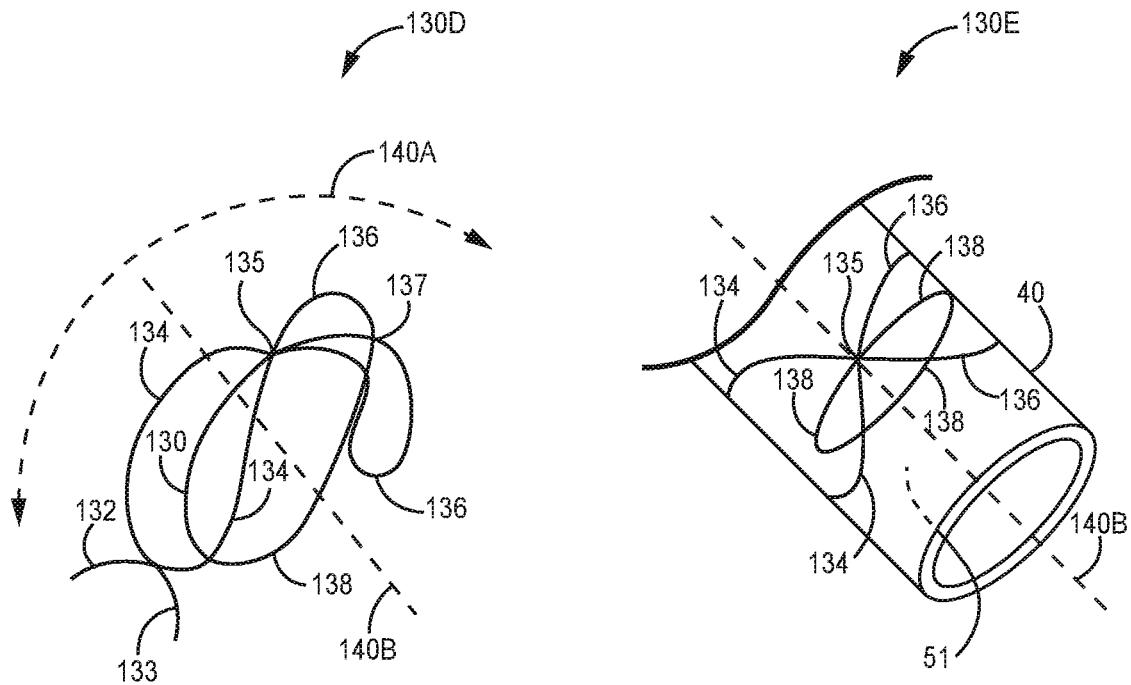

FIGS. 7A-7B illustrate a sequence of operations using an electrical conductor 131 to form a receive coil 130 for an implantable medical device according to various examples described in this disclosure. As shown diagram 130A in FIG. 7A, an electrical conductor 131 is formed into a coil winding comprising three loops. A first loop of the receive coil 130 is generally indicted by bracket 134 (hereinafter "first loop 134"), a second loop is generally indicted by bracket 136 (hereinafter "second loop 136"), and a third loop is generally indicated by bracket 138 (hereinafter "third loop 138"). A first end of electrical conductor 131 is electrically coupled to a first lead 132 and a second end of electrical conductor 131 is electrically coupled to a second lead 133. First lead 132 and second lead 133 may be configured to extend to and electrically couple receive coil 130 with recharging circuitry of an implantable medical device (not shown in FIG. 7A, but for example recharging circuitry 206 in FIG. 10), which allows currents induced into receive coil 130 by magnetic field(s) imposed onto the receive coil to be used to recharge a power source of an implanted medical device coupled to the receive coil, or to power electrical circuitry of the implantable medical device.

As shown in diagram 130A, the electrical conductor 131 of receive coil 130 extends from first lead 132, and forms a first half of a winding of first loop 134. The electrical conductor 131 extends from the first half of the winding of first loop 134 to first crossover area 135, and extends away from first crossover area 135 to form a first half of a winding of second loop 136. The electrical conductor 131 extends from the first half of the winding of second loop 136 to second crossover area 137, and extends away from second crossover area 137 to form a full winding of third loop 138, then returning to the second crossover area 137. Electrical conductor 131 exits the second crossover area 137 to complete the second half the winding of second loop 136, continue on to and exits the first crossover area 135, and completes the second half of the winding of first loop 134, thus extending a single winding of the electrical conductor through each side of loops 134, 136 and 138, and through each of crossover areas 135 and 137. This or a similar routing of electrical conductor 131 may be repeated for some positive integer "N" number of times, wherein the value for "N" represents the number of turns included in the completed receive coil 130. Upon completion of the desired number of turns for receive coil, 130, electrical conductor 131 may exit first loop 134 and form second lead 133.

The number of turns or windings included in receive coil 130 is not limited to a particular number of turns, and in some examples includes ten turns, wherein each turn includes a portion of the electrical conductor forming both halves of a loop in each of loops 134, 136, and 138. As shown in FIG. 7A, first lead 132 and second lead 133 are provided a same relative position relative to first loop 134 so that first lead 132 and second lead 133 extend from the coil winding in close proximity to one another. However, the positions of first lead 132 and second lead 133 are not limited to any particular arrangement, such as the arrangement as shown in diagram 130A. In some examples leads 132 and 133 may extend from other positions of the coil winding of the receive coil 130, such as crossover area 135 or crossover area 137. In other examples first lead 132 and second lead 133 extend from different portions of the coil windings relative to one another so that these leads do not extend from portions of the receive coil that are in close proximity to one another.

Electrical conductor 131 is not limited to being formed from any particular type of material, and may be formed from any type of electrical conductor described throughout this disclosure, including a conductive metal, such as copper, that is easily formed into a wire and may be easily bent to form the desired shape of the coil winding. The electrical conductor used to form receive coil 130 in some examples may include an insulative material, such as enamel, coated over the exterior surface of the conductor to provide an insulative layer between the individual coil windings. In various examples, the electrical conductor used to form receive coil 130 is a multi-strand conductor, such as Litz wire, wherein the electrical conductor used to form each winding is insulated along the outer surface of the electrical conductor, for example using a coating, such as enamel, to reduce the skin effect of the electrical conductor.

Receive coil 130 may be initially formed as a circular or oval shaped winding, such as receive coil 90 as illustrated in FIG. 5A, and then twisted in two places to create the first crossover area 135 and the second crossover area 137, respectively, as illustrated in diagram 130A of FIG. 7A. In other examples, receive coil 130 as shown in diagram 130A of FIG. 7A may be wound in an initial pattern that forms the loops 134, 136, and 138 and crossover areas 135 and 137 as illustrated by FIG. 7A. Any of the winding techniques described throughout this disclosure may be used to from the loops and crossover area as depicted for receive coil 130 in FIG. 7A.

When receive coil 130 is configured as shown in FIG. 7A, a longitudinal axis 140 of the receive coil may extend through each of loops 134, 136 and 138 and intersect a point within each of the crossover areas 135 and 137 so that a mirror image of a half loop for each of loops 134, 136, and 138, respectively, occurs on each side of the longitudinal axis 140, with the exception of the positioning of the first lead 132 and second lead 133. As shown in diagram 130A, the electrical conductor 131 forming the windings of receive coil 130 lies in a plane or a set of coplanar planes that include both the longitudinal axis 140 and a second axis 141 that is perpendicular to the longitudinal axis 140 as shown in diagram 130A. A third axis 142 that is perpendicular to both the longitudinal axis 140 and the second axis 141 is also perpendicular to the plane or set of planes that the windings of the receive coil lie within as shown in diagram 130A.

Diagram 130B of FIG. 7A illustrates a step in the formation of receive coil 130 illustrated in diagram 130A. As shown in diagram 130B, third loop 138 of receive coil 130 is twisted at second crossover area 137 so that third loop 138 is rotated around longitudinal axis 140 approximately 90 degrees, as represented by arrows 144. As shown in diagram 130B, when this step is completed, the windings of electrical conductor 131 that form third loop 138 lie generally in a plane or a set of coplanar planes that include longitudinal axis 140 and third axis 142, and which is/are perpendicular to the plane(s) where first loop 134 and second loop 136 generally lie.

Diagram 130C of FIG. 7A illustrates another step in the formation of receive coil 130 illustrated in diagram 130B. As shown in diagram 130C, after being twisted so that the third loop 138 of receive coil 130 is substantially perpendicular to the second loop 136 and first loop 134, third loop 138 is folded upward so that third loop 138 is rotated around second axis 141 using second crossover area 137 as the center point of the rotation as illustrated by arrow 145. The processing of third loop 138 as shown in diagram 130C may bring the end of third loop 138 that is opposite the second crossover area 137 into proximity with the first crossover area 135. In diagram 130C, the orientation of the winding of third loop 138 remains generally perpendicular to the orientation of the winding of second loop 136 and first loop 134.

Diagram 130D of FIG. 7B illustrates another step in the formation of receive coil 130 illustrated in diagram 130C of FIG. 7A. As shown in diagram 130D of FIG. 7B, while maintaining third loop 138 in a plane that includes longitudinal axis 140, first loop 134 and second loop 136 are compressed so that the end of first loop 134 that includes first lead 132 and second lead 133 is moved along longitudinal axis 140 toward an end of third loop 138. As a result, the portion of longitudinal axis 140 that originally extended through first loop 134, first crossover area 135, and second loop 136 takes on an arch-shaped curvature as shown in diagram 130D as dashed curved line 140A that generally corresponds to the shape of a portion of the third loop 138, and extending from the end of first loop 134 that includes lead 132, 133, through first crossover area 135, through second loop 136, and to second crossover area 137.

When formed as shown in diagram 130D, first loop 134 and second loop 136 extend in an arch shape at least partially encircling a portion of the windings of electrical conductor 131 forming third loop 138. The arch-shaped curvature formed by first loop 134 and second loop 136 correspond to a curved longitudinal axis 140A as shown in diagram 130D, wherein the arch-shaped curvature of first loop 134 and second loop 136 extend around and at least partially encircle a cylindrical shaped volume having a circular cross-sectional shape and centered around a central axis 140B extending along the height dimension of the cylindrical shaped volume. Third loop 138 is positioned in a plane or a set of coplanar planes that is/are perpendicular to the central axis 140B, wherein the plane or set of coplanar planes in which the windings forming third loop 138 lie cut the cylindrical shape in cross-section, and wherein the outside perimeter of third loop 138 is also circular. The cross-sectional dimension of the cylindrical shaped volume encircled by first loop 134 and second loop 136, correspond generally to a same diameter dimension for the circular shaped windings forming third loop 138, and are just smaller than an inside cross-sectional dimension of a portion of a housing of an implantable medical device into which the receive coil 130 as configured in diagram 130D is arranged to be positioned within.

Diagram 130E of FIG. 7B illustrates another step in the formation of receive coil 130 illustrated in diagram 130D of FIG. 7B. As shown in diagram 130E, receive coil 130 in the configuration that was shown in diagram 130D is positioned within a portion of the housing of an implantable medical device, such as antenna window 40 of implantable medical device 30 (e.g., FIG. 2A). As shown in diagram 130E of FIG. 7B, first loop 134 and second loop 136 are affixed to the inner surface 51 of antenna window 40 so that the curvature of the first and second loops along axis 140A corresponds to the curvature of the inner surface 51, and at least partially encircle central axis 140B, which now aligns with and corresponds to the longitudinal axis 46 extending through the center point of the diameter of antenna window 40 in cross-section. In addition, third loop 138 is positioned so that the windings forming third loop 138 extend around the inner surface 51 of antenna window 40, forming a coil having a normal axis that aligns with central axis 140B.

When receive coil 130 is arranged as shown in diagram 130E to operate as a receive antenna in an implantable medical device (e.g., device 30—FIG. 2A), first loop 134 and second loop 136 may operate as an infinity shaped or figure-eight coil as described throughout this disclosure, and may provide a minimum level of inductive coupling efficiency with magnetic fields imposed on antenna window 40 over a range of magnetic field directions as described throughout this disclosure, such as magnetic fields having magnetic field directions illustrative and described above with respect to arrows 63, 63A, 64, and 64A with respect to FIG. 6. In addition, due to the orientation of the normal axis of third loop 138 as aligning with the central axis 140B, receive coil 130 may generate some level of induced current when magnetic fields having a magnetic field direction that corresponds with the orientation of central axis 140B, and thus with the orientation of the normal axis of third loop 138, are imposed on the device including receive coil 130 as configured in diagram 130E.

As such, many of the orientations of magnetic fields imposed on an implantable medical device having a receive coil arranged as shown in diagram 130E for the purpose of recharging a power source within the implantable medical device may provide a minimum level of inductive coupling efficiency between the imposed magnetic fields and the implantable medical device regardless of the orientation of the magnetic field direction and/or the orientation of the implantable medical device during the recharging session. This feature of receive coil 130 may be especially important with performing a recharging operation on a deeply implanted medical device, and/or when the precise orientation of the implanted device may not be known and/or is not constant, for example due to movement of the device and/or movements of or within the patient. Another advantage of the multi-loop coils such as receive coil 130 or any of the other multi-loop coils winding described in this disclosure include that in addition to providing a wide range of possible orientations for imposed magnetic fields that provide inductive coupling to the receive coil winding, the number of additional electronic components that may need to be coupled to the multi-loop coil may require only one set of a tuning capacitor, a diode and smoothing cap needed as rectifier components for the receive coil. This features of having a single set of rectifier components needed to be coupled to a multi-loop coil provides a savings of additional space and real estate for example on a hybrid circuit where such electrical component are located within the implantable medical device, thus further aiding in miniaturization of the electronic circuits and/or the overall dimensions required for the housing of the implantable medical device.

Figure 7C:
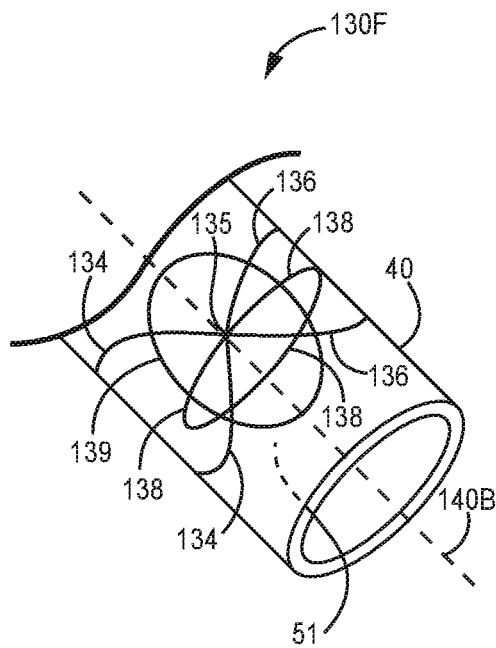
FIG. 7C illustrates and example receive antenna configuration for an implantable medical device according to various examples described in this disclosure.

FIG. 7C illustrates an example receive antenna configuration for an implantable medical device according to various examples described in this disclosure. As shown in diagram 130F of FIG. 7C, a first receive coil 130 in the same configuration that was shown in diagram 130E of FIG. 7B is positioned within a portion of the housing of an implantable medical device, such as antenna window 40 of implantable medical device 30 (e.g., FIG. 2A). As shown in diagram 130F of FIG. 7C, first loop 134 and second loop 136 are affixed to the inner surface 51 of antenna window 40 so that the curvature of the first and second loops along axis 140A corresponds to the curvature of the inner surface 51, and at least partially encircle central axis 140B, which now aligns with and corresponds to the longitudinal axis 46 extending through the center point of the diameter of antenna window 40 in cross-section. Third loop 138 is positioned so that the windings forming third loop 138 extend around the inner surface 51 of antenna window 40, forming a coil having a normal axis that aligns with central axis 140B.

In diagram 130F, a second receive coil 139 is also provided within the portion of the housing of the implantable medical device illustrated in the diagram. Second receive coil 139 may include a single loop coil winding, such as coil winding 70 (FIGS. 4A-4B) that is positioned within the interior cavity of the antenna window 40, for example as illustrated and described with respect to receive coil 69A of FIG. 3B. Second receive coil 139 may be separately coupled to recharging circuitry (e.g., recharging circuitry 206—FIG. 10) through lead (not shown in FIG. 7C) coupled to the electrical conductor forming the winding of second receive coil 139. In other examples, second receive coil 139 is a fourth loop formed from the same electrical conductor used to form the first, second, and third loops of the receive antenna, and is coupled to the first, second, and third loops through an additional crossover area formed for example by twisting or during winding of the electrical conductor 131.

Second receive coil 139 may be affixed to a ferrite sheet, (e.g., ferrite sheet 69B in FIG. 3B), or may not be affixed to a ferrite sheet, and/or may be self supported, or may be supported by a substrate (not shown in FIG. 7C), such as a circuit board. In various examples, the normal axis of second receive coil 139 is orientated so that the normal axis is directed to the crossover area 135 between first loop 134 and 136 in a first direction, and toward a gap between first loop 134 and second loop 136 farthest away from crossover area 135 in a second direction. This orientation of the normal axis of second receive coil 139 may allow the second receive coil to have a maximum coupling efficiency with magnetic field(s) having magnetic field direction(s) that are not necessary optimal for inducing current(s) into one more of the loops of receive coil 130. In addition to increasing the range of magnetic field directions that may provide a high level of inductive coupling efficiency with the device, the receive antenna configuration illustrated in diagram 130F are only requires two sets of rectification components (one set for coil 130 and one set for coil 139), thus saving the amount of real estate required and the overall number of components required for the rectification circuitry associated with the receive antenna configuration.

Figure 8A:
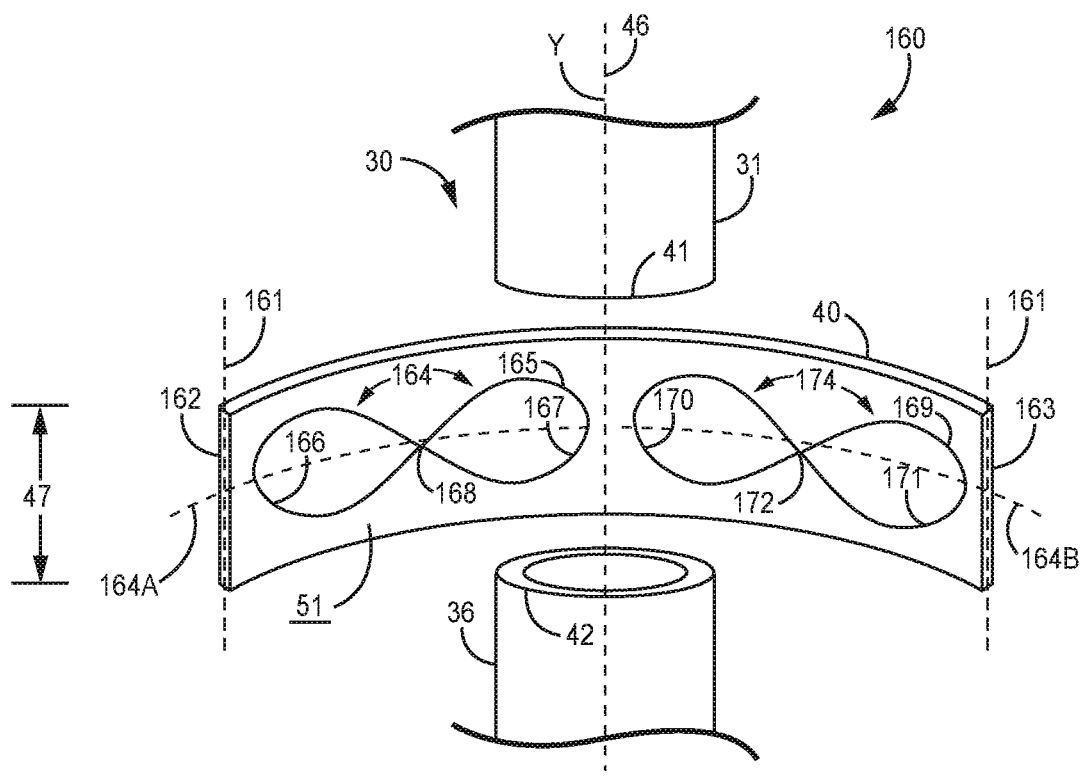
FIG. 8A illustrates a cutaway and exploded view of an example receive antenna configuration for an implantable medical device according to various examples described in this disclosure.

FIG. 8A illustrates a cutaway and exploded view 160 of an example receive antenna configuration for an implantable medical device 30 according to various examples described in this disclosure. FIG. 8A includes an illustrative depiction of the antenna window 40 with a first housing portion 31 and a second housing portion 36 on opposite sides (top and bottom sides) of the antenna window 40. In FIG. 8A, antenna window 40 has been illustratively separated and moved away from first housing portion 31 at first seam 41 and illustratively separated and moved away for second housing portion 36 at second seam 42. In addition, antenna window 40 has been illustratively cut open along an illustrative axis 161 to form illustrative edges 162 and 163 along the cut line of axis 161. Edges 162 and 163 have been illustratively separated from one another to show inner surface 51 of the antenna window 40 depicted as a flat surface facing in an outward direction as viewed in FIG. 8A.

As shown in FIG. 8A, a first receive coil 164 and a second receive coil 174 are affixed to inner surface 51 of antenna window 40. Each of receive coils 164 and 174 comprises an individual electrical conductor formed into an infinity shaped coil having a first loop and a second loop configured in a figure-eight pattern. For example, first receive coil 164 may be formed using electrical conductor 165 to include a first loop 166, crossover area 168, and a second loop 167. First receive coil 164 may be formed from electrical conductor 165 and arranged in a curved shape so that an axis 164A extending from one end of first loop 166 opposite crossover area 168 through crossover area 168 and to an end of second loop 167 that is opposite the crossover area 168 has a curvature that corresponds to the curvature of inner surface 51 of antenna window 40. Similarly, second receive coil 174 may be formed using electrical conductor 169 to include a first loop 170, crossover area 172, and a second loop 171. Second receive coil 174 may be formed using electrical conductor 169 arranged in a curved shape so that an axis 168A extends from one end of first loop 170 opposite crossover area 172 through crossover area 172 and to an end of second loop 171 that is opposite that crossover area 172 has a curvature that corresponds to the curvature of inner surface 51 of antenna window 40. Receive coils 164, 174 may be formed using any of the materials, winding formations, and techniques, or any combination thereof, as described for infinity shaped coils throughout this disclosure, and any equivalents thereof, including but not limited to any examples of receive coil 90 as illustrated and described with respect to FIGS. 5B-5C. Although described with respect to infinity shaped coils, coils 164 and 174 in some examples may each be formed using the dual-winding coil configuration 102 illustrated and described with respect to FIG. 5D.

Referring again to FIG. 8A, the curvature of axis 164A and 164B allows receive coils 164 and 174, respectively, to be affixed to and assume the shape of the curvature of the inner surface 51 of device 30. As previously described, the curvature of the inner surface 51 may encircle a cylindrical shaped interior cavity having a circular shape in cross section. Receive coils 164 and 174 may in some examples be affixed directly to the inner surface 51 of antenna window 40. In some examples, receive coils 164 and 174 may be affixed to a first surface of a ferrite sheet or sheets, (not shown in FIG. 8A, but for example ferrite sheets 177, 178, respectively, as shown in FIG. 8B) wherein the ferrite sheet(s) are then affixed to inner surface 51 so that the ferrite sheet(s) is/are positioned between the receive coils, respectively, and the inner surface 51.

As shown in FIG. 8A, portions of the loops included in receive coils 164 and 174 may extend to a height dimension within antenna window 40 that is nearly the height dimension 47 of the antenna window itself. In addition, second loop 167 of receive coil 164 extends to be in close proximity, but not in contact with the first loop 170 of receive coil 174. When arranged in the antenna window 40 in the actual state (e.g., not separated along edges 162, 163 as illustrated in FIG. 8A for illustrative purposes only), the first loop 166 of receive coil 164 extends to be in close proximity, but not in contact with the second loop 171 of receive coil 174. As shown in FIG. 8A, axis 164A of receive coil 164 is aligned with axis 168A of receive coil 174 relative to the height dimension 47 of the antenna window 40. As such, a large portion of the inner surface 51 around the entirety of the perimeter of inner surface 51 falls within areas into which one of the loops of either first receive coil 164 or second receive coil 174 extend. When the pair of receive coils 164 and 174 are arranged within an antenna window of an implantable medical device as shown in FIG. 8A, the pair of coils provide a wide range of relative angular orientations between magnetic fields imposed on the device and the device that results in a high level of inductive coupling efficiency being achieved between the imposed magnetic fields and the receive coils, as further described below with respect to FIG. 8B. It would be understood that the depiction the flat shape of antenna window 40 as illustrated in FIG. 8A is for illustrative purposes only, and is not intended to represent the actual shape or configuration, e.g., an antenna window that may be split open and then reformed together, as illustrated in FIG. 8A, that might be used in actual practice on or incorporated into an implantable medical device.

Figure 8B:
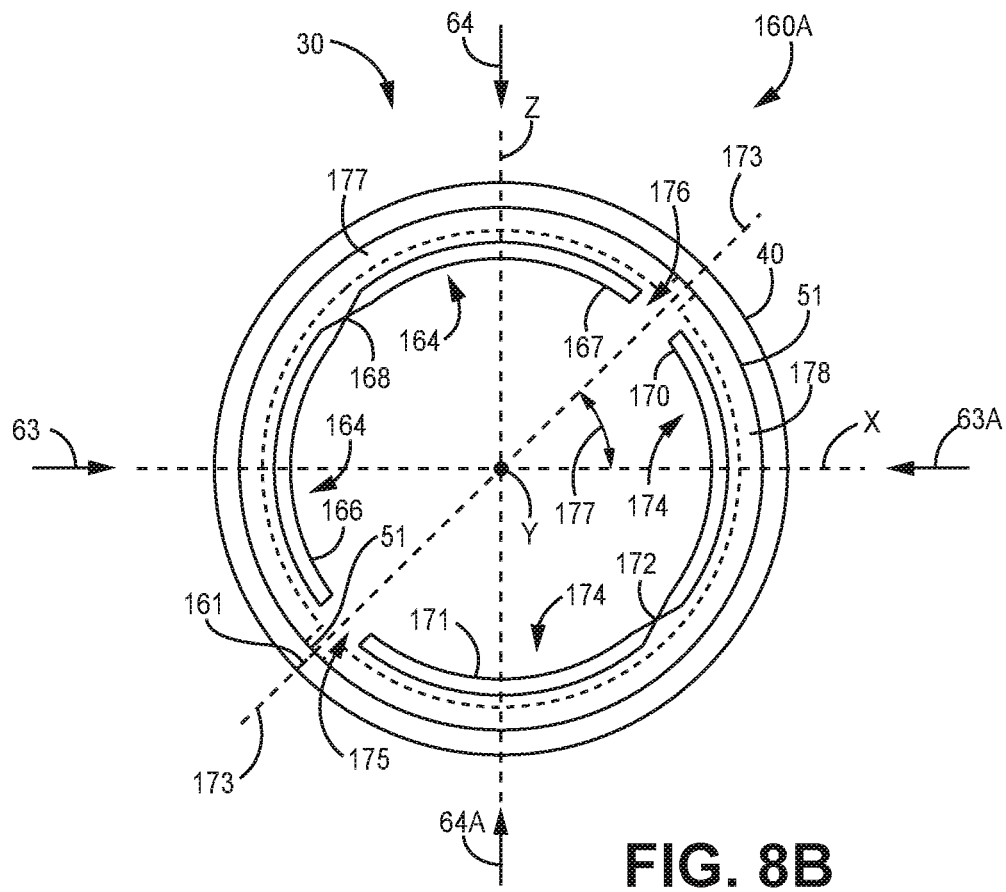
FIG. 8B is a cross-sectional view of an implantable medical device including the receive antenna configuration of FIG. 8A.

FIG. 8B is a cross-sectional view 160A of an example implantable medical device including the receive antenna configuration of FIG. 8A. View 160A illustrates device 30 as viewed from the perspective of a plane cutting through device 30 at a midpoint of antenna window 40 along the longitudinal axis 46 of device 30, wherein longitudinal axis is perpendicular to the plane cutting through the device. In view 160A as illustrated in FIG. 8B, device 30 is illustrated looking in a same direction as the direction of orientation of the Y-axis, with the X-axis extending in a left-right (horizontal) orientation, and the Z-axis extending in an up-down (vertical) orientation in the view.

The example of device 30 as shown in FIG. 8B includes first receive coil 164 and second receive coil 174 arranged along portions of the inner surface 51 of antenna window 40 in a same or similar manner as illustrated and described with respect to view 160 in FIG. 8A. As shown in view 160A, first loop 166 of first receive coil 164 is positioned along inner surface 51 of antenna window 40 so that the windings forming the first loop 166 extend to both sides of the X-axis along the side of the antenna window pointed to by arrow 63. Second loop 167 of first receive coil 164 is positioned along inner surface 51 of antenna window 40 so that the windings forming second loop 167 extend to both sides of the Z-axis along the side of the antenna window pointed to by arrow 64. The crossover area 168 of first receive coil 164 is positioned along the inner surface 51 at a point approximately mid-way between the X-axis and the Z-axis. As further shown in view 160A, first loop 170 of second receive coil 174 is positioned along inner surface 51 of antenna window 40 so that the windings forming the first loop 170 extend to both sides of the X-axis along the side of the antenna window pointed to by arrow 63A. Second loop 171 of second receive coil 174 is positioned along inner surface 51 of antenna window 40 so that the windings forming second loop 171 extend to both sides of the Z-axis along the side of the antenna window pointed to by arrow 64A. The crossover area 172 of second receive coil 174 is positioned along the inner surface 51 at a point approximately mid-way between the X-axis and the Z-axis.

In some examples, receive coils 164 and 174 are affixed directly to the inner surface 51 of antenna window 40. In some alternative examples, first receive coil 164 is affixed to ferrite sheet 177, and second receive coil 174 is affixed to ferrite sheet 178. The ferrite sheets 177 and 178, respectively, are then affixed to the inner surface 51 on the antenna window as shown in view 160A. Regardless of whether the ferrite sheets 177, 178 are included in a given example as illustrated in view 160A, or the receive coils 164, 174 are affixed directly to the inner surface 51, the outside extent of the loops forming each receive coil are positioned in close proximity to one another so that at least some portion of the windings forming the receive coils is provided around the Y-axis (longitudinal axis of device 30) for almost the entirety of three-hundred and sixty degrees around the inner surface 51.

For example, as shown in view 160A, the portion of first loop 166 of first receive coil 164 extending farthest away from crossover area 168 is positioned in close proximity to the portion of the second loop 171 of second receive coil 174 extending farthest away from crossover area 172. The arrangement leaves only a small gap 175, or in some examples no gap is required between the first loop 166 and the second loop 171 along axis 173. In some examples, some portion of first loop 166 touches some portion of loop 171, resulting in no gap between these coil loops. Similarly, the portion of second loop 167 of first receive coil 164 extending farthest away from crossover area 168 is positioned in close proximity to the portion of the first loop 170 of second receive coil 174 extending farthest away from crossover area 172. This arrangement leaves only a small gap 176, or in some examples no gap, between the second loop 167 and the first loop 170 along axis 173. In some examples, some portion of first loop 167 touches some portion of loop 170, resulting in no gap between these coil loops. With the exceptions of the gaps 175 and 176 if such gaps are present, the inner surface 51 includes some portion of the windings forming one of receive coils 164 and 174 surrounding the Y-axis of device 30.

The arrangement using two receive coils configured as infinity shaped coils as illustrated in views 160 and 160A provides a wide range of relative orientations between device 30 and magnetic field(s) imposed on device 30 the may result in a high level of inductive coupling efficiency between the imposed magnetic field(s) and receive coils 164 and/or 174. For example, any magnetic field having a magnet field direction lying in a plane that includes both the X-axis and the Z-axis (e.g., as illustrated by arrow 63, 63A, 64, 64A) may provide a high level of inductive coupling efficiency with one or both of receive coils 164, 174. In addition, variations in the angle of incidence of the magnetic fields that include magnetic fields having a magnetic field direction that intersects the plane containing the X-axis and the Z-axis of device 30 at some non-zero angle (e.g., non-perpendicular to the Y-axis) may also provide a high level of inductive coupling efficiency between the magnetic field(s) and one or both of receive coils 164 and 174. In addition, because this arrangement only requires two infinity loops of coil windings, only two sets of rectifier components, (e.g., tuning capacitor, diode), one set for each infinity loops, may be required to provide the additional components needed for the rectification circuitry associated with each coil. The reduced requirement for additional components may help reduce the real estate required for example on a hybrid circuit to perform these functions, and/or may help reduce the overall dimensions of the housing of the device where these infinity loop coils are located.

Figure 9A:
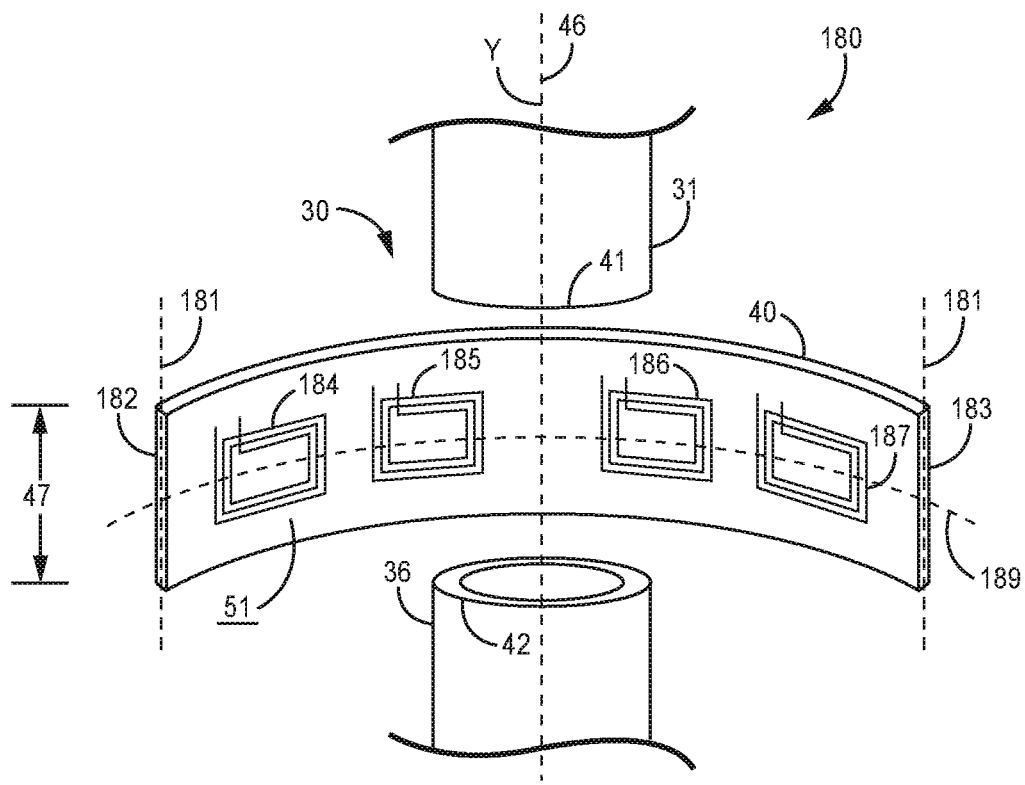
FIG. 9A illustrates a cutaway and exploded view of an example receive antenna configuration for an implantable medical device according to various examples described in this disclosure.

FIG. 9A illustrates a cutaway and exploded view 180 of an example receive antenna configuration for an implantable medical device according to various examples described in this disclosure. FIG. 9A includes an illustrative depiction of the antenna window 40 with a first housing portion 31 and a second housing portion 36 on opposite sides (top and bottom sides) of the antenna window 40. In FIG. 9A, antenna window 40 has been illustratively separated and moved away from first housing portion 31 at first seam 41 and illustratively separated and moved away for second housing portion 36 at second seam 42. In addition, antenna window 40 has been illustratively cut open along an illustrative axis 181 to form illustrative edges 182 and 183 along the cut line of axis 181. Edges 182 and 183 have been illustratively separated from one another to show inner surface 51 of the antenna window 40 depicted as a flat surface facing in an outward direction as viewed in FIG. 9A.

As shown in FIG. 9A, a first receive coil 184, a second receive coil 185, a third receive coil 186 and a fourth receive coil 187 are affixed to inner surface 51 of antenna window 40. Each of receive coils 184, 185, 186, and 187 comprises an individual electrical conductor formed into a flat spiral-wound coil having a pair of lead for coupling the coil to recharging circuitry of the device (not shown in FIG. 9A). Receive coils 184, 185, 186, and 187 may be examples of the receive coil 70 illustrated and described with respect to FIGS. 4A-4B. For example, as illustrated in FIG. 9A receive coils 184, 185, 186, and 187 may be formed using an electrical conductor, such as a multi-strand Litz wire. Receive coil 184, 185, 186, and 187 may be formed to have a generally rectangular shape the is "bent" to form a curvature that corresponds to the curvature of the inner surface 51 of antenna window 40. Receive coils 184, 185, 186, and 187 may be formed using any of the materials, winding formations, and techniques, or any combination thereof, as described for flat or spiral-wound planar coils as described throughout this disclosure, and any equivalents thereof.

Referring again to FIG. 9A, the curvature of the shape of receive coils 184, 185, 186, and 187 as represented by curve axis 189 allows the receive coils to be affixed to and assume the shape of the curvature of the inner surface 51 of antenna window 40. As previously described, the curvature of the inner surface 51 may encircle a cylindrical shaped interior cavity having a circular shape in cross-section. Receive coils 184, 185, 186, and 187 may in some examples be affixed directly to the inner surface 51 of antenna window 40. In some examples, receive coils 184, 185, 186, and 187 may be affixed to a first surface of a ferrite sheet or sheets, (not shown in FIG. 9A, but for example ferrite sheets 190, 191, 192, 193, respectively, as shown in FIG. 9B) wherein the ferrite sheet(s) are then affixed to inner surface 51 so that the ferrite sheet(s) is/are positioned between the receive coils, respectively, and the inner surface 51.

As shown in FIG. 9A, portions of the loops included in each individual winding forming receive coils 184, 185, 186, and 187, respectively, may extend to a height dimension within antenna window 40 that is nearly the height dimension 47 of the antenna window itself. In addition, the widthwise dimensions of the receive coils extends along the direction as the orientation of axis 189 that extends along inner surface 51 between first edge 182 and second edge 183. In some examples, the height and width dimensions over which the individual winding of the receive coils extend, respectively, may be substantially the same for each of the receive coils. The receive coils 184, 185, 186, and 187 may be positioned along axis 189 relative to one another so that only a small gap is provided, or no gaps exists, between the individual receive coils. As such, a large portion of the inner surface 51 around the entirety of the perimeter of inner surface 51 falls within areas over which at least one of the receive coils 184, 185, 186, and 187 extends. When the receive coils 184, 185, 186, and 187 are arranged within an antenna window of an implantable medical device as shown in FIG. 9A, the receive coils provide a wide range of relative angular orientations between magnetic fields imposed on the device and the device itself that may result in a high level of inductive coupling efficiency being achieved between the imposed magnetic fields and the receive coils, as further described below with respect to FIG. 9B.

Figure 9B:
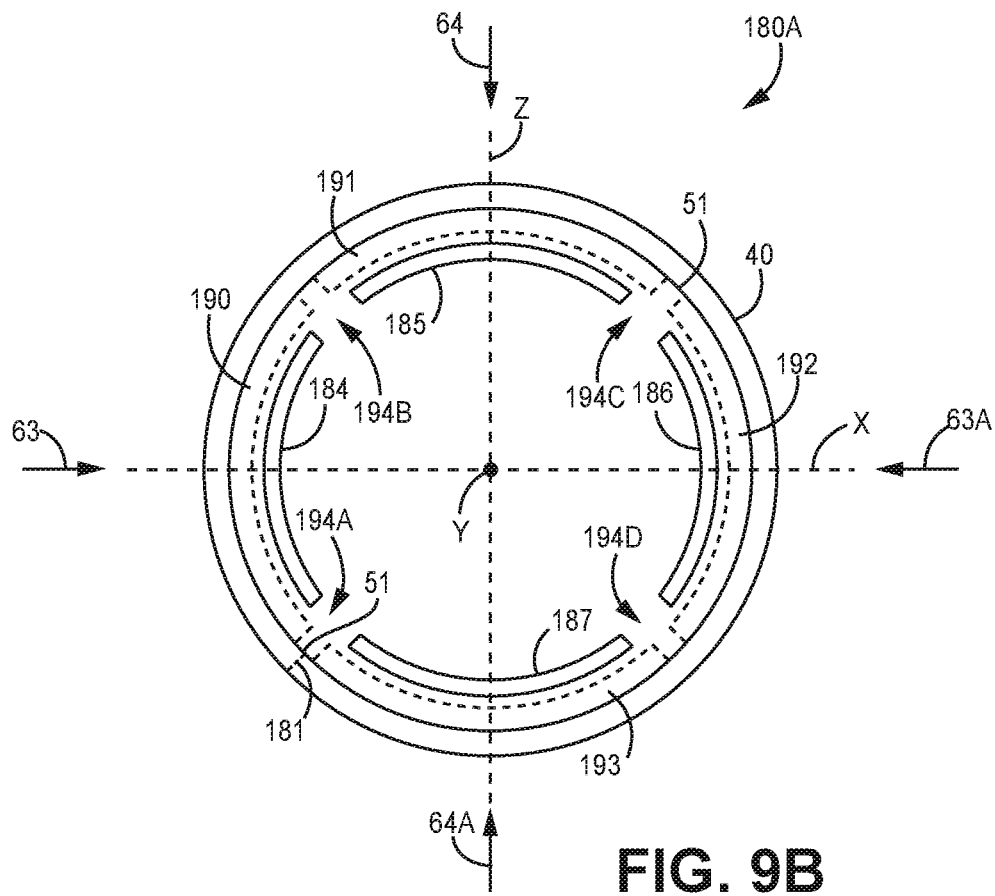
FIG. 9B is a cross-sectional view of an implantable medical device including the receive antenna configuration of FIG. 9A.

FIG. 9B is a cross-sectional view 180A of an implantable medical device including the receive antenna configuration of FIG. 9A. View 180A illustrates device 30 as viewed from the perspective of a plane cutting through device 30 at a midpoint of antenna window 40 along the longitudinal axis 46 of device 30, wherein longitudinal axis is perpendicular to the plane cutting through the device. In view 180A as illustrated in FIG. 9B, device 30 is illustrated looking in a same direction as the direction of orientation of the Y-axis, with the X-axis extending in a left-right (horizontal) orientation, and the Z-axis extending in an up-down (vertical) orientation in the view.

The example of device 30 as shown in FIG. 9B includes the receive coils 184, 185, 186, and 187 arranged along portions of the inner surface 51 of antenna window 40 in a same or similar manner as illustrated and described with respect to view 180 in FIG. 9A. As shown in view 180A, first receive coil 184 is positioned along inner surface 51 of antenna window 40 so that the windings forming the first receive coil extend to both sides of the X-axis along the side of the antenna window pointed to by arrow 63. Second receive coil 185 is positioned along inner surface 51 of antenna window 40 so that the windings forming the second receive coil extend to both sides of the Z-axis along the side of the antenna window pointed to by arrow 64. Third receive coil 186 is positioned along inner surface 51 of antenna window 40 so that the windings forming the third receive coil extend to both sides of the Z-axis along the side of the antenna window pointed to by arrow 63A. Fourth receive coil 187 is positioned along inner surface 51 of antenna window 40 so that the windings forming the fourth receive coil extend to both sides of the Z-axis along the side of the antenna window pointed to by arrow 64A.

In some examples, receive coils 184, 185, 186, and 187 are affixed directly to the inner surface 51 of antenna window 40. In some alternative examples, the receive coils 184, 185, 186, and 187 may be affixed to one or more ferrite sheet(s), wherein ferrite sheets are then affixed to the inner surface 51 so that the ferrite(s) are interposed between the inner surface 51 and the receive coils. As illustrated n FIG. 9B, first receive coil 184 is affixed to ferrite sheet 190, second receive coil 185 is affixed to ferrite sheet 191, third receive coil 186 is affixed to ferrite sheet 192, and fourth receive coil 187 is affixed to ferrite sheet 193. The ferrite sheets 190, 191, 192, and 193 are then affixed to the inner surface 51 on the antenna window as shown in view 180A. Regardless of whether the ferrite sheets 190, 191, 192, and 193 are included in a given example as illustrated in view 180A or the receive coils 184, 185, 186, and 187 are affixed directly to the inner surface 51, the outside extend of the loops forming each receive coils are positioned in close proximity to one another so that at least some portion of the windings forming the receive coils is provided around the Y-axis (longitudinal axis of device 30) for almost the entirety of three-hundred and sixty degrees around the inner surface 51.

For example, as shown in view 180A, a gap 194A is provided between first receive coil 184 and fourth receive coil 187, a gap 194B is provided between first receive coil 184 and second receive coil 185, a gap 194C is provided between second receive coil 185 and third receive coil 186, and gap 194D is provided between third receive coil 186 and fourth receive coil 187. The arrangement of receive coils may leave only a small gap between the receive coils at the radial positions indicated as gaps 194A-194D along inner surface 51. With the exception of these gaps, the inner surface 51 includes some portion of the windings forming one of receive coils 184, 185, 186, and 187 surrounding the Y-axis of device 30.

The arrangement using four receive coils configured as illustrated in views 180 and 180A provides a wide range of relative orientations between device 30 and magnetic field(s) imposed on device 30 the may result in a high level of inductive coupling efficiency between the magnetic field(s) and one or more of receive coils 184, 185, 186, and 187. For example, any magnetic field having a magnet field direction lying in a plane that includes both the X-axis and the Z-axis (e.g., as illustrated by arrow 63, 63A, 64, 64A) may provide a high level of inductive coupling efficiency with one more of receive coils 184, 185, 186, and 187. In addition, variations in the angle of incidence of the magnetic fields that include magnetic fields having a magnetic field direction that intersect the plane containing the X-axis and the Z-axis of device 30 at some none-zero angle, (e.g., non-perpendicular to the Y-axis) may also provide a high level of inductive coupling efficiency between the magnetic field(s) and one or more of receive coils 184, 185, 186, and 187.

In the examples of coil winding forming one or more of the receive coils of a receive antenna configuration as illustrated and described with respect to FIGS. 2A-9B, each of the coil windings is illustrated and described as being positioned within and enclosed by the housing of the device. However, examples of coils winding, such as the flat-wound, infinity shaped, and other multi-loop coils as described herein are not limed to coils winding positioned within the housing. In some examples, a coil winding, or portion of the coil winding, may be formed on an external surface of the housing, such being formed on an external surface of the first housing portion 31, the second housing portion 36, and/or the antenna window 40 of an implantable medical device such a s device 30. The external coil winding may include one or more flat spiral-wound coils, one or more infinity shaped coils, and/or a multi-loop coil such as three-loop coil, or any combination thereof. In some examples, the coil winding formed on an external surface of the device may be overmolded with a protective layer of material, such as polysulphone, to encapsulate the coil or embedded within the material used to form the housing, such as a polymeric material. In some examples, a portion of the housing where the external coil winding is formed may be recessed, for example forming a groove or trough, relative the other external surfaces of the housing of the device so that the coil windings may be formed within the groove or trough to provide additional physical protection to the coil windings.

FIG. 10 is a functional block diagram illustrating an example configuration of an intracardiac pacing device 15 according to various examples described in this disclosure. IMD 15 may correspond to any of IMD 15A and IMD 15B described and illustrated with respect to FIG. 1 and/or device 30/30A as described and illustrated with respect to FIGS. 2A-2B, or another IMD configured to be rechargeable using the devices, systems, and methods as described in this disclosure. IMD 15 includes a power source 204 that may be coupled to the electronic circuitry provided in IMD 15, and is configured to provide electrical power to these circuits. IMD 15 may be inductively rechargeable by imposing one or more magnetic fields onto IMD 15, wherein energy from these imposed field(s) may induce an electrical energy into antenna 209 coupled to communication circuitry 205 and to device recharging circuitry 206, or into an antenna 211 that may be provided in addition to antenna 209 and that when provided, is also coupled to recharging circuitry 206. When configured to be used for recharging IMD 15, antenna 209 and/or antenna 211 may be a receive antenna configuration according to any of the examples described in this disclosure, or any equivalents thereof. IMD 15 may be an example of a deeply implanted device, such as a device implanted within a chamber of the heart of a patient, and including a receive antenna as described in this disclosure that allows efficient recharging of a power source (e.g., power source 204) located within the IMD using a magnetic field imposed on the IMD to recharge the power source.

As shown in FIG. 10, device recharging circuitry 206 is coupled to power source 204, and may be coupled through switching device 210 to receive electrical energy induced in antenna 209 (or in antenna 211 when provided) by one or more electromagnetic fields imposed on the antenna, and to regulate the energy to provide a level of energy that is provided to power source 204 for the purpose of recharging power source 204 and/or powering the other circuitry included as part of IMD 15. Device recharging circuitry 206 may perform various energy conditioning functions to the energy inductively generated in antenna 209 (or antenna 211 when provided), for example by providing rectification, voltage level regulation, current level regulation, and/or other signal processing functions in order to generate the "recharging energy" provided to power source 204. Antenna 209 (and/or antenna 211 when provided) may be a multidirectional antenna that is not orientation specific with respect to the coupling efficiency of the inductive charging of power source 204 based on the orientation of the antenna relative to the orientation of the coil or coils providing the magnetic field(s) intended to recharge power source 204.

Thus, IMD 15 may be configured to couple magnetic energy captured by a receive antenna (including, but not necessarily a telemetry antenna), directed into a suitable rectifying circuit that delivers the electrical energy to an energy storage device such as a rechargeable battery. The switching device 210, which may be a transistor, may be included in IMD 15 and may be controlled, for example by processing circuitry 200, to select whether the telemetry or the power recharge system is active, and thus whether antenna 209 is coupled to the communication circuitry 205 or the device recharging circuitry 206. In other examples, the second antenna 211 is coupled directly to device recharging circuitry 206, and is configured to receive the inductively coupled energy provided to antenna 211, and to provide the inductively coupled energy to device recharging circuitry 206 to recharge power source 204.

In the illustrated example, IMD 15 includes processing circuitry 200 and an associated memory 201, sensing circuitry 202, therapy delivery circuitry 203, one or more sensors 207, and the communication circuitry 205 coupled to antenna 209 as describe above. However, IMD 15 need not include all of these components, or may include additional components. For example, IMD 15 may not include therapy delivery circuitry 203 in some examples of the device. Memory 201 includes computer-readable instructions that, when executed by processing circuitry 200, causes IMD 15 and processing circuitry 200 to perform various functions attributed to IMD 15 and processing circuitry 200 as described herein (e.g., preparing information for transmission from IMD 15 regarding a level of charge present in a power source, such as a battery management system information (BMS)). For example, processing circuitry 200 may be configured to provide information including a state of charge, and/or temperature information related to a battery, e.g., a battery located in IMD 15, determining a level of inductive coupling, e.g., energy level being generated in an antenna located in IMD 15 as a result of an electromagnetic field or fields being imposed on IMD 15, and generate information related to this inductively received energy for transmission by the communication antenna or separate antenna and associated power conditioning circuitry of IMD 15.

Memory 201 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital or analog media. Memory 201 may store threshold(s) for time of day, posture, heart rate, activity level, respiration rate, and other parameters. Memory 201 may also store data indicating cardiovascular pressure measurements, and store other data associated with cardiac and/or other physiological events associated with a patient.

Processing circuitry 200 may include fixed function circuitry and/or programmable processing circuitry. Processing circuitry 200 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 200 may include multiple components, such as any combination of one or more microprocessors, one or more controllers, one or more DSPs, one or more ASICs, or one or more FPGAs, as well as other discrete or integrated logic circuitry. The functions attributed to processing circuitry 200 herein may be embodied as software, firmware, hardware or any combination thereof.

As illustrated, sensing circuitry 202 and therapy delivery circuitry 203 are coupled to electrodes 212. Electrodes 212 as illustrated in FIG. 10 may correspond to, for example, electrodes located on leads 21 and 22 and/or the housing 23 of IMD 15A (FIG. 1), or electrodes 32 and 33 of device 30 (FIG. 2A) or device 30A (FIG. 2B). Sensing circuitry 202 in IMD 15 as shown in FIG. 10 may monitor signals from a selected two or more of electrodes 212 in order to monitor electrical activity of heart, impedance, or some other electrical phenomenon. Sensing of a cardiac electrical signal may be done to determine heart rates or heart rate variability, or to detect arrhythmias (e.g., tachyarrhythmias or bradycardia) or other electrical signals. In some examples, sensing circuitry 202 may include one or more filters and amplifiers for filtering and amplifying a signal received from electrodes 212.

In some examples, sensing circuitry 202 may sense or detect physiological parameters, such as heart rate, blood pressure, respiration, and other physiological parameters associated with a patient. The resulting electrical signals may be passed to cardiac event detection circuitry that detects a cardiac event for example when a cardiac electrical signal crosses a sensing threshold. The cardiac event detection circuitry may include a rectifier, filter and/or amplifier, a sense amplifier, comparator, and/or analog-to-digital converter. Sensing circuitry 202 may output an indication to processing circuitry 200 in response to sensing of a cardiac event (e.g., detected P-waves or R-waves).

In this manner, processing circuitry 200 may receive detected cardiac event signals corresponding to the occurrence of detected R-waves and P-waves in the respective chambers of heart. Indications of detected R-waves and P-waves may be used for detecting ventricular and/or atrial tachyarrhythmia episodes, e.g., ventricular or atrial fibrillation episodes. Some detection channels may be configured to detect cardiac events, such as P-waves or R-waves, and provide indications of the occurrences of such events to processing circuitry 200, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

Sensing circuitry 202 may also include switching circuitry to select which of the available electrodes 212 (or electrode polarities) are used to sense the heart activity. In examples with several electrodes 212, processing circuitry 200 may select the electrodes that function as sense electrodes, i.e., select the sensing configuration, via the switching circuitry within sensing circuitry 202. Sensing circuitry 202 may also pass one or more digitized EGM signals to processing circuitry 200 for analysis, e.g., for use in cardiac rhythm discrimination.

In the example of FIG. 10, IMD 15 includes one or more sensors 207 coupled to sensing circuitry 202. Although illustrated in FIG. 10 as included within IMD 15, one or more of sensors 207 may be external to IMD 15, e.g., coupled to IMD 15 via one or more leads, or configured to wirelessly communicate with IMD 15. In some examples, sensors 207 transduce a signal indicative of a patient parameter, which may be amplified, filtered, or otherwise processed by sensing circuitry 202. In such examples, processing circuitry 200 determines values of patient parameters based on the signals. In some examples, sensors 207 determine the patient parameter values, and communicate them, e.g., via a wired or wireless connection, to processing circuitry 200.

In some examples, sensors 207 include one or more accelerometers 208, e.g., one or more three-axis accelerometers. Signals generated by the one or more accelerometers 208 may be indicative of, as examples, gross body movement (e.g., activity) of the patient, patient posture, heart sounds or other vibrations or movement associated with the beating of the heart, or coughing, rales, or other respiration abnormalities. Accelerometers 208 may produce and transmit signals to processing circuitry 200 for a determination as to the posture of the patient. In various examples, signals from the accelerometers 208 are processed to determine an activity, such as when the patient is taking a step or steps, or for example when the patient is running, and used to provide an activity count associated with patient initiated physical activity of the patient. In some examples, sensors 207 may include sensors configured to transduce signals indicative of blood flow, oxygen saturation of blood, or patient temperature, and processing circuitry 200 may determine patient parameters values based on these signals. In various examples, sensors 207 may include one or a combination of sensor circuits 18 (FIG. 1) as previously described.

In some examples, processing circuitry 200 determines one or more patient parameter values based on pressure signals. Patient parameter values determined based on pressure may include, as examples, systolic or diastolic pressure values, such as pulmonary artery diastolic pressure values. In some examples, a separate device such as sensor circuits 18 (FIG. 1), include one or more sensors and sensing circuitry configured to generate a pressure signal, and processing circuitry 200 determines patient parameter values related to blood pressure based on information received from IMD 15.

Therapy delivery circuitry 203, when provided as part of IMD 15, may be configured to generate and deliver electrical therapy to the heart. Therapy delivery circuitry 203 may include one or more pulse generators, capacitors, and/or other components capable of generating and/or storing energy to deliver as pacing therapy, defibrillation therapy, cardioversion therapy, other therapy or a combination of therapies. In some instances, therapy delivery circuitry 203 may include a first set of components configured to provide pacing therapy and a second set of components configured to provide anti-tachyarrhythmia shock therapy. In other instances, therapy delivery circuitry 203 may utilize the same set of components to provide both pacing and anti-tachyarrhythmia shock therapy. In still other instances, therapy delivery circuitry 203 may share some of the pacing and shock therapy components while using other components solely for pacing or shock delivery.

Therapy delivery circuitry 203 may include charging circuitry, one or more charge storage devices, such as one or more capacitors, and switching circuitry that controls when the capacitor(s) are discharged to electrodes 212 and the widths of pulses. Charging of capacitors to a programmed pulse amplitude and discharging of the capacitors for a programmed pulse width may be performed by therapy delivery circuitry 203 according to control signals received from processing circuitry 200, which are provided by processing circuitry 200 according to parameters stored in memory 201. Processing circuitry 200 controls therapy delivery circuitry 203 to deliver the generated therapy to the heart via one or more combinations of electrodes 212, e.g., according to parameters stored in memory 201. Therapy delivery circuitry 203 may include switch circuitry to select which of the available electrodes 212 are used to deliver the therapy, e.g., as controlled by processing circuitry 200.

Communication circuitry 205 includes any suitable hardware, firmware, software or any combination thereof for communicating with another device, such as an external device 11, transceiver 16, or another IMD or sensors, such as sensor circuits 18, as shown in FIG. 1 and FIGS. 2A-2B. Referring again to FIG. 10, under the control of processing circuitry 200, communication circuitry 205 may receive downlink telemetry from and send uplink telemetry to external device 11 or another device with the aid of an antenna, such as antenna 209, which may be internal and/or external. In some examples, communication circuitry 205 may communicate with a local external device, for example through transceiver 16, and processing circuitry 200 may communicate with a networked computing device via the local external device and a computer network, such as the Medtronic® CareLink® Network developed by Medtronic, plc, of Dublin, Ireland.

As described above, in some examples (i.e., where a single receive/communication antenna is used) the antenna signal can be switched from the telemetry communication circuitry 205 to the recharging circuitry 206. In other examples the recharge antenna/coil or coils is/are separate from the communication/telemetry antenna. For example, antenna 209 may be switched between being coupled to communication circuitry 205 and device recharging circuitry 206 by switching device 210, wherein switching device 210 may be controlled by processing circuitry 200 to determine when antenna 209 is coupled to the communication circuitry 205 and when antenna 209 is to be coupled to the device recharging circuitry 206.

In various examples, processing circuitry 200 is coupled to device recharging circuitry 206, and receives information, such as a level of current, that is being induced in antenna 209 or antenna 211 as a result of electrical energy received by the antenna via magnetic energy imposed on IMD 15 for the purpose of recharging power source 204. Processing circuitry 200 may provide this and other information, for example charge rate and temperature information associated with the power source 204, in the form of an output signal to communication circuitry 205 for transmission from IMD 15 to one or more external devices, such as transceiver 16. This transmitted information may be used by the external device(s) to control one or more aspects of the recharging process.

For example, positioning of and/or a level of power being applied to a recharging coil or a pair of coils located externally to IMD 15 and generating the magnetic field or fields being imposed on IMD 15 may be controlled using this information transmitted from IMB 15. The setting of electrical parameters used to energize the coil of the pair of coils generating the magnetic field or fields imposed onto IMD 15 for the purpose of recharging the power source 204 may be controlled using this information transmitted from IMB 15. In addition, other information such as temperature and field intensity information transmitted from IMD 15, may be used to control the recharging process, for example by regulating the field strength being generated by the external coil(s), or for example to shut off the external coil(s) to stop the recharging process.

A clinician or other user may retrieve data from IMD 15 using external device 11 or another local or networked computing device configured to communicate with processing circuitry 200 via communication circuitry 205, for example through a transceiver such as transceiver 16. The clinician may also program parameters of IMD 15 using external device 11 or another local or networked computing devices. In some examples, the clinician may select patient parameters used to determine times of day and target activity levels to determine when to trigger taking measurements using sensors 207, accelerometers 208, and or via sensing circuitry 202.

In various examples, processing circuitry 200 is configured to receive signals from sensing circuitry 202, sensors 207 including accelerometers 208, and/or sensor signals provided by sensors external to IMD 15, to process these sensor signals to generate one or more input parameters based either directly on or derived from the sensor signals. The input parameters are associated with the value(s) for one or more physiological parameters associated with a patient, such as patient 12 where the IMD 15 may be implanted. The physiological parameters associated with the input parameters may include activity counts, respiration rates, breathing rates, movements, postures, and changes in postures associated with a patient. The values associated with these input parameters can be values measured directly from the input parameters or derived for these input parameters.

For example, a value of a heartrate, measured for example in heartbeats per minute or cardiac cycle length, may be determined as the current value (e.g., the most recent value) for the input parameter associated with the heart rate of the patient measured over some predefined time period. Similarly, a value of a breathing rate, measured for example in breaths per minute or breathing cycle length, may be determined as the current value (e.g., the most recent value) for the input parameter associated with the breathing rate of the patient as measured over some predefined time period.

Similarly, the values can be determined for other input parameters, such as activity count (e.g., based on movement of the patient measured for example in steps taken by the patient per minute), body temperature, and for example a current value for a posture of the patient (e.g., lying down, standing, sitting). A current value of a physiological parameter may be, in some examples, a mean or median of measured values over a period of time. These parameters may be used to monitor the physical condition of a patient, and/or to determine the efficacy of a therapy being applied to the patient, and/or the need to apply a new or different therapy, such as a new or different electrical stimulation therapy, to the patient based on analysis if the sensed parameters and/or instructions received by IMD 15 from one or more external devices.

Figure 11:
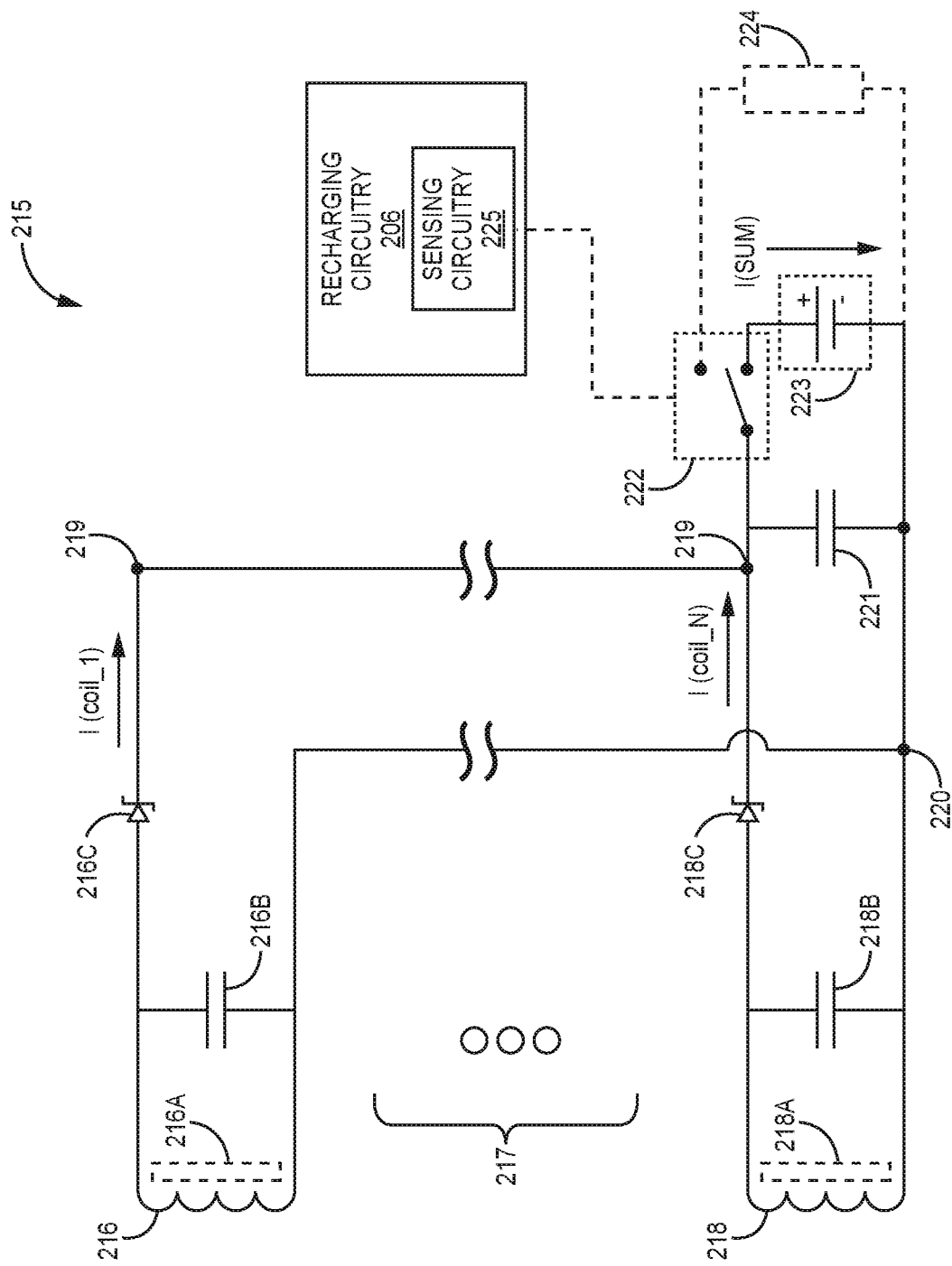
FIG. 11 is a schematic diagram including receive coils coupled to a rechargeable power source of an implantable medical device according to various examples described in this disclosure.

FIG. 11 illustrates a schematic diagram 215 including one or more receive coils couplable to a rechargeable power source 223 of an implantable medical device according to various examples described in this disclosure. The one or more receive antenna(s) and/or the additional circuitry illustrated in FIG. 11 may be representative of a receive antenna configuration that is included within or may be coupled to an implantable medical device such as IMD 15A or IMD 15B as shown in FIG. 1, or device 30/30A as shown in FIGS. 2A-2B, respectively. Schematic diagram 215 includes one or more receive coils 216, 218 that may be coupled to a rechargeable power source 223 through a switching device 222 that is controlled by recharging circuitry 206. In some examples, rechargeable power source 223 is power source 204, and recharging circuitry 206 is the circuitry illustrated and described with respect to IMD 15 in FIG. 10, and rechargeable power source 223 is configured to provide electrical power to the circuitry of an implantable medical device such as IMD 15 to allow the device to operate. The one or more receive coils 218, 218 may be examples of configurations of antenna 209 or antenna 211 as illustrated and described with respect to FIG. 10.

Referring to FIG. 11, receive coil 216 may be formed from an electrical conductor configured as a receive coil according to any of the receive coils described throughout this disclosure, or any equivalents thereof. For example, receive coil 216 may be a flat spiral-wound coil configured as or similar to receive coil 70 as illustrated and described with respect to FIGS. 4A-4B. In some examples, receive coil 216 may be an infinity shaped coil configured as or similar to receive coil 90 as illustrated and described with respect to FIGS. 5A-5C, dual-winding coil configuration 102 as illustrated and described with respect to FIG. 5D, or as a multi-loop infinity shaped coil as illustrated and described with respect to FIGS. 7A-7C. The schematic representation of receive coil 216 in FIG. 11 is illustrative of any of the types of receive coils described in this disclosure, and the equivalents thereof. For example, in configurations where receive coil 216 is arranged as an infinity shaped coil, the depiction of the windings of receive coil 216 as illustrated in FIG. 11 is intended to represent the plurality of loops and the crossover area(s) that may be included in the configuration of the receive coil.

Receive coil 216 as shown in FIG. 11 in some examples may be affixed to a ferrite sheet 216A. Receive coil 216 may be positioned along a curvature of an inner surface of an antenna window of a device, regardless of whether receive coil 216 is or is not also affixed to ferrite sheet 216A, for example as illustrated and described with respect to receive coil 55 in the examples illustrated and described with respect to FIGS. 3A-3B. Receive coil 216 may be configured as a flat spiral-wound coil that is positioned within the interior cavity of an implantable medical device, for example as illustrated and described with respect to receive coil 65 of device 30 in FIG. 3A or device 30A in FIG. 3B. The configuration of receive coil 216 in FIG. 11 as a flat spiral-wound coil may or may not include the receive coil being affixed to a ferrite sheet such as ferrite sheet 216A.

As shown in FIG. 11, a capacitor 216B is coupled in parallel with the receive coil 216. Capacitor 216B may be sized with respect to a capacitance value so that in conjunction with receive coil 216, a tank circuit is formed having a resonant frequency that matches a frequency that may be applied by externally generated magnetic field(s) imposed onto receive coil 216 for the purpose of inducing a current into receive coil 216. Having the tank circuit comprising receive coil 216 and capacitor 216A tuned to have a resonate frequency that matches a frequency of the magnetic field(s) intended to be imposed onto the receive coil 216 allows a higher level of coupling efficiency to be achieved between the imposed magnetic field(s) and the receive coil 216 when compared to other frequencies that are not matched to the resonate frequency of the tank circuit. A diode 216C is coupled in series with a first end of receive coil 216 and a terminal of the capacitor 216B. A second end of receive coil 216 is coupled to a common voltage node 220. Diode 216C in some examples is a Schottky diode. Diode 216C is configured to rectify any current flows illustratively represented by the arrow labeled "I (coil_1)" that are induced into receive coil 216 so that all current flows generated in the receive coil 216 as a result of externally imposed magnetic field(s) will flow through diode 216C in the direction indicated as "I (coil_1)," and toward node 219. In some examples, a minimum level of voltage is required to forward bias diode 216C, and therefore no current will be provided as current flow "I (coil_1)" until the minimum voltage level required to forward bias diode 216C is present, resulting in a minimum initial level of current flow being provided by the current induced into receive coil 216.

In examples where receive coil 216 is the only receive coil included in the system depicted by schematic diagram 215, the induced current provided by imposing externally generated magnetic field(s) onto receive coil 216 are provided to node 219 as the total amount of recharging current available for performing recharging of rechargeable power source 223. In other examples, additional receive coils may be included in the system depicted by schematic diagram 215. The addition receive coils may provide addition induced current(s) that may also be summed to together with the current from receive coil 216 and provided to node 219.

As shown in schematic diagram 215, the system illustrated in schematic diagram 215 may include a second receive coil 218. Second receive coil 218 may be configured using any of the configurations described above with respect to receive coil 216. Second receive coil 218 may be configured as flat spiral-wound coil, or as an infinity shaped coil having for example two or three loops. Second receive coil 218 may or may not be affixed to a ferrite sheet 218A. Second receive coil 218 may be positioned along the inner surface 51 of the antenna window 40 of the device, or may be positioned within the interior cavity of the device as described above with respect to receive coil 216. Second receive coil 218 may be coupled to a capacitor 218B and a diode 218C in a similar manner and in order to provide similar functionality as described above with respect to receive coil 216. For example, capacitor 218B may be sized with respect to a capacitance value so that in conjunction with receive coil 218, a tank circuit is formed having a resonant frequency that matches a frequency that may be applied by externally generated magnetic field(s) imposed onto receive coil 218 for the purpose of inducing a current into receive coil 218. In various examples, the resonate frequency of the tank circuit formed by second receive coil 218 and capacitor 218A is a same resonant frequency for the tank circuit formed by first receive coil 216 and capacitor 216B. As such, each of receive coils 216, 218 (and similarly any additional coils represented by dots 217) are configured to provide a maximum level of coupling efficiency for a given level of magnetic field intensity provided at the resonant frequency comparted to magnetic fields at the non-resonant frequencies. Second receive coil 218 may be configured to provide a current, illustratively represented by the arrow "I (coil_N)," to node 219 when a magnetic field or magnetic field(s) have sufficient magnetic field intensity is/are imposed onto receive coil 218.

In various examples, the system illustrated in schematic diagram 215 may include more than two receive coils. The additional coils are illustratively represented by the "dots" generally indicated by bracket 217. In such examples, the individual additional receive coil(s) may be arranged using any of the coil configurations and positioning configurations as described above with respect to receive coils 216 and 218, and may include the additional devices such as the capacitor and diode coupled to each of these additional coils, respectively, in a same or similar manner as described above with respect to the capacitors and diodes associate with receive coils 216 and 218.

Configurations of the system illustrated in schematic diagram 215 having two or more of the coils is configured in a same coil configuration, such as two or more flat spiral-wound coils, or two or more infinity shaped coils. Configuration of the system illustrated in schematic diagram 215 having two or more receive coils are not limited to having receive coils configured only or all in a same coil configuration, such as a same flat spiral-wound or a same infinity shaped coil configuration for each coil. In some examples, at least one of the receive coils may be configured in a first configuration, such as a flat spiral-wound configuration, wherein at least one addition receive coil is configured as an infinity shaped coil (e.g., coils 65 and 55, respectively, as illustrated and described in FIG. 3B). For systems that include two or more receive coils, any current generated in a given one of the coils in an amount that provides a current flow to node 219 may be summed to together to provide the total recharging current indicated as "I (SUM)."

As shown in FIG. 11, a smoothing capacitor 221 may be coupled between node 219 and the common voltage node 220 to smooth out any rapid variations in the current provided to node 220. The power source 223 that is to be recharged using the "I (SUM)" current is coupled to node 219 through switching device 222. Switching device 222 is not limited to any particular type of device, and in some examples, may be a semiconductor device, such as a transistor, that is controlled by recharging circuitry 206. When switching device 222 is operated to couple node 219 to power source 223, current flows provided by the receive coil(s) to node 219 may be provided to a first terminal of power source 223 through switching device 222. A second terminal of power source 223 is coupled to the common voltage node 220. When coupled to node 219, the flow of current flow to the first terminal of power source 223 provides a source of electrical energy to recharge power source 223. In various examples, recharging circuitry 206 is configured to control the coupling of node 219 to power source 223 by controlling switching device 222, and thus regulate and control the rate and intervals during which power source 223 receives the current flow from node 219.

Recharging circuitry 206 may include sensing circuitry 225. Sensing circuitry 225 may include sensors and sensor processing circuitry (not shown in FIG. 11) configured for example to sense one or more parameters associated with the operation of the devices illustrated in FIG. 11. For example, sensing circuitry 225 may include one or more sensors configured to sense a level of current flow being provided by one or more of receive coils 216, 218, and 217 (if provided). Sensing circuitry 225 may include one or more sensors configured to sense a level of current flow being provided to power source 223 as current "I (SUM). Sensing circuitry 225 may also include one or more sensors configured to sense other parameters, such as the temperature of power source 223 and/or a temperature within the device where the receive coils, recharging circuitry 206, and power source 223 are located. Recharging circuitry 206 may be configured to receive electrical signals and/or data derived from the electrical signals that are sensed using sensing circuitry 225, and to control the recharging of power source 223 based at least in part of these sensed signal and/or the information derived from these sensed signals.

Sensing circuitry 225 may include on or more sensors configured to measure a voltage level and/or a level of recharge present at power source 223. Electrical signals and/or information derived from electrical signals sensed by sensing circuitry 225 that indicate of the voltage level and/or a level of recharging that has been competed relative to power source 223 may also be utilized by recharging circuitry 206 as a basis for controlling the recharging of power source 223. For example, recharging circuitry may utilize these signals and/or information derived from these signals as a basis by to regulate the current being provided to power source 223 from node 219 by controlling the coupling provided between node 219 and power source 223 through switching device 222.

In some examples, a shunt device 224, which may comprise an electrically resistive load, may be coupled to switching device 222 such that switching device 222 may couple the shunt device 224 to node 219. The coupling of shunt device 224 to node 219 may be utilized to dissipate the current, and thus the energy being imposed on coil 216, 218, and 217 (when provided), at various times when recharging circuitry 206 determines that recharging current is not to be applied to power source 223 but wherein a recharging current is being induced into one or more of the coils. In some examples, recharging circuitry 206 may disconnect the coupling between node 219 and power source 223 when a determination is made that the recharging of power source 223 should be terminated, either on a temporary or a permanent basis. When not coupling node 219 to power source 223, recharging circuitry 206 and switching device 222 may be configured to optionally couple or not couple shunt device 224 to node 219.

Figure 12:
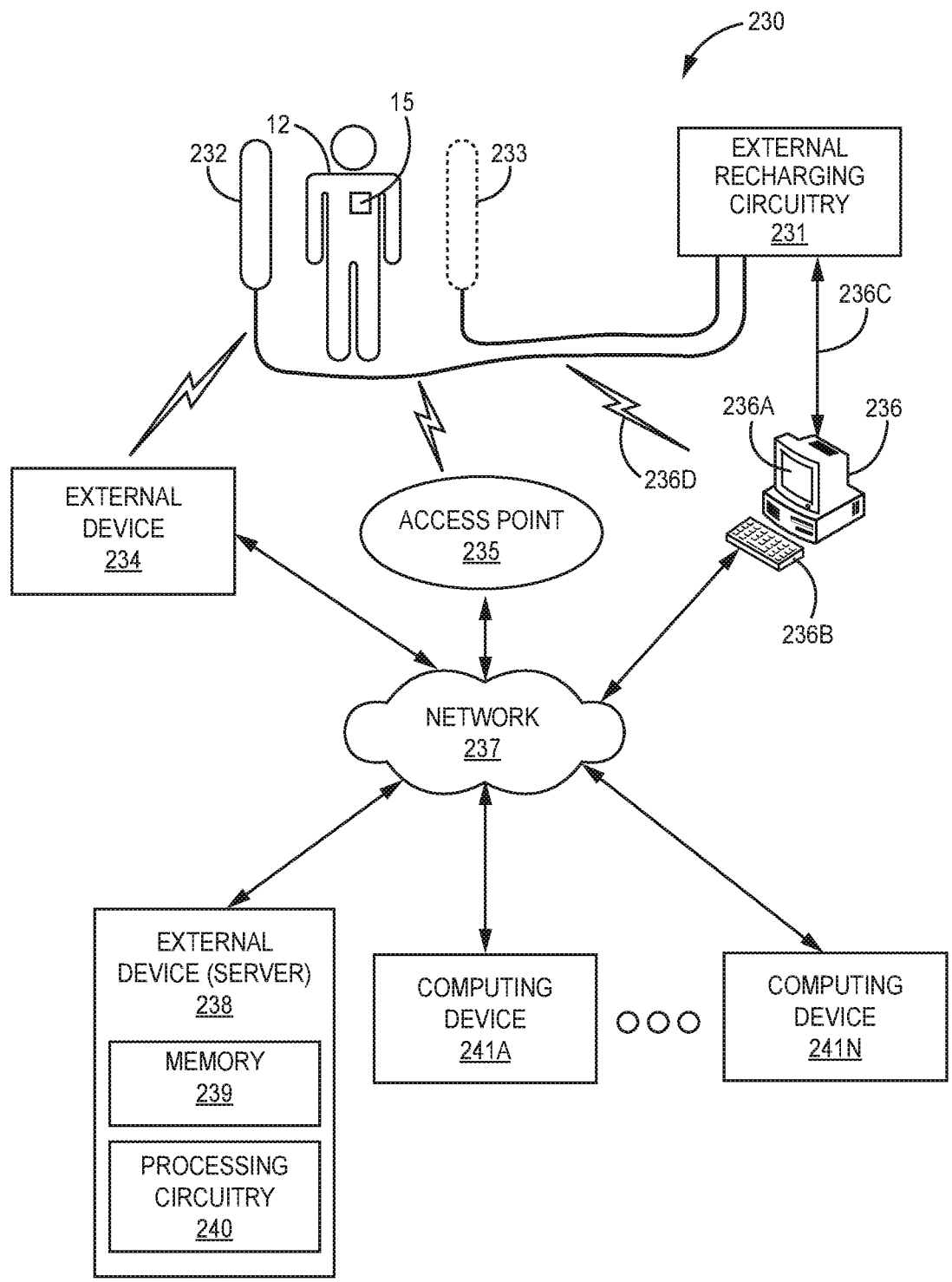
FIG. 12 is a functional block diagram illustrating an example configuration of a system for inductive recharging of an implantable medical device according to various examples described in this disclosure.

FIG. 12 is a functional block diagram illustrating an example configuration of a system 230 for inductive recharging of an implantable medical device 15 according to various examples described in this disclosure. System 230 includes external recharging circuitry 231 electrically coupled to a single recharging coil 232 in some examples, or a pair of recharging coils comprising first coil 232 and second coil 233 in some examples, the recharging coil or coils located externally to a patient 12 having an implanted IMD 15 according to the various examples described in this disclosure. In some examples, a single coil 232 may be a flat planar coil arranged to be placed proximate to, and in some examples in direct contact with patient 12 in an area adjacent to IMD 15. Single coil 232 may be electrically energized and configured to provide a time-varying magnetic field that may be imposed on an implanted medical device, such as IMD 15 illustratively represented as being implanted in patient 12, for the purpose of recharging a power source within the IMD. In some examples, coil 232 may be arranged as a first coil of a pair of coils including a second coil 233, the pair of coils 232, 233 physically arranged so that when the coils are electrically energized, a time-varying magnetic field is generated between the coils that may be imposed on an implanted medical device, such as IMD 15, for the purpose of recharging a power source within the IMB. In some examples, coils 232 and 233 may be physically arranged and electrically configured as a Helmholtz coil. The arrangement of coil 232 and/or coils 232 and 233 relative to patient 12 and IMD 15 as shown in FIG. 12 is not necessarily intended to be illustrative of the actual arrangement, for example with respect to positioning and/or scale of the coil 232 or the pair of coils 232 and 233, and patient 12/IMD 15 during a period of time when recharging of IMD 15 is occurring, and is intended to be illustrative of various features of example system 230.

As shown in FIG. 12, coil 232 (and coil 233 when provided), are coupled to recharging circuitry 231. Recharging circuitry 231 includes various electrical devices arranged to provide and to control the electrical energization of coil 232, and/or coil pair 232/233, in order to generate a time-varying magnetic field or fields that may be imposed onto IMB 15 when IMB is positioned proximate to coil 232 or between coil pair 232/233. In various examples, IMD 15 includes a receive antenna located within or coupled to the IMD, the receive antenna configuration arranged as an example of any of the receive antenna configurations described in this disclosure, or any equivalents thereof. The receive antenna arrangements may be configured to generate at least a minimum level of induced current in one or more of the receive coils of the receive antenna configuration regardless of the direction of orientation of the magnetic field generated by coil 232 and/or coils 232/233 imposed on IMD 15 and for a given magnetic field intensity applied to the IMD by the imposed magnetic field(s). As such, an elaborate system of alignment equipment and/or additional and more complex coil alignment procedures may not be required in order to achieve an acceptable level of inductive coupling efficiency between the magnetic field imposed on IMD 15 and the receive antenna configuration of the IMD regardless of the orientation of IMD 15 relative to the direction of the imposed magnetic field.

For example, when recharging a power supply located within IMD 15 while IMD 15 is implanted within patient 12, a single coil 232 may be placed in a position proximate to IMD 15 and external to patient 12, for example covering and/or in contact with an area of patient 12, such as the chest of the patient, adjacent to where IMD 15 has been implanted. IMD 15 in some examples may be considered to be a deeply implanted device, for example a device implanted within a chamber of the heart of patient 12. When positioned as described above, coil 232 may be energized to generate a time-varying magnetic field that extends away from coil 232 and is imposed onto IMD 15 and the multi-axis antenna located within IMD 15. Because the receive antenna configuration of IMD 15 is at least somewhat non-directional, a precise alignment of the direction of the imposed magnetic field relative to an orientation of IMD 15 and the receive antenna configuration is not critical or required, and may be a random relative orientation.

Despite such a random relative orientation, at least a minimum level of recharging current may be induced into the receive antenna configuration of IMD 15 for a given level of magnetic field intensity being provided by coil 232. The lack of a requirement for a precise or a particular alignment between the magnetic field and the orientation of the IMD 15 may allow for efficient and rapid recharging of the power source of the IMD without the need for a complex alignment procedure to be performed, and/or without the need for complex alignment apparatus to be provided and operated to align coil 232 and IMD 15. In some examples, simply positioning coil 232 as a single coil proximate to the area of IMD 15, for example laying across an area of the chest of the patient 12 in the area of implantation of IMD 15, is adequate to allow an efficient level of inductive coupling between the magnetic field generated by coil 232 and the receive antenna configuration of the IMD.

In a similar manner, when using a pair of coils 232 and 233 for recharging a power source of IMD 15, the relative alignment of a direction of a magnetic field generated in the area between the coils 232, 233 and the orientation of IMD 15 may not be critical with respect to achieving an efficient level of inductive coupling between the magnetic field and the receive antenna configuration of the IMD. When IMD 15 is positioned in the area between coil pair 232, 233, the coil pair may be energized to generate a time-varying magnetic field extending between the pair of coils, and that may be imposed onto IMD 15 and the receive antenna configuration located within IMD 15. Use of the coil pair 232, 233 may provide a more uniform magnetic field throughout the area between the coils, and thus further reducing or eliminating the need to determine a particular positioning of IMD 15 relative to the position of coils 232, 233 while still providing an efficient level of inductive coupling for inducing a recharging current into the receive antenna configuration of the IMD. Further, because the receive antenna configuration is these example IMDs is somewhat non-directional, an alignment of the direction of the imposed magnetic field generated between coil 232, 233 relative to an orientation of IMD 15 and the receive antenna configuration may not be critical, and may be a random relative orientation. Despite this random relative orientation, at least a minimum level of recharging current may be induced into the receive antenna configuration of IMD 15 for a given level of power being provided by the pair of coils 232 and 233.

The lack of a requirement for a precise or a particular alignment between the magnetic field generated by coil pair 232, 233 and the orientation of the IMD 15 may allow for efficient and rapid recharging of the power source of the IMD without the need for a complex alignment procedure to be performed, and/or without the need for complex alignment apparatus to be provided and operated to align coil pair 232, 233 and IMD 15. In some examples, simply positioning IMD 15 within the area between coils 232, 233, for example by positioning coils 232 and 233 on opposite sides of patient 12 so that the longitudinal axis common to both coils aligns with IMD 15, is adequate to allow an efficient level of inductive coupling between the magnetic field generated by the pair of coils 232, 233 and the receive antenna configuration of the IMD. The use of the pair of coils 232, 233 may further simply the requirement for positioning of IMD 15 relative to the coil pair, and the relative level of uniformity of the magnetic field provided between coils 232 and 233 may allow for simply positioning the IMD somewhere in the area between the coils, and energizing the coil pair to achieve an efficient level of inductive coupling between the magnetic field and the receive antenna configuration of the IMD.

Recharging circuitry 231 may be coupled to a computing device 236 that includes a display 236A and one or more input devices 236B, such as a keyboard and/or a computer mouse, that allow a user to interact with recharging circuitry 231 through computing device 236. Computing device 236 may be communicatively linked to recharging circuitry 231 by a wired connection 236C, and/or by a wireless connection 236D. In various examples, computing device 236 is configured to allow a user, such as a physician or a technician (neither shown in FIG. 12), to operate and control recharging circuitry 231 during a recharging session performed on IMD 15. Further, feedback received from IMD 15, for example received by computing device 236, may be used to control and adjust various aspects of recharging circuitry 231, including adjusting the field strength of the magnetic field being imposed on IMD 15, and controlling the duration of the recharging process.

Feedback from IMD 15 in some examples comprises a value for the level of current that is being induced in the receive coil of IMD 15 through the inductive coupling of the energy being provided by coil 232, or by coil pair 232 and 233. Other information provided by IMD 15, such as temperature, rate of charge, and percentage of charge information generated by IMD 15 may be transmitted from IMD 15 to computing device 236 or other external devices, and use by recharging circuitry 231 to control the energization of coils 232 and 233, and/or to determine when to terminate and/or regulate the power level being applied to the recharging process being performed by recharging circuitry 231 on IMD 15.

System 230 further includes external computing devices, such as a server 238 and one or more other computing devices 241A-241N, that may be communicatively coupled to IMD 15, computing device 236, and/or external device 234 via a network 237. In this example, IMD 15 may use its communication circuitry, at different times and/or in different locations or settings, to communicate with external device 234 via a first wireless connection, and/or to communicate with an access point 235 via a second wireless connection. In the example of FIG. 12, computing device 236, access point 235, external device 234, server 238, and computing devices 241A-241N are interconnected, and able to communicate with each other, through network 237.

Access point 235 may comprise a device that connects to network 237 via any of a variety of connections, such as telephone dial-up, digital subscriber line (DSL), or cable modem connections. In other examples, access point 235 may be coupled to network 237 through different forms of connections, including wired or wireless connections. In some examples, access point 235 may be co-located with the patient. Access point 235 may interrogate IMD 15, e.g., periodically or in response to a command from the patient or from network 237, to retrieve physiological measurements and/or other operational or patient data from IMD 15. Access point 235 may provide the retrieved data to server 238 via network 237. In various examples, access point 235 may be any examples of transceiver 16 described above.

In some cases, server 238 may be configured to provide a secure storage site for data that has been collected from IMD 15, from recharging circuitry 231, and/or from external device 234. In some cases, server 238 may assemble data in web pages or other documents for viewing by trained professionals, such as clinicians, via computing devices 241A-241N. The illustrated system 230 of FIG. 12 may be implemented, in some aspects, with general network technology and functionality similar to that provided by the Medtronic® CareLink® Network developed by Medtronic plc, of Dublin, Ireland.

In some examples, one or more of computing device 236, access point 235, server 238, or computing devices 241A-241N may be configured to perform, e.g., may include processing circuitry configured to perform, some or all of the techniques described herein, e.g., with respect to processing circuitry of IMD 15 and external device 234, relating to the recharging of power source located within IMD 15. In the example of system 230 as shown in FIG. 12, server 238 includes a memory 239, which may be configured to store physiological and other data received from IMD 15 and/or external device 234, and processing circuitry 240, which may be configured to provide some or all of the functionality ascribed to processing circuitry of IMD 15 as described herein. For example, processing circuitry 240 may provide programming and/or parameters that are used by recharging circuitry 231 that may be used in the process of providing inductive recharging to a power source located within IMD 15.

Figure 13:
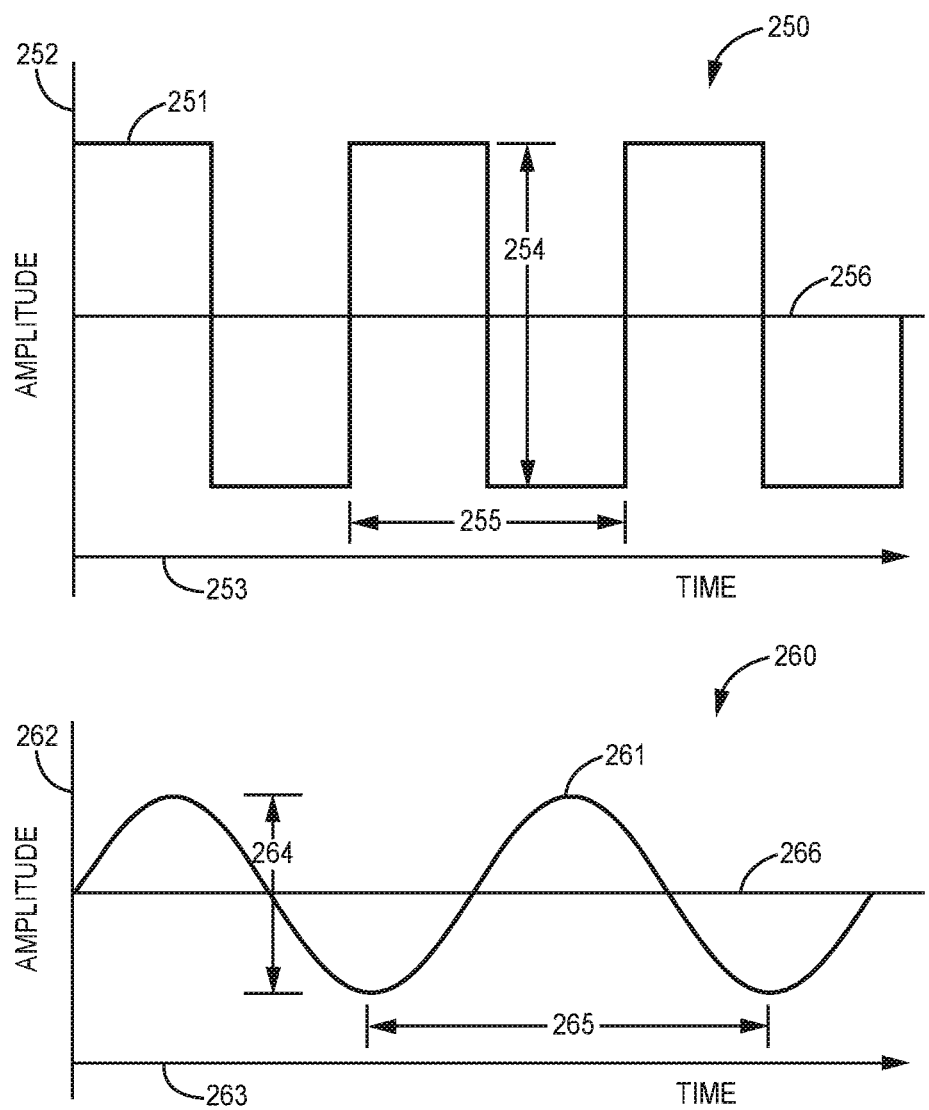
FIG. 13 illustrates graphs of representative waveforms that may be generated by a signal generator and applied to the recharging coil or coils of a recharging system according to various examples described in this disclosure.

FIG. 13 illustrates graphs 250, 260 of representative waveforms 251, 261 that may be generated by a signal generator and applied to the recharging coil or coils of a recharging system according to various examples described in this disclosure. The representative waveforms 251, 261 may be generated by a signal generator, such as signal generator included in recharging circuitry 231 as illustrated and described with respect to FIG. 12, and applied to the coil (e.g., coil 232, or a pair of coils 232 and 233 of FIG. 12), coupled to recharging circuitry according to various examples described in this disclosure. In FIG. 13, graph 250 illustrates the example waveform 251 of a square wave having an amplitude value plotted against the vertical axis 252 over time, time represented by horizontal axis 253.

Waveform 251 comprises a peak-to-peak amplitude 254, and a cycle period 255. In various examples, the peak-to-peak amplitude 254 of waveform 251 may comprise a voltage range of 10 mV to 100 volts, in some examples, 5 volts. The peak-to-peak amplitude in some examples is dependent on the power amplifier selected that the waveform 251 is being provided to in order to generate the output used to energize one coil or a pair of electrical coils arranged as recharging coils in a recharging system.

In some examples, the power amplifier being driven by the waveform 251 is a fixed amplification power amplifier, capable of providing a 400-Watt output signal based on a variable input signal having a peak-to-peak amplitude 10-200 mV. In some examples, a reference voltage level 256 may comprise a zero-volt reference voltage, wherein a portion of waveform 251 is provided at voltage level that is a higher voltage than the reference voltage 256, and a portion of waveform 251 is provided at a voltage level that is less than the reference voltage level 256. In various examples, the duty cycle of waveform 251 over period 255 provides a fifty-percent duty cycle. In various examples, the duty cycle of waveform 251 over the period 255 provides a duty cycle other than a fifty-percent duty cycle. In various examples the time period 255 of waveform 251 is in a range of 100 microseconds to 100 nanoseconds, representative of a frequency range of 10 kHz to 10 MHz for waveform 251.

In some examples, an electrical voltage having a waveform corresponding to waveform 251 may be applied to a single recharging coil to generate a magnetic field that may be imposed on a receive antenna configuration of an implanted medical device to induce a recharging current into the receive antenna configuration for the purpose of recharging a power source of the implanted medical device. The receive antenna configuration may be any of the examples of the receive antenna configurations described throughout this disclosure configured to provide at least a minimum level of recharging current for a given energy level associated with the imposed magnetic field regardless of the orientation of the direction of the magnetic field generated by the single recharging coil relative to the orientation of the implanted medical device.

In some examples, an electrical voltage having a waveform corresponding to waveform 251 may be applied to a pair of coils to generate a generally uniform magnetic field between the pair of coils that may be imposed on a receive antenna configuration of an implanted medical device positioned in an area between the pair of coils. The uniform magnetic field may be used to induce a recharging current into the receive antenna configuration for the purpose of recharging a power source of the implanted medical device. The receive antenna configuration may be any of the examples of the receive antenna configurations described throughout this disclosure configured to provide at least a minimum level of recharging current for a given energy level associated with the imposed magnetic field regardless of the orientation of the direction of the uniform magnetic field generated by the pair of coils relative to the orientation of the implanted medical device.

In some examples, electrical energy having the same electrical parameters such as amplitude, duty cycle, and phase for waveform 251 is applied to each of the pair of coils being utilized as the recharging coils. Other and/or different combinations of differences between the electrical parameters of waveform 251 applied to the first electrical coil and at a same time to the second electrical coil is not limited to variation of the amplitude 254 of the waveforms, and may include other variation, such as differences in the duty cycle of the waveforms applied for example to the first coil compared to a duty cycle of the waveform that is applied to the second electrical coil.

Graph 260 illustrates an example waveform 261 of a sinusoidal waveform having a varying amplitude value plotted against the vertical axis 262 over time, time represented by horizontal axis 263. Waveform 261 comprises a peak-to-peak amplitude 264, and having a period 265. In various examples, the peak-to-peak amplitude 264 of waveform 261 may comprise a voltage range of 10 mV to 100 volts, in some examples, 5 volts. The peak-to-peak amplitude in some examples is dependent on the desired peak magnetic field intensity and the capacity of the power amplifier employed. In some examples, the power amplifier being driven by waveform 261 is a fixed 400-Watt power amplifier, in other example the power amplifier comprises a variable output between 2 Watt and 1 kW. In some examples, a reference voltage level 266 may comprise a zero-volt reference voltage, wherein a portion of waveform 261 provides a voltage level above the reference voltage level 266, and another portion of each cycle of waveform 261 comprises voltage value that is below the reference voltage level 266. In various examples, the duty cycle of waveform 261 over period 265 provides a fifty-percent duty cycle of voltage levels above the reference voltage level 266. In various examples the time period 265 of waveform 261 is in a range of 100 microseconds to 100 nanoseconds, representative of a frequency range of 10 kHz to 10 MHz for waveform 261.

In some examples, an electrical voltage having a waveform corresponding to waveform 261 may be applied to a single recharging coil to generate a magnetic field that may be imposed on a receive antenna configuration of an implanted medical device to induce a recharging current into the receive antenna configuration for the purpose of recharging a power source of the implanted medical device. The receive antenna configuration may be any of the examples of the receive antenna configuration described throughout this disclosure configured to provide at least a minimum level of recharging current for a given energy level associated with the imposed magnetic field regardless of the orientation of the direction of the magnetic field generated by the single recharging coil relative to the orientation of the implanted medical device.

In some examples, an electrical voltage having a waveform corresponding to waveform 261 may be applied to a pair of coils to generate a generally uniform magnetic field between the pair of coils that may be imposed on a receive antenna configuration of an implanted medical device positioned in an area between the pair of coils. The uniform magnetic field may be used to induce a recharging current into the receive antenna configuration for the purpose of recharging a power source of the implanted medical device. The receive antenna configuration may be any of the examples of the receive antenna configurations described throughout this disclosure configured to provide at least a minimum level of recharging current for a given energy level associated with the imposed magnetic field regardless of the orientation of the direction of the uniform magnetic field generated by the pair of coils relative to the orientation of the implanted medical device.

In some examples, electrical energy having the same electrical parameters such as amplitude, duty cycle, and phase for waveform 261 is applied to each of the pair of coils being utilized as the recharging coils. Other and/or different combinations of differences between the electrical parameters of waveform 261 applied to the first electrical coil and at a same time to the second electrical coil is not limited to variation of the amplitude 264 of the waveforms, and may include other variation, such as differences in the phases of the waveforms applied for example to the first coil compared to the second coil.

Figure 14:
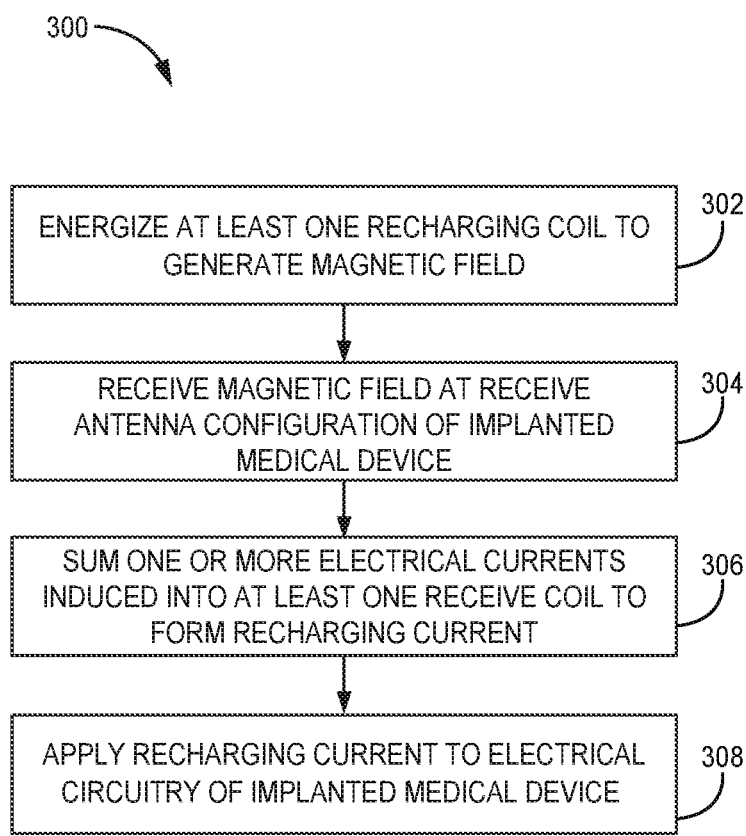
FIG. 14 is a flowchart illustrating a method according to various examples described in this disclosure.

FIG. 14 is a flowchart illustrating a method 300 according to various examples described in this disclosure. Method 300 includes recharging a power source located in an implanted medical device 30 implanted within a patient. Method 300 also contemplates providing electrical energy to power and operate an implanted medical device through inductive coupling of electrical energy from magnetic fields generate externally from the implanted device to the receive antenna configuration within the implanted device. Method 300 is described as being performed by system 230 as illustrated and described with respect to FIG. 12, the recharging process performed on implantable medical device 30 having a receive antenna configuration located within the device as illustrated and described with respect to any of FIGS. 2A-9B. However, method 300 is not limited to being performed examples of system 230 performing the recharging process on an implanted medical device, and method 300 is not limited to recharging processes performed on examples of device 30. Other devices having examples of the receive antenna configurations as described throughout this disclosure, and any equivalents thereof, that are configured to have recharging currents induced into the antenna for the purpose of recharging a power source of the implanted medical device are contemplated by the processes of method 300.

Method 300 includes an external recharging circuitry 231 of system 230 energizing at least one recharging coil, e.g., coil 232 or a pair of coils 232, 233, to generate a magnetic field (block 302). In instances where the recharging coil of the external recharging circuitry is a single recharging coil, such as coil 232, the recharging coil may be a flat spiral-wound planar coil according to any of the examples described throughout this disclosure. In instances where the recharging coil comprises a pair of coils, such as coils 232 and 233, the pair of coils may be physically arranged and electrically energized according to any of the pairs of coils described throughout this disclosure, including coils 232 and 233 arranged to form a Helmholtz coil.

Method 300 includes receiving the generated magnetic field(s) at a receive antenna configuration of the implanted medical device 30 (block 304). In some examples, the implanted medical device includes a rechargeable power source, such as battery 39 (FIGS. 2A-2B), which is to be recharged using electrical energy induced into the receive antenna configuration of the implanted medical device by the imposed magnetic fields. In some examples, the implanted medical device is configured to power the electrical circuitry of the implanted medical device using electrical energy induced into the receive antenna configuration of the device in order to operate the implanted medical device. In some examples where a single recharging coil is being utilized to generate the magnetic field, imposing the magnetic field onto the receive antenna configuration of the implanted medical device 30 includes placing the recharging coil proximate to, and in some examples in contact with, an exterior area or surface of the patient having the implanted medical device to be recharged adjacent to the location of the implanted device. In some examples where a pair of coils is being utilized to generate the magnetic field, imposing the magnetic field onto the multi-axis antenna may include positioning the patient, and thus the implanted medical device 30, within an area located between the pair of coil 232, 233.

The receive antenna configuration may include any of the examples of a receive coil as described throughout this disclosure, and may include a combination of two or more of the receive coils as described in this disclosure, that are configured to generate induced current(s) in the receive coil(s) when magnetic fields are imposed on the receive coil(s), and to provide the generated electrical currents to additional circuitry of the implanted medical device.

The receive antenna configuration in some examples of method 300 includes at least one receive coil comprising an electrical conductor forming a coil winding, the coil winding positioned within an interior cavity enclosed by the housing of the implantable medical device, the coil winding formed into a curved shape that conforms to a curvature of at least a portion of an inner surface of the housing that at least partially encloses the interior cavity, the coil winding positioned adjacent to the curvature of the inner surface so that the coil winding bends along and is positioned adjacent to the curvature of the inner surface. The electrical conductor may comprise any form of an electrical conductors described throughout this disclosure, including a wire formed of a conductive metal such as copper, or a multi-strand conductor such as Litz wire.

The coil winding positioned adjacent to the inner surface of the housing may include a spiral-wound planar coil, such as receive coil 70 as illustrated and described with respect to FIGS. 4A-4B. The coil winding positioned adjacent to the inner surface of the housing may include an infinity shaped coil winding such as receive coil 90 as illustrated and described with respect to FIGS. 5B-5C, or the dual-winding coil configuration 102 as illustrated and described with respect to FIG. 5D. The coil winding positioned adjacent to the inner surface of the housing may include an infinity shaped coil winding comprising three loops, wherein the first lop and the second loop of the coil winding are affixed or positioned adjacent to the inner surface of the housing and include a curvature along a longitudinal axis of the first and second loop that conforms to the curvature of the inner surface as illustrated and described in FIG. 7B. The third loop of the coil winding is orientated so that a central axis of the coil windings of the third loop corresponds to a longitudinal axis of the implantable medical device and lies in a plane or a set of coplanar planes that is/are perpendicular to the longitudinal axis of the device, as illustrated and described in FIG. 7B. In some examples, the portion of the housing that includes the inner surface comprised an antenna window, such as antenna window 40 as described through this disclosure. In some examples the portion of the housing is not formed from a separate antenna window, and is included in a portion of the housing, such as the second housing portion 36 as illustrated in FIG. 2B.

The receive antenna configuration of method 300 may include a plurality of receive coils that may be individually coupled to the recharging circuitry 206 of the implantable medical device, each receive coil configured to provide a separate current flow to the recharging circuitry when an electrical current is induced into the receive coil. The receive antenna configuration and/or the recharging circuitry is/are configured to sum together the individual electrical current flows provided by the received coil(s) of the receive antenna configuration to generate a recharging current. The recharging current may be applied to a recharging power source (battery 39—FIGS. 2A-2B) to recharging the rechargeable power source, or used to electrically power and operate the electrical circuitry of the implantable medical device.

In some examples of a receive antenna configuration having a plurality of receive coils, a first receive coil 55 may be positioned adjacent to and comprising a curved shape that conforms to the curvature of a portion of the inner surface of the housing, which may comprise an antenna window 40, while a second receive coil 65 is positioned as a flat planar coil positioned within the interior cavity 53 of the antenna window, as illustrated and described with respect to FIG. 3A. The first receive coil may be a spiral-wound planar coil such as receive coil 70 as illustrated and receive with respect to FIG. 4A, or may be an infinity shaped coil such as receive coil 90 as illustrated and describe with respect to FIGS. 5B-5C, or the dual-winding coil configuration 102 as illustrated and described with respect to FIG. 5D. First receive coil 55 and/or second receive coil 65 may be affixed, respectively, to separate ferrite sheets.

In some examples of a receive antenna configuration having a plurality of receive coils, a first receive coil 55 may be positioned adjacent to and have a curved shape that conforms to the curvature of a first portion of the inner surface of the housing, which may include an antenna window 40, and a second receive coil 112 may be positioned adjacent to and have a curved shape that conforms to the curvature of a second portion of the inner surface of the antenna window, as illustrated and described with respect to FIG. 6. In this example, one or both of the first receive coil 55 and the second receive coil 112 may comprise a spiral-wound planar coil or an infinity shaped coil winding. First receive coil 55 and/or second receive coil 65 may be affixed, respectively, to separate ferrite sheets. In this example, the receive antenna configuration may further include a third receive coil 65 positioned in the interior cavity 53 of the antenna window as illustrated and described with respect to FIG. 6. Third receive coil 65 may comprise a flat spiral-wound coil winding, which may or may not be affixed to a ferrite sheet 66.

In some examples of a receive antenna configuration having a plurality of receive coils, the receive antenna configuration may comprise an infinity shaped receive coil having a first loop, a second loop coupled to the first loop through a first crossover area, and a third loop coupled to the second loop through a second crossover area, the three-loop receive coil positioned within the antenna window 40 of implantable medical device 30 as illustrated and described with respect to FIG. 7B.

In some examples of a receive antenna configuration having a plurality of receive coils, the receive antenna configuration comprises a first receive coil 164 having an infinity shaped coil winding and a second receive coil 174 having an infinity shaped coil winding, the first receive coil 164 having a curved shape and positioned adjacent to a curved shaped first portion of the inner surface of the housing, which may including an antenna window 40, the second receive coil 174 having a curved shape and positioned adjacent to a curved shaped second portion of the inner surface of the antenna window, as illustrated and described with respect to FIGS. 8A-8B.

In some examples of a receive antenna configuration having a plurality of receive coils, the receive antenna configuration comprises a plurality receive coils, (e.g., first receive coil 184, second receive coil 185, third receive coil 186, and fourth receive coil 187), each of the plurality of receive coils comprising a spiral-wound planar coil have a curved shape that conform to a curvature of the inner surface of the antenna window 40, wherein the plurality of receive coils is positioned around and adjacent to the curved inner surface of the antenna window 40 and adjacent to one another along a longitudinal axis 189 as illustrated and described in FIGS. 9A-9B. The plurality of receive coils may or may not be affixed to one or more ferrite sheets positioned between the inner surface 51 and the individual receive coils.

Referring again to FIG. 14, method 300 includes summing, by recharging circuitry, one or more electrical currents induced into at least one receive coil of the receive antenna configuration to generate a recharging current (block 306). Summing the induced electrical currents to may include coupling each of a plurality of the receive coils of the receive antenna configuration to an individual diode, such as diodes 216C, 218D as illustrated and described with respect to schematic diagram 215 and FIG. 11. In various examples, summing the induced electrical currents may include filtering the current or currents generated in one or more of the receive coils of the receive antenna configuration using capacitors, such as capacitors 216B, 218B, and/or capacitor 221 as illustrated and described with respect to schematic diagram 215 and FIG. 11.

Referring again to FIG. 14, method 300 includes applying, by recharging circuitry, the generated recharging current to electrical circuitry of the implantable medical device 30 (block 308). In some examples, applying the recharging current to electrical circuitry includes applied to recharging current to a rechargeable power source, such as battery 39, of the implanted medical device 30 (block 308). In various examples, applying the recharging current to the power source includes controlling the coupling of the recharging current to a power source, such as power source 204 (FIG. 10) or power source 223 (FIG. 11), through a switching device, such as switching device 222, the switching device controlled by recharging circuitry, such as recharging circuitry 206 as illustrated and described with respect to FIG. 10 and/or schematic diagram 215 and FIG. 11). In some examples, applying the recharging current to electrical circuitry includes applied to recharging current to electrical circuitry, such as any of the electrical circuitry illustrated and describe with respect to IMD 15 in FIG. 10, to power and operate the implantable medical device.

Figure 15:
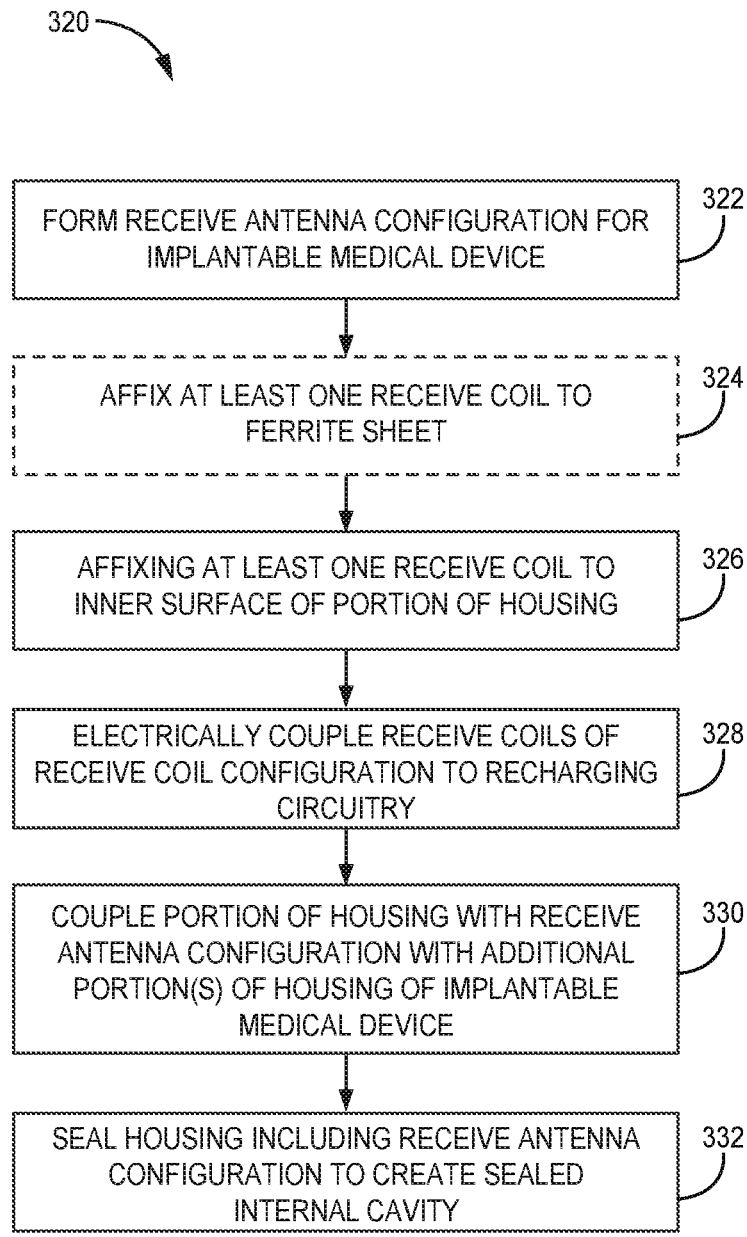
FIG. 15 is a flowchart illustrating another method according to various examples described in this disclosure.

FIG. 15 is a flowchart illustrating another method 320 according to various examples described in this disclosure. Method 320 includes a method for manufacturing a receive antenna configuration for an implanted medical device that is to be implanted within a patient according to the devices, systems, and techniques described herein. Method 320 is described as manufacturing a receive antenna configuration for an implantable medical device 30 (FIGS. 2A-2B) designed to be implanted within a chamber of the heart of a patient, and to include a receive antenna configuration configured to generate a recharging current when a magnetic field is imposed on the antenna, the recharging current for recharging a power source (e.g., battery 39) of the device 30. However, method 320 is not limited to manufacturing the implantable medical device 30 having the receive antenna configuration as illustrated and described for example with respect to FIGS. 2A-9B, and may be applied to the manufacturing process of a variety of implantable medical devices having a receive antenna configuration according to the examples as described throughout this disclosure, and any equivalents thereof.

Method 320 includes forming a receive antenna configuration for an implantable medical device 30 comprising at least one receive coil (block 322). The at least one receive coil may include a coil winding formed from an electrical conductor as a spiral-wound planar coil, such as receive coil 70 as illustrated and described with respect to FIGS. 4A-4B. The at least one receive coil may include a coil winding formed from an electrical conductor formed as an infinity shaped coil winding including two loops coupled at a crossover area, such as receive coil 90 as illustrated and described with respect to FIGS. 5A-5C. The at least one receive coil may include a dual-winding coil configuration 102 as illustrated and described with respect to FIG. 5D. The at least one receive coil may include a coil winding formed from an electrical conductor formed an infinity shaped coil winding including three loops as illustrated and described with respect to FIGS. 7A-7B.

The electrical conductor used to form the coil winding of the receive coils is not limited to any particular type of electrical conductor, and may be any type of electrical conductor that can be utilized to form the receive coils as described throughout this disclosure, including a wire comprising from a conductive metal such as copper, or a multi-strand electrical conductor such as Litz wire. The coil winding may be formed using any techniques that may be utilized to form the receive coils, including any of the technique as describe throughout this disclosure, including twisting a loop of coil windings of an electrical conductor to form the infinity shaped coil windings as described herein.

Referring again to FIG. 15, method 320 includes affixing at least one receive coil of the antenna configuration to an inner surface of a portion of the housing the implantable medical device (block 326). In some examples, the portion of the housing including the inner surface is a separate antenna window portion. In some examples, the portion of the housing including the inner surface is not a separate antenna window portion, wherein the inner surface is included in a portion of the device affixed to an end cap at one end and to an additional portion of the housing at the opposite end. Affixing the at least one receive coil to the inner surface of the housing may include affixing the at least one receive coil directly to the inner surface so that the coil winding forming the at least one receive coil are in contact with at least some portion of the inner surface. Affixing the at least one receive coil to the inner surface of the housing may include affixing the at least one receive coil to a first surface of a flexible ferrite sheet (block 324), and then affixing a second surface of the ferrite sheet opposite the first surface to the inner surface of the housing so that the ferrite sheet is positioned between the inner surface and the coil windings of the at least one receive coil (block 326).

Affixing the at least one receive coil to the inner surface of the housing may include bending the coil windings of the at least one receive antenna so that the at least one receive coil has a curved shape that corresponds to a curved shaped on the inner surface of the housing, and affixing the at least one receive antenna so the coil windings of the at least one receive antenna are position adjacent to the inner surface and so that the curved shape of the at least one receive antenna corresponds to at least a portion of the curved inner surface. In some examples, affixing the at least one receive coil to the inner surface of the housing includes affixing a first loop and a second loop of a three-loop infinity shaped coil to the inner surface of the housing, and positioning a third loop of the three-loop infinity shaped coil within the interior cavity that is at least partially enclosed by the inner surface.

Affixing the at least one receive coil to the inner surface of the housing may include affixing a plurality of receive coil windings directly to the inner surface of the housing (e.g., without the intervening ferrite sheet). In some examples, the plurality of receive coils includes two individual infinity shaped receive coils. In some examples, the plurality of receive coils includes a plurality of spiral-wound planar coils. Affixing the at least one receive coil to the inner surface of the antenna window may include positioning a second receive coil within the interior cavity that is at least partially enclosed by the inner surface.

Method 320 includes electrically coupling the receive coil or coils of the receive antenna configuration to a recharging circuitry of the device 30 (block 328). Coupling the receive antenna configuration may include coupling a first lead of each receive coil to an individual diode, and coupling a second lead of each receive coil to a common voltage conductor. In examples of the receive antenna configuration that include a plurality of receive coils, coupling the receive antenna configuration to the recharging circuitry may include coupling each receive coils to electrical circuitry, including electrical diodes, so that any electrical currents generated in any of the receive coils can be summed together to generate a recharging current comprising the total of the electrical current(s) being generated by any and all of the receive coils at any given time.

Method 320 includes coupling the portion of the housing including the receive antenna configuration with one or more additional portions of the housing of the implantable medical device (block 330). Coupling the portion of the housing including the receive antenna configuration with additional portions of the housing may include coupling an antenna window such as antenna window 40 with a first housing portion 31 and a second housing portion 36 as illustrated and described with respect to FIG. 2A. In some examples, the portion of the housing may include or be formed as part the housing, such as second housing portion 36 as shown in FIG. 2B and coupling the portion of the housing with other portions of the housing may include coupling the portion of the housing including the receive antenna configuration to one additional portion of the housing, such as first housing portion 31.

Method 320 includes sealing the portion of the housing to the additional portion of the housing to create a sealed internal cavity that includes the receive antenna configuration (block 332). Sealing the antenna window may include forming a first sealed seam 41 between a top side of the antenna window with a first housing portion 31, and forming a second sealed seam 42 between a bottom side of the antenna window with a second housing portion 36 of the implantable medical device as illustrated and described with respect to FIG. 2A. Sealing the portion of the housing including the receive antenna configuration may include forming a first sealed seam 42 between the portion of the housing including the receive antenna configuration and another portion of the housing as illustrated and described with respect to FIG. 2B. Sealing the portion of the housing and/or the antenna window may include the use of any materials, such as adhesives, and or any type of welding or bonding process that may be used to provide a hermetic seal between the type of material used to from the portions of the housing being seemingly joined, or between the antenna window and other portions of the housing and the type or types of material used to form the additional portions of the housing to which the antenna window is coupled.

Use of the devices, systems, and techniques described in this disclosure are not limited to use in devices only during recharging sessions applied to the devices. An example of a receive antenna configuration as described throughout this disclosure, or any equivalent thereof, may be included a part of a passive device. In some examples, the passive device may not include an internal power source capable of storing electrical energy for extended periods of time during which the device may be required to operate, wherein the device may only operate when and during a time or over time periods when the device is being energized from an external power source, for example by receiving power from an external device through inductively coupled electrical energy provided by the external device. When operating a passive device, an external device that may include a transmit coil arranged to be electrically energized to generate a magnetic field that is imposed on the receive antenna configuration incorporated within or coupled to the passive device. The imposed magnetic field generates one or more currents in the receive antenna configuration of the passive device, and additional circuitry of the passive device is arranged to receive these induced currents to electrically power and operate the passive device. These current(s) inducted into the receive antenna configuration may be referred to as "operating current" because they are used to electrically power and operate the passive implantable medical device.

Once powered by the induced currents, the implanted medical device may perform a variety of functions, including sensing physiological parameter associated with a patient in order to monitoring and/or diagnose a condition of the patient, and/or to provide therapy, such as electrical stimulation therapy, to the patient while the passive device is being powered through the imposed magnetic field. The need to operate the passive device in some instances may only require that the device be powered for a short interval of time, for example for a thirty-minute time period and only periodically, for example once daily, or in other examples one time per week or once monthly. By eliminating the need to have a power source located within or as part of the passive device, the overall size and/or the dimension of the passive device may be reduced relative to a similar device that includes a power source included as part of the device. The smaller size for the passive device may allow a less intrusive implantation to implant the passive device at the implantation site, and may contribute to patient comfort following implantation of the device due to the smaller size of the implanted device.

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processor circuitry," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random-access memory (RAM), read-only memory (ROM), non-volatile random-access memory (NVRAM), electrically erasable programmable read-only memory (EEPROM), FLASH memory, magnetic media, optical media, or the like that is tangible. The computer-readable storage media may be referred to as non-transitory. A server, client computing device, or any other computing device may also contain a more portable removable memory type to enable easy data transfer or offline data analysis. The instructions may be executed to support one or more aspects of the functionality described in this disclosure.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various aspects of this disclosure have been described. These and other aspects are within the scope of the following claims.

What is claimed is:

1. An implantable medical device comprising:
   a rechargeable power source coupled to one or more electrical circuits located within a housing of the implantable medical device, the rechargeable power source configured to provide electrical power to the one or more electrical circuits;
   a receive antenna configuration comprising a single receive coil comprising an electrical conductor forming a planar coil winding, the planar coil winding positioned within an interior cavity enclosed by the housing of the implantable medical device, the planar coil winding disposed along a curvature of at least a portion of an inner surface of the housing that at least partially encloses the interior cavity, the planar coil winding positioned adjacent to the curvature of the inner surface so that the planar coil winding bends along and is positioned adjacent to the curvature of at least the portion of the inner surface, the single receive coil configured to generate an electrical current induced into the single receive coil when an externally generated magnetic field is imposed onto the single receive coil; and
   recharging circuitry coupled to the single receive coil and to the rechargeable power source, the recharging circuitry configured to receive the electrical current induced into the single receive coil and to provide a recharging current to the rechargeable power source,
   wherein the planar coil winding of the single receive coil comprises a half-twist such that the single receive coil and the recharging circuitry are configured to provide at least a minimum level of recharging current for a given level of magnetic field intensity provided by the magnetic field imposed on the single receive coil for a plurality of orientations of a magnetic field direction of the magnetic field relative to an orientation of the implantable medical device, and
   wherein, to form the half-twist of the planar coil winding of the single receive coil, the electrical conductor of the single receive coil is wound into a loop and at least a first portion of the loop is twisted about 180 degrees with respect to at least a second portion of the loop to form an infinity-shaped coil winding.

2. The implantable medical device of claim 1, wherein the infinity shaped coil winding comprises a first loop, a second loop, and a crossover area coupling the first loop and the second loop, the first loop and the second loop extending in opposite directions away from the crossover area along a longitudinal axis of the planar coil winding, the longitudinal axis having a curved shape that corresponds to the curvature of the inner surface of the portion of the housing positioned adjacent to the infinity shaped coil winding.

3. The implantable medical device of claim 1, wherein the infinity shaped coil winding comprises a first loop, a second loop, a third loop, a first crossover area coupling the first loop and the second loop, and a second crossover area coupling the second loop to the third loop,
    wherein the first loop and the second loop extend in opposite directions away from the first crossover area along a first longitudinal coil axis having a curved shape that corresponds to the curvature of the inner surface of the portion of the housing adjacent to the first loop and the second loop, and
    wherein the third loop of the planar coil winding is orientated so that a central axis of the third loop corresponds to a longitudinal axis of the implantable medical device and lie in a plane or a set of coplanar planes perpendicular to the longitudinal axis of the implantable medical device.

4. The implantable medical device of claim 1,
    wherein the single receive coil comprises a first receive coil, and
    wherein the receive antenna configuration of the medical device comprises a second receive coil formed as a flat spiral-wound planar coil, the second receive coil positioned away from the inner surface of the housing and within the interior cavity of the housing.

5. The implantable medical device of claim 1,
    wherein the single receive coil comprises a first infinity shaped receive coil positioned adjacent to the inner surface and comprising a curved shape that conforms to the curvature of a first portion of the inner surface of the housing, and
    wherein the receive antenna configuration of the medical device comprises a second infinity shaped receive coil positioned adjacent to the inner surface and comprising a curved shape that conforms to the curvature of a second portion of the inner surface of the housing.

6. The implantable medical device of claim 1, wherein the portion of the housing enclosing the interior cavity comprises a cylindrical shaped exterior extending along a longitudinal axis of the implantable medical device comprising a circular shape in cross-section to the longitudinal axis.

7. The implantable medical device of claim 1, wherein the implantable medical device includes one or more fixation members configured to secure the implantable medical device at an implant site located within the interior portion of a chamber of a heart of a patient.

8. The implantable medical device of claim 1, wherein the receive antenna configuration is positioned adjacent to and encircled by an antenna window forming the portion of the housing of the implantable medical device, the antenna window sealingly coupled to a first portion of the housing at a first seam and sealingly coupled to a second portion of the housing at a second seam, the second portion of the housing sealingly coupled to an end cap of the implanted medical device to form the housing as a hermetically sealed enclosure.

9. The implantable medical device of claim 8, wherein the antenna window is formed from a material comprising sapphire.

10. The implantable medical device of claim 1, wherein at least a portion of the housing that at least partially encloses the receive antenna configuration is formed from a material comprising a biocompatible ceramic.

11. The implantable medical device of claim 1, wherein at least a portion of the housing that at least partially encloses the receive antenna configuration is formed from a metal ceramic material made using a metal injection molding process.

12. A method for forming a receive antenna configuration for an implantable medical device, the method comprising:
    forming an electrical conductor into a single receive coil, the single receive coil comprising a first set of planar coil windings forming a first loop, a second set of planar coil windings forming a second loop, and a crossover area comprising a half-twist coupling the planar coil windings of the first loop with the planar coil windings of the second loop, wherein, to form the half-twist coupling the planar coil windings, the electrical conductor of the single receive coil is wound into the first loop and at least a first portion of the first loop is twisted about 180 degrees with respect to at least a second portion of the first loop to form the second loop, thereby forming the single receive coil into an infinity shape,
    wherein the single receive coil is configured to provide at least a minimum level of recharging current for a given level of magnetic field intensity provided by a magnetic field imposed on the single receive coil for a plurality of orientations of a magnetic field direction of the magnetic field relative to an orientation of the implantable medical device;
    affixing the single receive coil comprising the infinity shape to an inner surface of an antenna window portion of a housing of the implantable medical device so that a curvature of a longitudinal axis of the single receive coil conforms to a curvature of the inner surface;
    electrically coupling the single receive coil to a recharging circuitry of the implantable medical device; and
    coupling the antenna window with one or more additional portions of the housing to enclose the single receive coil and the recharging circuitry within the housing of the implantable medical device.

13. The method of claim 12, further comprising:
    sealing the antenna window to the one or more additional portions of the housing to form a hermetically sealed interior cavity, wherein the single receive coil is positioned within the interior cavity.

14. The method of claim 12, wherein the antenna window encloses a cylindrical shaped interior cavity having a circular cross-section so that the curvature of the inner surface comprises a circular shape, the curvature of the longitudinal axis of the single receive coil conforming to the circular shape of the inner surface.

15. The method of claim 12,
    wherein forming the electrical conductor into the single receive coil comprises forming a first electrical conductor into a single first receive coil comprising the first set of planar coil windings coupled to the second set of planar coil windings forming a first infinity shaped receive coil having a curved shape relative to a first receive coil longitudinal axis, wherein the method further comprises forming a second electrical conductor into a second receive coil comprising a third set of planar coil windings coupled to a fourth set of coil windings forming a second infinity shaped receive coil having a curved shape relative to a second receive coil longitudinal axis;

wherein affixing the single receive coil to an inner surface of the antenna window comprises affixing the first receive coil to the inner surface of the antenna window so that the first receive coil longitudinal axis bends around a first portion of the curvature of the inner surface, wherein the method further comprises affixing the second receive coil to the inner surface of the antenna window so that that the second receive coil longitudinal axis bends around a second portion of the curvature of the inner surface, and wherein the first receive coil longitudinal axis aligns with the second receive coil longitudinal axis relative to a height dimension of the antenna window.

16. The method of claim 12, wherein the antenna window is formed from a material comprising sapphire.

17. The method of claim 12, wherein the housing including the antenna window comprises a cylindrical shaped exterior extending along a longitudinal axis of the implantable medical device comprising a circular shape in cross-section to the longitudinal axis.

18. A system for recharging a power source located in an implanted medical device implanted in a patient, the system comprising:

an electrical power source;

at least one recharging coil coupled to the electrical power source and configured to generate a magnetic field having a magnetic field direction when electrically energized by the electrical power source;

a receive antenna configuration comprising a single receive coil comprising an electrical conductor forming a planar coil winding, the planar coil winding positioned within an interior cavity enclosed by the housing of the implantable medical device, the planar coil winding disposed along a curvature of at least a portion of an inner surface of the housing that at least partially encloses the interior cavity, the planar coil winding positioned adjacent to the curvature of the inner surface so that the planar coil winding bends along and is positioned adjacent to the curvature of at least the portion of the inner surface, the single receive coil configured to generate an electrical current induced into the single receive coil when an externally generated magnetic field is imposed onto the single receive coil; and recharging circuitry coupled to the receive antenna configuration, the recharging circuitry configured to sum electrical current induced into the single receive coil and to generate a recharging current to recharge the power source located in an implanted medical device; and a switching device coupled to the receive antenna configuration and the power source of the implanted medical device, the switching device configured to be controlled by the recharging circuitry to couple the recharging current to the power source to recharge the electrical energy stored in the power source, wherein the planar coil winding of the single receive coil comprises a half-twist such that the single receive coil and the recharging circuitry are configured to provide at least a minimum level of recharging current for a given level of magnetic field intensity provided by the magnetic field imposed on the single receive coil for a plurality of orientations of the magnetic field direction relative to an orientation of the implantable medical device, and wherein, to form the half-twist of the planar coil winding of the single receive coil, the electrical conductor of the single receive coil is wound into a loop and at least a first portion of the loop is twisted about 180 degrees with respect to at least a second portion of the loop to form an infinity-shaped coil winding.

19. The system of claim 18, wherein the single receive coil comprises a first infinity shaped receive coil positioned adjacent to the inner surface and comprising a curved shape that conforms to the curvature of a first portion of the inner surface of the housing, and wherein the receive antenna configuration comprises a second infinity shaped receive coil positioned adjacent to the inner surface and comprising a curved shape that conforms to the curvature of a second portion of the inner surface of the housing.

20. The system of claim 18, wherein the housing including an antenna window comprising a cylindrical shaped exterior extending along a longitudinal axis of the implantable medical device and comprising a circular shape in cross-section to the longitudinal axis.

21. The system of claim 20, wherein the antenna window is formed from a material comprising sapphire.

22. The system of claim 18, wherein at least a portion of the housing that at least partially encloses the receive antenna configuration is formed from a material comprising a biocompatible ceramic.

23. The system of claim 18, wherein at least a portion of the housing that at least partially encloses the receive antenna configuration is formed from a metal ceramic material made using a metal injection molding process.

24. A method for recharging a power source located in an implantable medical device implanted in a patient, the method comprising:

receiving, at a receive antenna configuration of the implantable medical device, a magnetic field generated by at least one recharging coil located externally to the patient, wherein the magnetic field induces one or more electrical currents in a single receive coil forming the receive antenna configuration, wherein the single of the receive coil comprises a planar coil winding positioned within an interior cavity enclosed by the housing of the implantable medical device, the planar coil winding formed into a curved shape that disposed along a curvature of at least a portion of an inner surface of the housing that at least partially encloses the interior cavity, the planar coil winding positioned adjacent to the curvature of the inner surface so that the planar coil winding bends along and is positioned adjacent to the curvature of at least the portion of the inner surface, generating, using the receive antenna configuration, one or more electrical currents induced into the single receive coil when an externally generated magnetic field is received at the single receive coil;

summing, by recharging circuitry, the one or more electrical currents to form a recharging current; and applying, by the recharging circuitry, the recharging current to the power source of the implantable medical device to recharge the energy level stored in the power source, wherein the planar coil winding of the single receive coil comprises a half-twist such that the single receive coil and the recharging circuitry are configured to provide at least a minimum level of the recharging current for a given level of magnetic field intensity provided by the magnetic field imposed on the single receive coil for a plurality of orientations of a magnetic field direction of the magnetic field relative to an orientation of the implantable medical device, and wherein, to form the half-twist of the planar coil winding of the single receive coil, the electrical conductor of the single receive coil is wound into a loop and at least a first portion of the loop is twisted about 180 degrees with respect to at least a second portion of the loop to form an infinity-shaped coil winding.

25. The method of claim 24, wherein the infinity shaped coil winding comprises a first loop, a second loop, and a crossover area coupling the first loop and the second loop, the first loop and the second loop extending in opposite directions away from the crossover area along a longitudinal axis of the planar coil winding, the longitudinal axis having a curved shape that corresponds to the curvature of the inner surface of the portion of the housing positioned adjacent to the infinity shaped coil winding.

26. The method of claim 24, wherein the infinity shaped coil winding comprises a first loop, a second loop, a third loop, a first crossover area coupling the first loop and the second loop, and a second crossover area coupling the second loop to the third loop, wherein the first loop and the second loop extend in opposite directions away from the first crossover area along a first longitudinal coil axis having a curved shape that corresponds to the curvature of the inner surface of the portion of the housing adjacent to the first loop and the second loop, and wherein the third loop of the planar coil winding is orientated so that a central axis of the third loop corresponds to a longitudinal axis of the implantable medical device and lie in a plane or a set of coplanar planes perpendicular to the longitudinal axis of the implantable medical device.

27. The method of claim 24, wherein the single receive coil comprises a first infinity shaped receive coil positioned adjacent to the inner surface and comprising a curved shape that conforms to the curvature of a first portion of the inner surface of the housing, and wherein the receive antenna configuration of the implantable medical device comprises a second infinity shaped receive coil positioned adjacent to the inner surface and comprising a curved shape that conforms to the curvature of a second portion of the inner surface of the housing.

28. The method of claim 24, wherein the portion of the housing encircling the receive antenna configurations includes an antenna window comprises a cylindrical shaped exterior extending along a longitudinal axis of the implantable medical device comprising a circular shape in cross-section to the longitudinal axis.

29. The method of claim 28, wherein the antenna window is formed from a material comprising sapphire.

* * * * *